US012440333B1

(12) United States Patent
Schneider et al.

(10) Patent No.: US 12,440,333 B1
(45) Date of Patent: Oct. 14, 2025

(54) PROSTHETIC HEART VALVES

(71) Applicant: Laplace Interventional Inc., Plymouth, MN (US)

(72) Inventors: Lucas Tradd Schneider, Champlin, MN (US); Gunnar Paul Askegaard, Brainerd, MN (US); Ramji Iyer, Plymouth, MN (US)

(73) Assignee: Laplace Interventional Inc., Plymouth, MN (US)

( * ) Notice: Subject to any disclaimer, the term of this patent is extended or adjusted under 35 U.S.C. 154(b) by 0 days.

(21) Appl. No.: 19/169,240

(22) Filed: Apr. 3, 2025

Related U.S. Application Data

(60) Provisional application No. 63/672,485, filed on Jul. 17, 2024.

(51) Int. Cl.
*A61F 2/24* (2006.01)

(52) U.S. Cl.
CPC .... *A61F 2/2436* (2013.01); *A61F 2220/0008* (2013.01)

(58) Field of Classification Search
CPC ........................ A61F 2/2436; A61F 2220/0008
See application file for complete search history.

(56) References Cited

U.S. PATENT DOCUMENTS

| | | | |
|---|---|---|---|
| 4,510,926 | A | 4/1985 | Inaba |
| 4,573,452 | A | 3/1986 | Greenberg |
| 4,617,916 | A | 10/1986 | LeVahn et al. |
| 5,824,007 | A | 10/1998 | Faraz et al. |
| 5,888,190 | A | 3/1999 | Meyer et al. |
| 6,632,170 | B1 | 10/2003 | Bohanan et al. |
| 7,644,898 | B2 | 1/2010 | White et al. |
| 8,083,196 | B2 | 12/2011 | Chang |
| 8,231,529 | B2 | 7/2012 | Kanekasu et al. |
| 8,617,064 | B2 | 12/2013 | Farley |
| 8,870,141 | B2 | 10/2014 | Abri et al. |
| 9,078,635 | B2 | 7/2015 | Menendez et al. |
| 10,004,569 | B2 | 6/2018 | Singh et al. |
| 10,702,256 | B2 | 7/2020 | Harvey et al. |
| 11,510,777 | B1 | 11/2022 | Iyer et al. |
| 11,638,643 | B1 * | 5/2023 | Askegaard ............ A61F 2/2409 623/2.11 |

(Continued)

FOREIGN PATENT DOCUMENTS

| | | |
|---|---|---|
| WO | WO 2024/020023 | 1/2024 |

*Primary Examiner* — Suzette J Gherbi
(74) *Attorney, Agent, or Firm* — Fish & Richardson P.C.

(57) ABSTRACT

Prosthetic heart valves may be delivered to a targeted native heart valve site via one or more delivery catheters. In some embodiments, the prosthetic heart valve includes structural features that securely anchor the prosthetic heart valve to the anatomy at the site of the native heart valve. Such structural features can provide robust migration resistance. In addition, the prosthetic heart valves can include structural features that improve sealing between the prosthetic valve and native valve anatomy to mitigate paravalvular leakage. In particular implementations, the prosthetic heart valves occupy a small delivery profile, thereby facilitating a smaller delivery catheter system for advancement to the heart. Some delivery catheter systems can include a curved inner catheter to facilitate deployment of the prosthetic heart valve to a native tricuspid valve site via a superior vena cava or inferior vena cava.

7 Claims, 30 Drawing Sheets

FIG. 17

(56) References Cited

U.S. PATENT DOCUMENTS

| | | | |
|---|---|---|---|
| 11,672,655 | B1 | 6/2023 | Iyer |
| 11,701,223 | B2 | 7/2023 | Iyer |
| 11,701,226 | B2 | 7/2023 | Tegels |
| 11,712,336 | B1 | 8/2023 | Schneider |
| 11,759,316 | B1 | 9/2023 | Askegaard |
| 11,806,235 | B1 | 11/2023 | Schneider |
| 12,064,349 | B1 | 8/2024 | Iyer et al. |
| 2010/0121435 | A1 | 5/2010 | Subramanian |
| 2020/0253686 | A1 | 8/2020 | Krause et al. |
| 2021/0186693 | A1 | 6/2021 | Vidlund, I et al. |
| 2021/0244535 | A1* | 8/2021 | Iyer ........................ A61F 2/2418 |
| 2022/0096231 | A1 | 3/2022 | Ganesan |
| 2023/0270552 | A1 | 8/2023 | Shing |
| 2024/0024067 | A1 | 1/2024 | Bowes |
| 2024/0350263 | A1 | 10/2024 | Iyer et al. |

* cited by examiner

RA – Right Atrium
LA – Left Atrium
RV – Right Ventricle
LV – Left Ventricle
Ao – Aorta
MPA – Main Pulmonary Artery
SVC – Superior Vena Cava
IVC – Inferior Vena Cava
RVOT – Right Ventricular Outflow Tract

FIG. 12
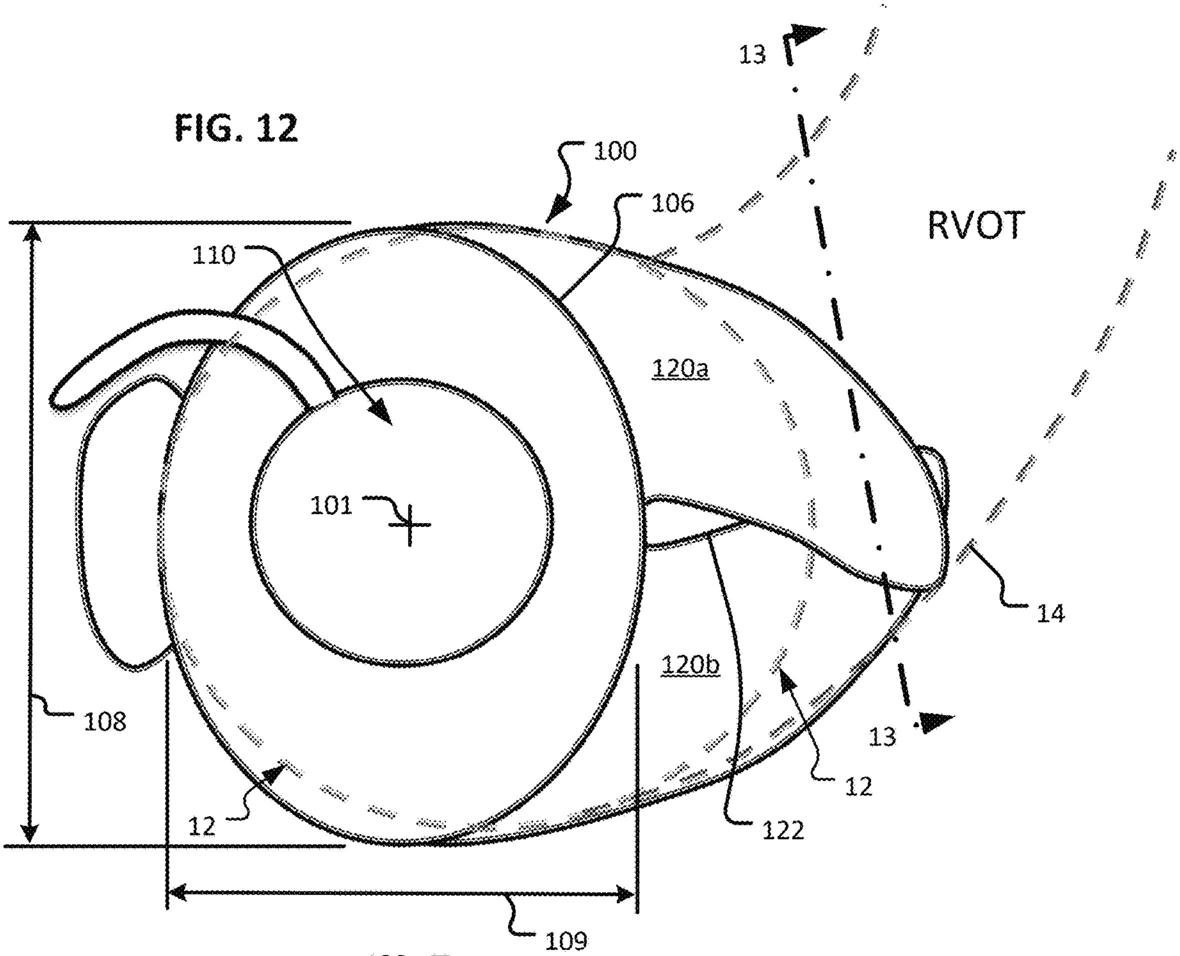
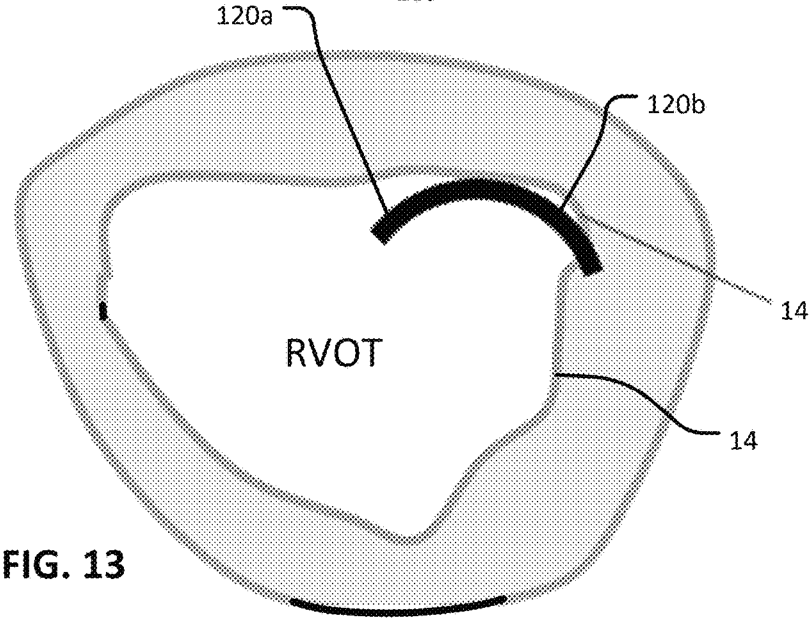
FIG. 13

PROSTHETIC HEART VALVES

CROSS-REFERENCE TO RELATED APPLICATIONS

This application claims the benefit of U.S. Provisional Application Ser. No. 63/672,485 filed Jul. 17, 2024. The disclosure of the prior application is considered part of (and is incorporated by reference in) the disclosure of this application.

FIELD OF INVENTION

This disclosure generally relates to prosthetic heart valve systems. For example, this disclosure relates to transcatheter deliverable prosthetic heart valves that are adapted to be used to replace a sub-optimally functioning native heart valve, including but not limited to a tricuspid valve.

BACKGROUND

A human heart includes four types of heart valves that are arranged to ensure blood flow in specific directions: mitral, tricuspid, aortic and pulmonary valves. The aortic and pulmonary valves are semilunar valves, which are in the arteries leaving the heart, and prevent blood from flowing back into left ventricle and right ventricle respectively when closed. The mitral and tricuspid valves are atrio-ventricular valves, which are between the atria and the ventricles, and prevent blood from flowing back into left atrium and right atrium respectively when closed. Conditions of stenosis (when valve does not open fully) as well as regurgitation/insufficiency (when valve does not close properly resulting in leaks) are recognized as significant contributors to mortality and morbidity.

Some valve replacement systems include valve prostheses that are compressed into a delivery catheter, also referred to as transcatheter valves, so as to avoid open-heart surgery. Many transcatheter valve prostheses have a tubular frame that may or may not be axisymmetric, and include two or more leaflets. While these transcatheter valve prostheses can be compressed into a catheter, they may still require a large delivery system (for example, a required catheter size of 45 French). This is especially true in case of mitral valve replacement systems and tricuspid valve replacement systems, which often require valve prostheses with a larger profile.

SUMMARY

Some embodiments described herein include a prosthetic heart valve that may be delivered to a targeted native heart valve site via one or more delivery catheters. In some embodiments, a prosthetic heart valve includes structural features that securely anchor the prosthetic heart valve to the anatomy at the site of the native heart valve. Such structural features can provide robust migration resistance. In addition, the prosthetic heart valves can include structural features that improve sealing between the prosthetic valve and native valve anatomy to mitigate paravalvular leakage. In particular implementations, the prosthetic heart valves occupy a small delivery profile, thereby facilitating a smaller delivery catheter system for advancement to the heart. Some delivery catheter systems can include a curved inner catheter to facilitate deployment of the prosthetic heart valve to a native tricuspid valve site via a superior vena cava or inferior vena cava.

In one aspect, this disclosure is directed to a prosthetic heart valve that includes a main body comprising an inflow end portion and an outflow end portion, and an occluder extending between the inflow end and outflow end portions and comprising valve leaflets attached to the main body in an arrangement that: (i) allows blood flow through the occluder in a direction from the inflow end portion toward the outflow end portion along a central axis of the occluder and (ii) prevents blood flow through the occluder in a direction from the outflow end portion toward the inflow end portion. The prosthetic heart valve also includes a first anterior flap extending from the outflow end portion in a first direction that is transverse to the central axis; a posterior flap extending from the outflow end portion in a second direction that is opposite of the first direction; and a posterior arm extending from the inflow end portion in the second direction.

Such a prosthetic heart valve may optionally include one or more of the following features. The prosthetic heart valve may also include an anterior arm extending from the inflow end portion in the first direction. The prosthetic heart valve may also include a second anterior flap extending from the outflow end portion in the first direction. The first and second anterior flaps may overlap each other. A cross-sectional shape of the first and second anterior flaps taken perpendicularly to the first direction may be arcuate.

In another aspect, this disclosure is directed to another prosthetic heart valve. The prosthetic heart valve includes a main body comprising an inflow end portion and an outflow end portion, and an occluder extending between the inflow end and outflow end portions and comprising valve leaflets attached to the main body in an arrangement that: (i) allows blood flow through the occluder in a direction from the inflow end portion toward the outflow end portion along a central axis of the occluder and (ii) prevents blood flow through the occluder in a direction from the outflow end portion toward the inflow end portion. The prosthetic heart valve also includes an anterior flap extending from the outflow end portion in a first direction that is transverse to the central axis; a posterior flap extending from the outflow end portion in a second direction that is opposite of the first direction; and an anterior arm extending from the inflow end portion in the first direction. In another aspect, this disclosure is directed to another prosthetic heart valve.

The prosthetic heart valve includes a main body comprising an inflow end portion and an outflow end portion, and an occluder extending between the inflow end and outflow end portions and comprising valve leaflets attached to the main body in an arrangement that: (i) allows blood flow through the occluder in a direction from the inflow end portion toward the outflow end portion along a central axis of the occluder and (ii) prevents blood flow through the occluder in a direction from the outflow end portion toward the inflow end portion. The prosthetic heart valve also includes a first anterior flap extending from the outflow end portion in a first direction that is transverse to the central axis; and a second anterior flap extending from the outflow end portion in the first direction. A cross-sectional shape of the first and second anterior flaps taken perpendicularly to the first direction is arcuate from an outer edge of the first anterior flap to an outer edge of the second anterior flap.

In another aspect, this disclosure is directed to another prosthetic heart valve. The prosthetic heart valve includes a main body comprising an inflow end portion and an outflow end portion, and an occluder extending between the inflow end and outflow end portions and comprising valve leaflets attached to the main body in an arrangement that: (i) allows blood flow through the occluder in a direction from the inflow end portion toward the outflow end portion along a central axis of the occluder and (ii) prevents blood flow through the occluder in a direction from the outflow end portion toward the inflow end portion. The prosthetic heart valve also includes a first anterior flap extending from the outflow end portion in a first direction that is transverse to the central axis; a second anterior flap extending from the outflow end portion in the first direction; a first posterior flap extending from the outflow end portion in a second direction that is opposite of the first direction; and a second posterior flap extending from the outflow end portion in the second direction. A passageway is defined between the first and second posterior flaps. The first and second posterior flaps extend from the outflow end portion farther than the first and second anterior flaps.

In another aspect, this disclosure is directed to a method of deploying a prosthetic heart valve. The method includes engaging any of the prosthetic heart valves described herein with anatomical structures of a native tricuspid valve. The lateral anterior flap extends into a right ventricular outflow tract (RVOT) and engages with a lateral wall of the RVOT to provide anchoring during diastole.

In another aspect, this disclosure is directed to another method of deploying a prosthetic heart valve. The method includes engaging any of the prosthetic heart valves described herein with anatomical structures of a native tricuspid valve. A distal end portion of the posterior arm rests against an interior wall of an inferior vena cava, or coronary sinus, or a right atrium.

In another aspect, this disclosure is directed to another method of deploying a prosthetic heart valve. The method includes engaging any of the prosthetic heart valves described herein with anatomical structures of a native tricuspid valve. A distal end portion of the anterior arm rests against an interior wall of a right atrial appendage.

Various types of deployment systems may be used in combination with the prosthetic tricuspid valves described herein. In some embodiments described herein, such a deployment system may include an outer sheath catheter defining a first lumen; a middle deflectable catheter slidably disposed in the first lumen and defining a second lumen, the middle deflectable catheter comprising a selectively deflectable distal end portion with at least one plane of deflection; and an inner control catheter slidably disposed in the second lumen and including one or more control wires that configure the inner control catheter to releasably couple with a prosthetic heart valve. The inner control catheter includes a distal end portion that, in some embodiments, elastically transitions to a naturally curved configuration when the inner control catheter converts from being radially constrained to being radially unconstrained. In some embodiments, the distal end portion defines an interior angle of less than 135 degrees when in the naturally curved configuration. In some embodiments, the inner control catheter is linear and has no natural curved configuration.

In another aspect, this disclosure is directed to another method of deploying a prosthetic heart valve. The method includes advancing the prosthetic heart valve toward a native tricuspid valve, via a jugular vein and a superior vena cava, while the prosthetic heart valve is releasably coupled to a prosthetic heart valve deployment system and diametrically constrained in a low profile delivery configuration. The prosthetic heart valve deployment system includes an outer sheath catheter defining a first lumen; a middle deflectable catheter slidably disposed in the first lumen and defining a second lumen, the middle deflectable catheter comprising a selectively deflectable distal end portion; and an inner control catheter slidably disposed in the second lumen and including one or more control wires that are releasably coupled with the prosthetic heart valve. The inner control catheter includes a distal end portion constrained in the first lumen. The method also includes retracting the outer sheath relative to the inner control catheter to allow the distal end portion of the inner control catheter to become radially unconstrained and to elastically transition to a curved configuration; and deflecting the selectively deflectable distal end portion of the middle deflectable catheter so that the inner control catheter and the middle deflectable catheter in combination are curved by at least 90° relative to the outer sheath.

In another aspect, this disclosure is directed to a prosthetic heart valve deployment system that includes: an outer sheath catheter defining a first lumen; a middle deflectable catheter slidably disposed in the first lumen and defining a second lumen, the middle deflectable catheter comprising a selectively deflectable distal end portion with at least one plane of deflection; and an inner control catheter slidably disposed in the second lumen and including one or more control wires that configure the inner control catheter to releasably couple with a prosthetic heart valve. The inner control catheter includes a distal end portion that elastically transitions to a naturally curved configuration when the inner control catheter converts from being radially constrained to being radially unconstrained.

In another aspect, this disclosure is directed to another method of deploying a prosthetic heart valve. The method includes advancing the prosthetic heart valve toward a native tricuspid valve, via a femoral vein and an inferior vena cava, while the prosthetic heart valve is releasably coupled to a prosthetic heart valve deployment system and diametrically constrained in a low profile delivery configuration. The prosthetic heart valve deployment system includes an outer sheath catheter defining a first lumen; a middle deflectable catheter slidably disposed in the first lumen and defining a second lumen, the middle deflectable catheter comprising a selectively deflectable distal end portion; and an inner control catheter slidably disposed in the second lumen and including one or more control wires that are releasably coupled with the prosthetic heart valve. The inner control catheter is selectively deflectable and/or includes a curved distal end portion that is curved by less than 20° when constrained in the first lumen. The method also includes advancing the inner control catheter relative to the outer sheath to allow the curved distal end portion to become unconstrained and to elastically transition to a curved configuration that is curved by at least 45° relative to the outer sheath or to use the tensioning of a suture member to cause the otherwise linear inner control catheter to become curved by a desired amount; and deflecting the selectively deflectable distal end portion of the middle deflectable catheter so that the inner control catheter and the middle deflectable catheter in combination are curved by at least 90° relative to the outer sheath.

Any of the prosthetic heart valves described herein may optionally include one or more of the following additional features. In some embodiments, portions of the first anterior flap and the second anterior flap overlap each other. The prosthetic tricuspid valve may also include a posterior flap extending laterally from the end of the main body in an opposite direction as the first and second anterior flaps. In some embodiments, the first and second anterior flaps extend farther laterally than the posterior flap. In particular embodiments, the first and second anterior flaps in combination are wider (in the septal to lateral direction) than the posterior flap. A framework of the prosthetic tricuspid valve (that comprises the main body, the first and second anterior flaps, and the posterior flap) may be made of a single, unitary material that was cut and expanded. In some embodiments, a distal tip portion of the posterior flap extends along an axis that is at a non-zero angle relative to a portion of the posterior flap that extends directly from the main body. In some examples, having the portions of the first anterior flap and the second anterior flap that overlap each other increases a bending resistance of the first anterior flap and the second anterior flap in combination as compared to the first anterior flap and the second anterior flap individually. Having the portions of the first anterior flap and the second anterior flap as separate members can configure the prosthetic tricuspid valve to have a pacemaker lead pass through the prosthetic tricuspid valve between the first and second anterior flaps. The prosthetic tricuspid valve may also include one or more additional anterior flaps extending laterally from the end of the main body in the same direction as the first and second anterior flaps. The prosthetic tricuspid valve may also include two or more posterior flaps extending laterally from the end of the main body in an opposite direction as the first and second anterior flaps. Having the portions of the first posterior flap and the second posterior flap as separate members can configure the prosthetic tricuspid valve to have a pacemaker lead pass through the prosthetic tricuspid valve between the first and second posterior flaps. In some embodiments, a transverse cross-section of the main body has an oval shaped outer profile that defines a major diameter and a minor diameter. The minor diameter is shorter than the major diameter. The occluder may have a circular cross-sectional shape, and the anterior and posterior flaps may extend transversely to the major diameter. The prosthetic heart valve may also include a leaflet engagement member extending from the main body, a portion of the leaflet engagement member extending toward the inflow end portion and terminating at a free end. The leaflet engagement member may extend in the second direction. The posterior flap may extend farther away from the main body than the leaflet engagement member.

BRIEF DESCRIPTION OF FIGURES

FIG. 12 schematically illustrates the prosthetic heart valve of FIG. 11 engaged with the native tricuspid valve annulus and RVOT of FIG. 10.

FIG. 13 schematically illustrates a cross-section view taken along the cutting plane 13-13 of FIG. 12 and including the anterior flaps of the prosthetic heart valve and the RVOT.

DETAILED DESCRIPTION

Some embodiments described herein include a prosthetic heart valve that may be delivered to a targeted native heart valve site via one or more delivery catheters. In some embodiments, a prosthetic heart valve includes structural features that securely anchor the prosthetic heart valve to the anatomy at the site of the native heart valve. Such structural features can provide robust migration resistance during diastole and systole. In addition, the prosthetic heart valves can include structural features that improve sealing between the prosthetic valve and native valve anatomy to mitigate paravalvular leakage. In particular implementations, the prosthetic heart valves occupy a small delivery profile, thereby facilitating a smaller delivery catheter system for advancement to the heart. Some catheter-based prosthetic heart valve deployment systems can include a curved inner catheter to facilitate deployment of the prosthetic heart valve to a native tricuspid valve site via a superior vena cava or inferior vena cava.

Figure 1:
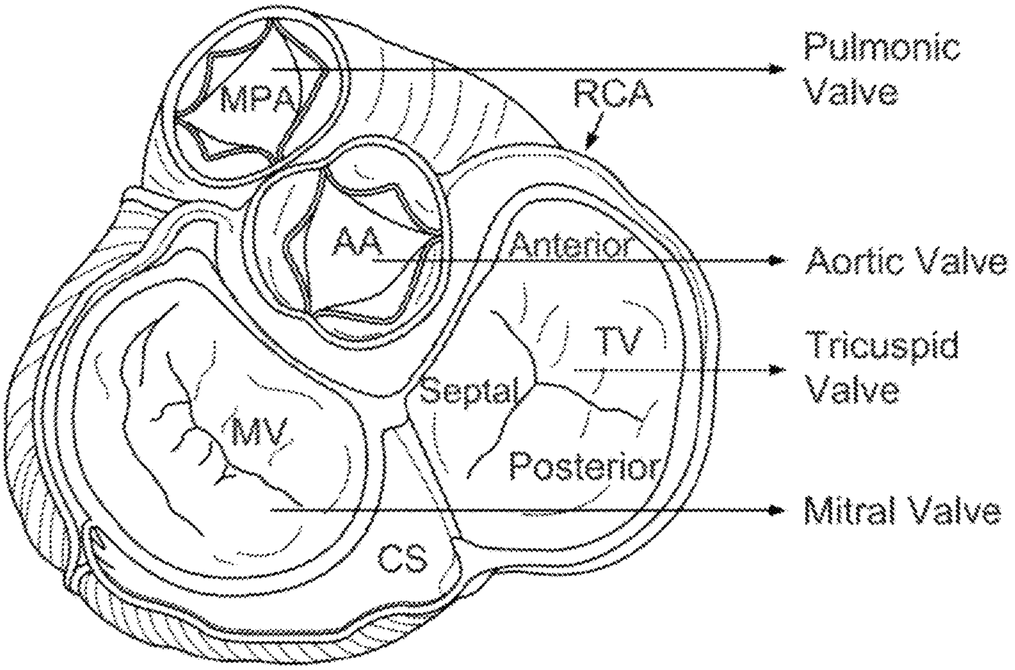
FIG. 1 shows a sectional view of a human heart including four heart valves (mitral valve, tricuspid valve, aortic valve, and pulmonary valve) that allow blood flow through specific pathways. The mitral and tricuspid valve are arranged to prevent backflow of blood into left atrium and right atrium respectively when the left and right ventricle contract respectively.
Figure 2:
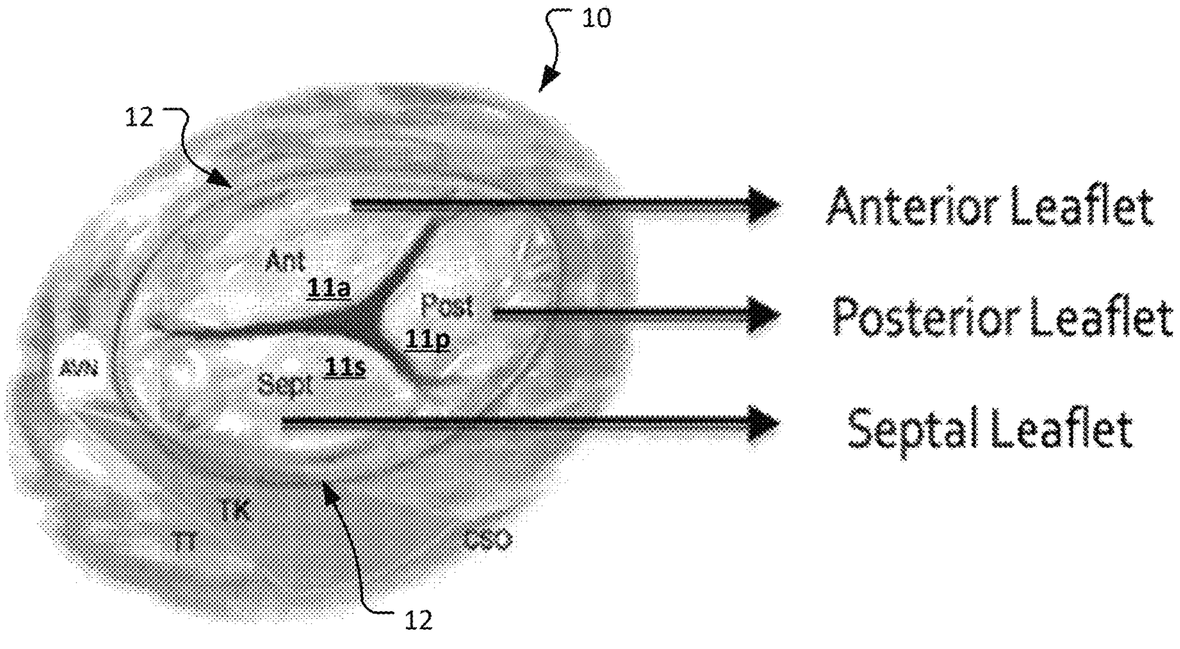
FIG. 2 shows a top view of the tricuspid valve of FIG. 1 and including three native leaflets: anterior, posterior and septal.

Referring to FIG. 1, certain aspects of the concepts described herein regarding the heart valve replacement systems can be implemented in prosthetic valve designs that are intended for use at any of the four heart valves that allow blood flow through a specific pathway: mitral valve, tricuspid valve, aortic valve and the pulmonary valve. FIG. 2 depicts, for example, a targeted site at a tricuspid valve of the heart. The tricuspid valve 10 includes an anterior leaflet 11*a*, a posterior leaflet 11*p*, and a septal leaflet 11*s*, and an annulus 12. In some circumstances, the tricuspid valve 10 may undergo stenosis or anatomical changes that cause tricuspid regurgitation, such as instances in which the distance between the anterio-septal commissure and the anterio-posterior commissure of the native tricuspid valve increases with the progression of a diseased state due to dilation of the annulus 12 of the tricuspid valve 10.

Figure 3:
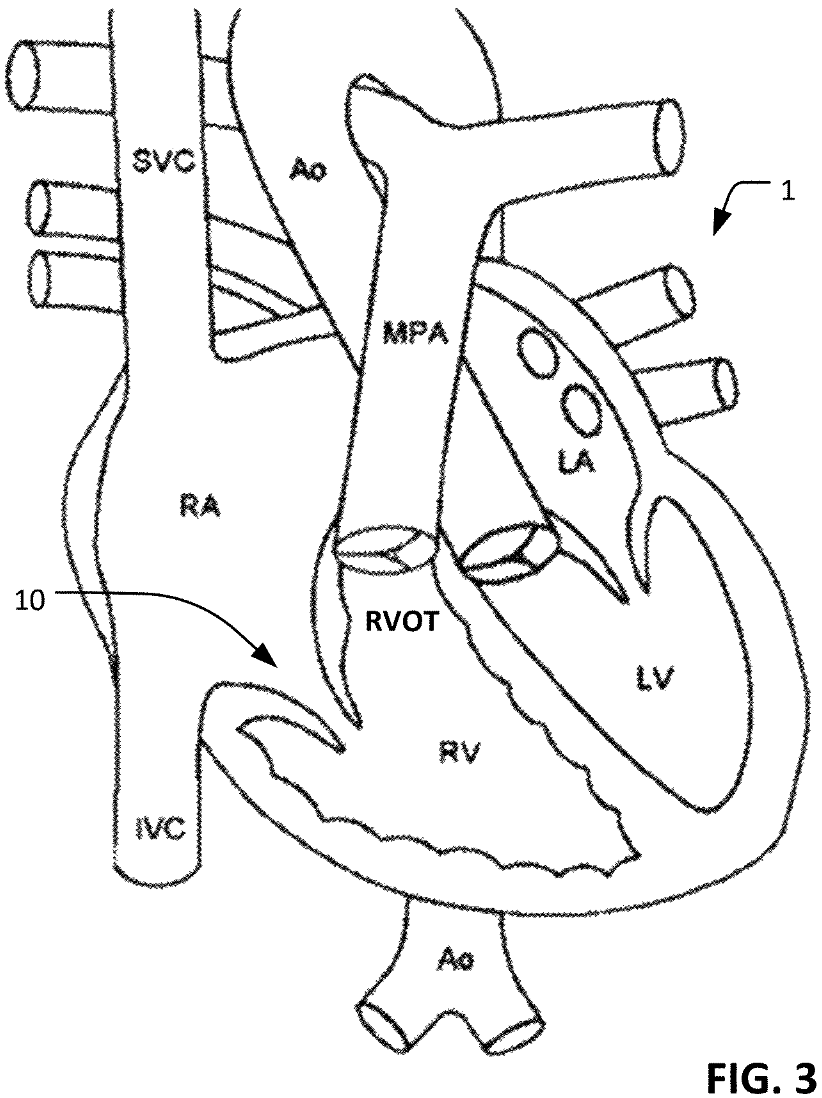
FIG. 3 shows another sectional view of a human heart including the four chambers (right atrium, right ventricle, left atrium, and left ventricle) and major conduits that deliver blood to the heart and transport blood away from the heart.

FIG. 3 illustrates a longitudinal sectional view of a human heart 1 that shows the four chambers (right atrium, right ventricle, left atrium, and left ventricle) and the major conduits that deliver blood to the heart 1 and transport blood away from the heart 1. The tricuspid valve 10 is located between the right atrium and the right ventricle. Blood enters the right atrium from the superior vena cava and the inferior vena cava. Blood flows from the right atrium to the right ventricle through the tricuspid valve 10. The blood exits the right ventricle and enters the main pulmonary artery ("MPA") via the RVOT that is adjacent to the tricuspid valve 10.

Figure 5:
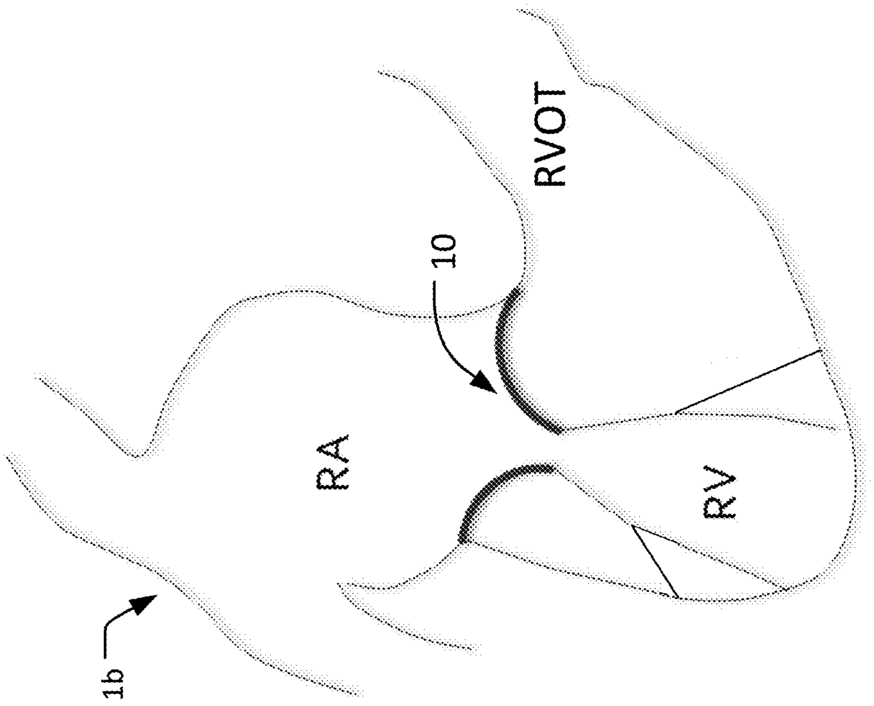
FIG. 5 shows another schematic view of the right side of the heart of FIG. 3, including the RA, RV, and RVOT, in accordance with some native anatomies.
Figure 4:
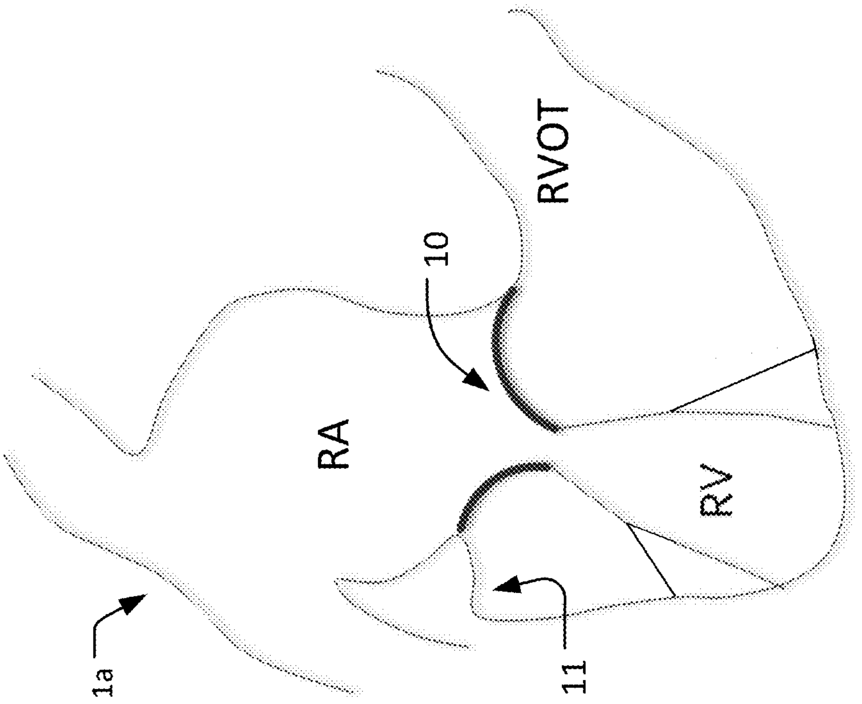
FIG. 4 shows a schematic view of the right side of the heart of FIG. 3, including the right atrium ("RA"), right ventricle ("RV"), and right ventricle outflow tract ("RVOT"), in accordance with some native anatomies.

FIGS. 4 and 5 schematically illustrate the right side of the heart 1, including the right atrium, right ventricle, and tricuspid valve 10 therebetween. Naturally, there is anatomical variability among the human population. FIGS. 4 and 5 depict some of the anatomical variability. In particular, FIG. 4 shows a heart 1*a* that includes the presence of a posterior shelf 11. In contrast, FIG. 5 shows a heart 1*b* with a lack of any such posterior shelf. Some human hearts (such as the heart 1*a*) have a posterior shelf 11, but some human hearts (such as the heart 1*b*) do not have a distinct posterior shelf. The prosthetic tricuspid valves disclosed herein are designed to be implantable in the native tricuspid valve 10 of both types of anatomies (e.g., both the heart 1*a* with the posterior shelf 11, and the heart 1*b* without the posterior shelf).

The posterior shelf 11, when present, provides an anatomical structure that can be used advantageously for the anchorage of a prosthetic tricuspid valve (as described further herein). When no such posterior shelf is present (e.g., as shown in FIG. 5), robust anchorage of a prosthetic tricuspid valve at the site of the native tricuspid valve 10 is more challenging. Nevertheless, and as described in U.S. patent application Ser. No. 17/747,507 filed on May 18, 2022) which is hereby incorporated by reference in its entirety and for all purposes), the prosthetic tricuspid valves described herein can be successfully used in such a case.

Figure 6:
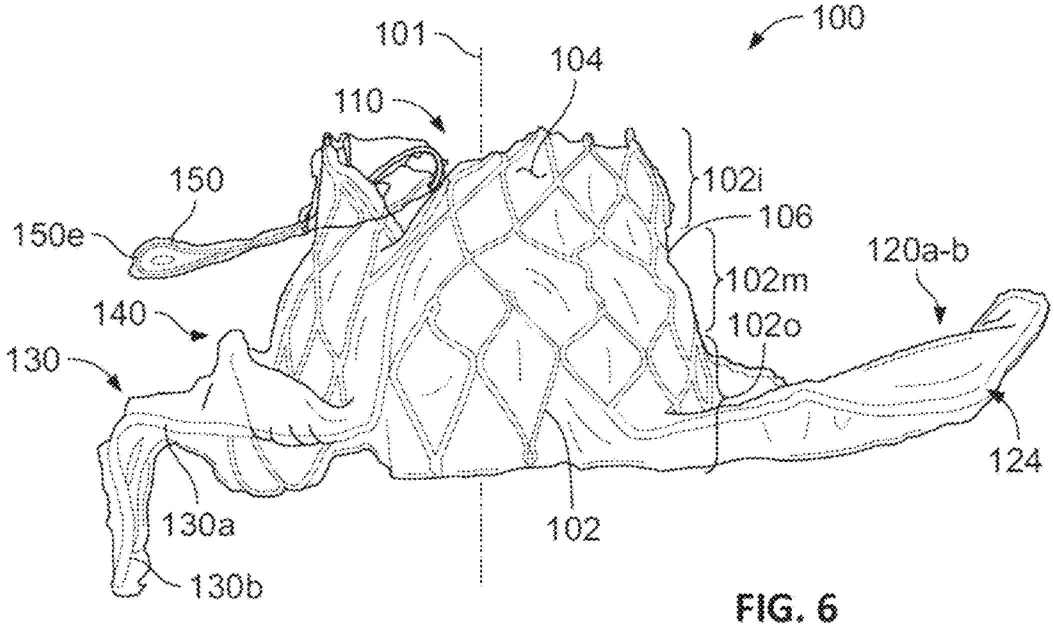
FIG. 6 shows a side view of an example prosthetic heart valve in accordance with some embodiments described herein.
Figure 7:
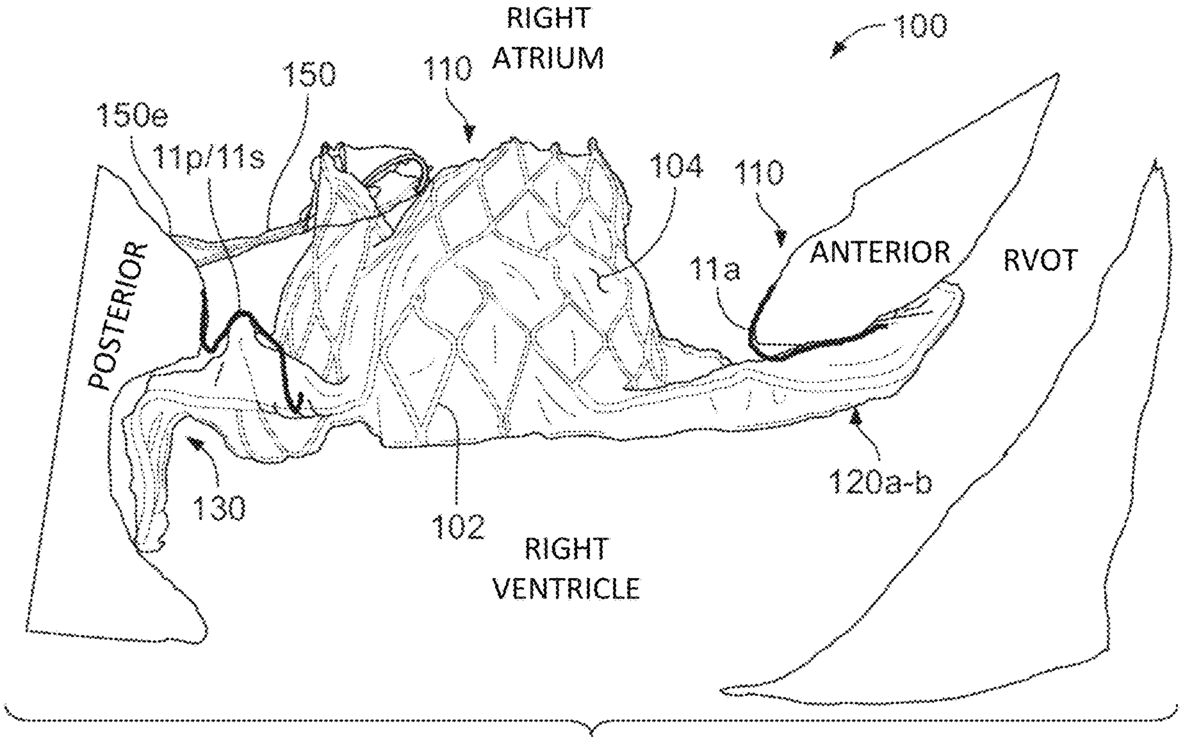
FIG. 7 shows a side view of the prosthetic heart valve of FIG. 6 engaged within a native tricuspid valve.
Figure 8:
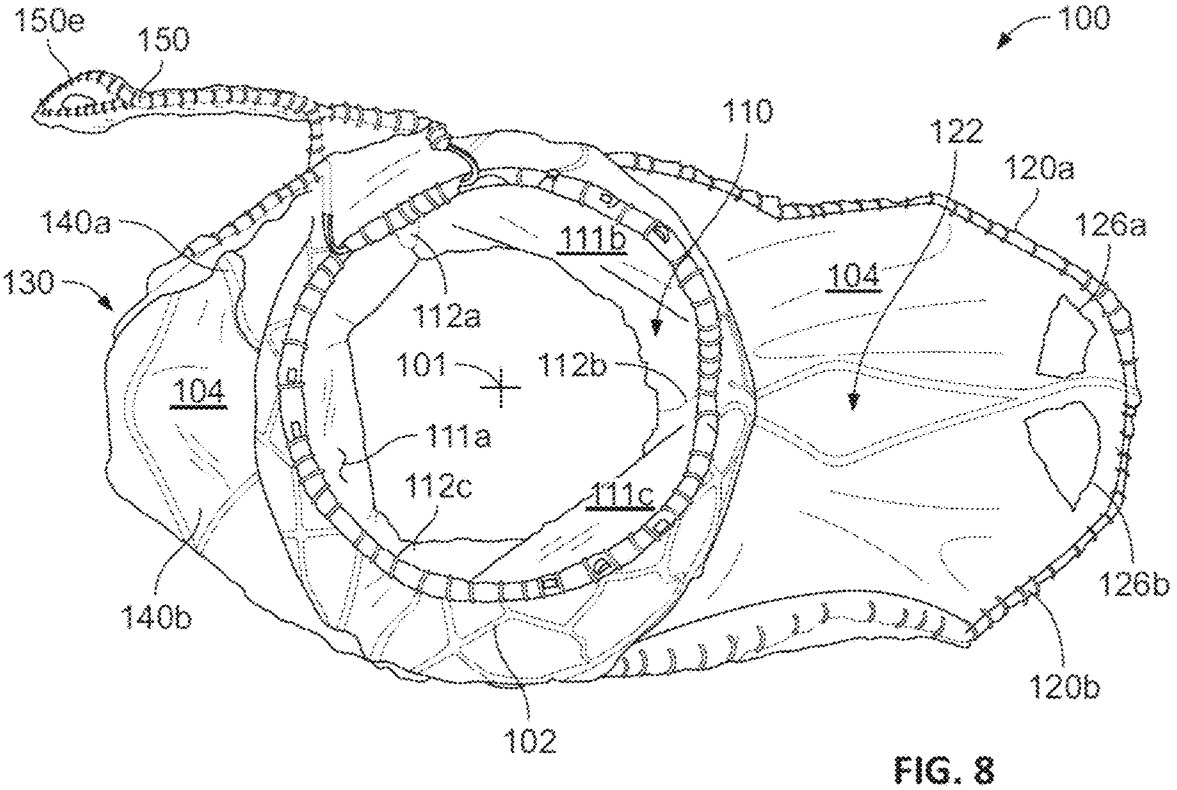
FIG. 8 shows a top view of the prosthetic heart valve of FIG. 6.

FIGS. 6-8 illustrate an example prosthetic tricuspid valve 100 (or simply "valve 100") in accordance with some example embodiments of this disclosure. The valve 100 includes a frame 102 and a covering 104 attached to the frame 102. FIG. 7 shows the valve 100 engaged with a native tricuspid valve 10 between the right atrium and the right ventricle.

The frame 102 comprises a cellular structure that provides mechanical support for the shape and structures of the valve 100. In some embodiments, the frame 102 is made from nitinol (NiTi), stainless steel, cobalt chromium, MP35N, titanium, polymeric materials, other biocompatible materials, or any combination thereof. Some or all parts of the frame 102 may be covered by the covering 104. The frame 102 can be made of a laser cut, expanded, and shape-set material in some embodiments. The frame 102 is self-expanding in some embodiments. In some embodiments, the precursor material is tubular NiTi, a NiTi sheet, or other suitable types of precursor materials.

The covering 104 may made of a biocompatible polymer material (e.g., expanded polytetrafluoroethylene (ePTFE), UHMWPE (ultra-high molecular weight polyethylene), nylon, polyester (e.g., DACRON), or another synthetic material), natural tissues (e.g., bovine, porcine, ovine, or equine pericardium), or any combination thereof. The covering 104 can be attached to the frame 102 by suturing, using clips, adhesives, and/or any other suitable attachment process.

The valve 100 includes a main body 106. The main body 106 includes an occluder 110 (e.g., a one-way valve) that defines a central axis 101. The occluder 110 has flexible leaflets 111*a*, 111*b*, and 111*c* (collectively 111*a-c*) that cause the occluder 110 to function as a one-way valve (in a manner like a native tricuspid valve). The occluder 110 defines a circular inlet where the edges of leaflets 111*a-c* are attached to the frame 102. Other side edges of the leaflets 111*a-c* are attached to posts 112*a*, 112*b*, and 112*c* of the frame 102. The leaflets 111*a-c* also have distal free edges that are coaptable with each other to facilitate the opening and sealing of the occluder 110.

The main body 106 of the valve 100 includes an inflow end portion 102*i*, a mid-body portion 102*m*, and an outflow end portion 1020. The inflow end portion 102*i* includes a series of arch shapes in the frame 102, circumscribing the axis 101 of the occluder 110. The occluder leaflets 111*a-c* allow blood to directionally flow through the occluder 110 from the inflow end portion 102*i* to the outflow end portion 1020. The leaflets 111*a-c* of the occluder 110 close against each other (e.g., coapt) to prevent blood flow in the other direction (to prevent blood flow from the outflow end portion 102*o* to the inflow end portion 102*i*).

The embodiments of the valve 100 depicted in this disclosure employ three occluder leaflets 111*a-c*, which is referred to as tri-leaflet occluder. The occluder 110 of the valve 100 can optionally employ configurations other than a tri-leaflet occluder. For example, bi-leaflet, quad-leaflet, or mechanical valve constructs can be used in some embodiments. In particular implementations described herein, the flexible leaflets 111*a-c* are made of natural tissues such as porcine or bovine or equine or ovine pericardium. In such embodiments, the tissues are chemically cross-linked using glutaraldehyde or formaldehyde, or other aldehydes commonly used as crosslinking agents. In other embodiments, the flexible leaflets 111*a-c* are made of polymers such as polyurethane, polyester (DACRON) or expanded polytetrafluoroethylene (ePTFE). In some embodiments, the flexible leaflets 111*a-c* are attached to structural frame 102 using sutures that could be made of materials including but not limited to UHMWPE, nylon, or polyester (e.g., DACRON).

The valve 100 also includes a first anterior flap 120*a* (or septal anterior flap 120*a*), a second anterior flap 120*b* (or lateral anterior flap 120*b*), and at least one posterior flap 130. The frame 102 and the covering 104 combine to form the anterior flaps 120*a-b* and the posterior flap 130. The frame 102 provides the structure of the anterior flaps 120*a-b* and the posterior flap 130, and the covering 104 provides occlusion. While the depicted embodiment includes two anterior flaps 120*a-b*, in some embodiments one, three, four, or more than four anterior flaps can be included. While the depicted embodiment includes a single posterior flap 130, in some embodiments two, three, four, or more than four posterior flaps can be included. For instance, FIG. 31 refers to an embodiment with two posterior flaps 330*a* and 330*b*.

The anterior flaps 120*a-b* and the posterior flap 130 extend away from the outflow end portion 1020 of the main body 106 in opposite directions away from the axis 101. That is, the posterior flap 130 extends directionally opposite from the extension direction of the first and second anterior flaps 120*a-b*. In some embodiments, the posterior flap 130 extends 180° opposite from the extension direction of the first and second anterior flaps 120*a-b*. In particular embodiments, the anterior flaps 120*a-b* and the posterior flap 130 extend away from the outflow end portion 102*o* of the main body 106 transverse to the axis 101 of the occluder 110.

In the depicted embodiment, the first anterior flap 120*a* and the second anterior flap 120*b* each include a mid-body portion 124 (FIG. 6) that is bent at an angle so as to direct terminal end portions of the anterior flaps 120*a-b* toward the inlet end of the main body 106. In some embodiments, the anterior flaps 120*a-b* initially extend away from the main body 106 substantially perpendicularly (e.g., within about 80° to 100°) to the central axis 101. Then, at the mid-body portion 124, the anterior flaps 120*a-b* have a bend that defines an angle θ in a range of between 20° to 60°, or 30° to 60°, or 30° to 70°, or 40° to 60°, or 40° to 70°, or 40° to 50°, without limitation.

The bends in the mid-body 106 of the anterior flaps 120*a-b* can allow the anterior flaps 120*a-b* to conform to the contours of the wall that defines the RVOT (as shown in FIG. 7). Accordingly, the bent anterior flaps 120*a-b* can reduce the potential of the anterior flaps 120*a-b* to restrict blood flow through the RVOT in some cases.

As shown in FIG. 8, the depicted embodiment includes an opening 126*a* that is defined by the covering 104 located at a terminal end portion of the first anterior flap 120*a*. Additionally, the covering 104 on the second anterior flap 120*b* defines an opening 126*b* at a terminal end portion of the second anterior flap 120*b*.

The openings 126*a-b* in the end portions of the anterior flaps 120*a-b* allow blood to flow through the anterior flaps 120*a-b* (via the openings 126*a-b*). This can be beneficial because in some implementations the anterior flaps 120*a-b* extend into the RVOT. Accordingly, such openings 126*a-b* may in some cases reduce the potential of the anterior flaps 120*a-b* to restrict blood flow through the RVOT.

In the depicted embodiment, the posterior flap 130 includes a first portion 130*a* and a second portion 130*b* that are arranged at an angle in relation to each other. The first portion 130*a* extends away from the outflow end portion 102*o* of the main body 106 generally transverse to the axis 101 of the occluder 110. The second portion 130*b* of the posterior flap 130 extends from the first portion 130*a*. In the depicted embodiment, the second portion 130*b* extends generally parallel to the axis 101 of the occluder 110. The angle defined between the first portion 130*a* and the second portion 130*b* can be in a range of 80° to 100°, or 70° to 110°, or 60° to 120°, or 50° to 130°, or 40° to 140°, without limitation.

The first anterior flap 120*a* and the second anterior flap 120*b* each extend in the same direction, which is opposite of the direction that the posterior flap 130 extends. In the depicted embodiment, portions of the first anterior flap 120*a* and the second anterior flap 120*b* overlap each other. An advantage of having the two separate anterior flaps 120*a-b* (rather than a single larger anterior flap) is that the anterior flap portion of the valve 100 can be radially compressed to a smaller profile for transcatheter delivery by the virtue of having the two separate anterior flaps 120*a-b* (as compared to having a single larger anterior flap).

In some embodiments, as shown in FIG. 7, the first and second anterior flaps 120*a-b* extend into the RVOT and overlap one axially on top of the other. This arrangement is functionally akin to a cantilevered beam arrangement. With the first and second anterior flaps 120*a-b* overlapping on each other, the bending resistance of the first and second anterior flaps 120*a-b* is increased (as compared to a single flap or non-overlapping flaps). This arrangement enables an advantageous extent of rigidity, without having to use framework members that are larger in cross-section. That is, the overlapping arrangement of the first and second anterior flaps 120*a-b* allow for the use of smaller framework members, which in turn importantly allows for a smaller collapsed delivery size (diameter). In other words, overlapping arrangement of the first and second anterior flaps 120*a-b* provides a support structure that is thicker without having to use a material with higher wall thickness (from which the framework is created); ultimately providing the bending stiffness or rigidity that keeps the valve 100 stable when RV pressure acts on the valve 100.

Figure 16:
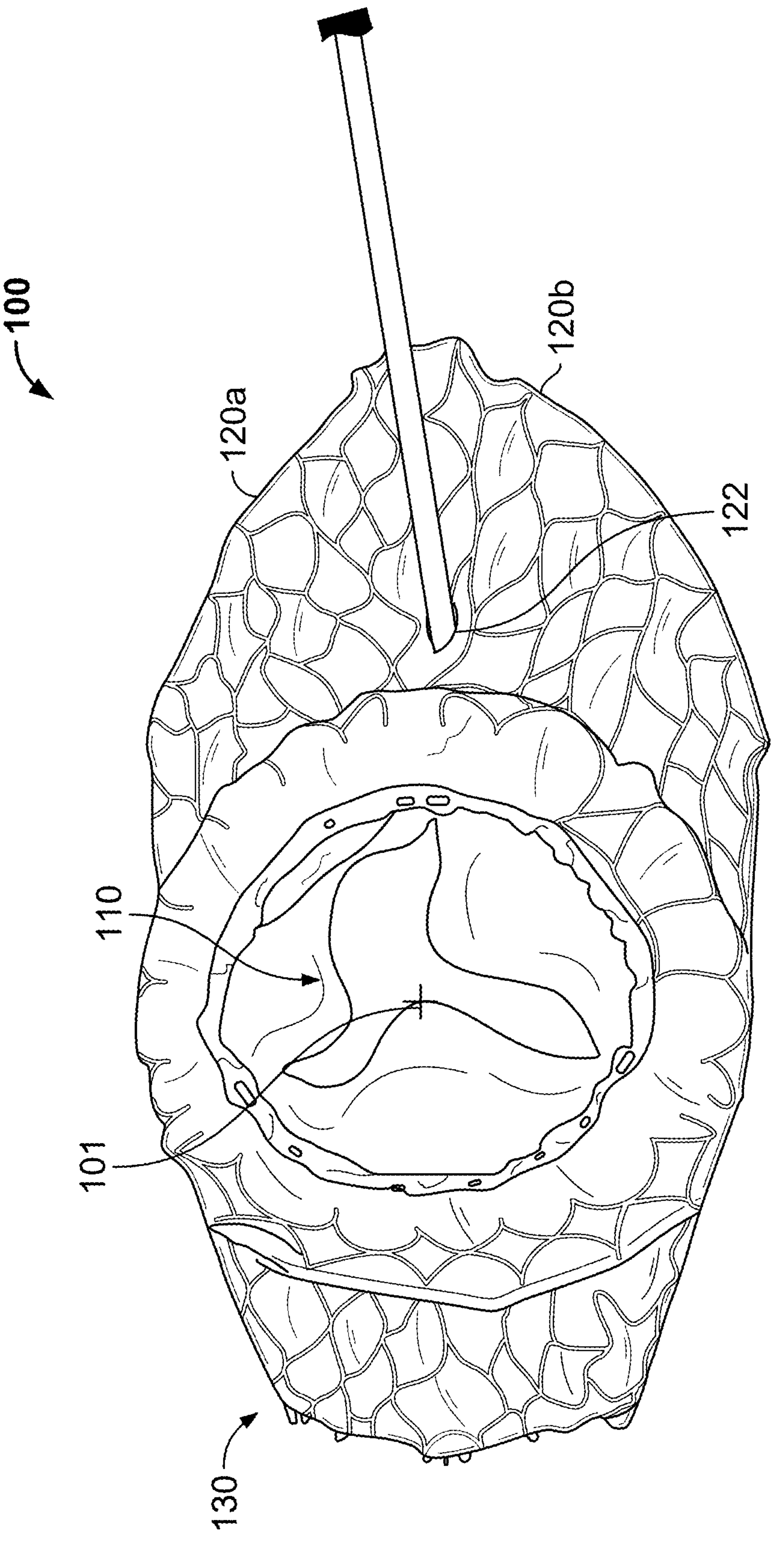
FIG. 16 shows a top view of some prosthetic heart valves described herein.

In the depicted embodiment, an open passage 122 (e.g., see FIG. 16) is defined between the first anterior flap 120*a* and the second anterior flap 120*b*. The open passage 122 can be used, for example, for passing a pacemaker lead through the valve 100, without disturbing the functioning of the occluder 110. Accordingly, the valve 100 can facilitate the pass-through of the pacemaker lead while still providing sealing to prevent tricuspid valve regurgitation from the RV to the RA. In some cases, the pacemaker lead is pre-existing and the valve 100 is implanted subsequently (with the open passage 122 being used to receive the pacemaker lead). In other cases, the valve 100 can be pre-existing and the pacemaker lead can be subsequently passed through the open passage 122. This could take place both during the same implant procedure, or as a subsequent procedure.

Figure 31:
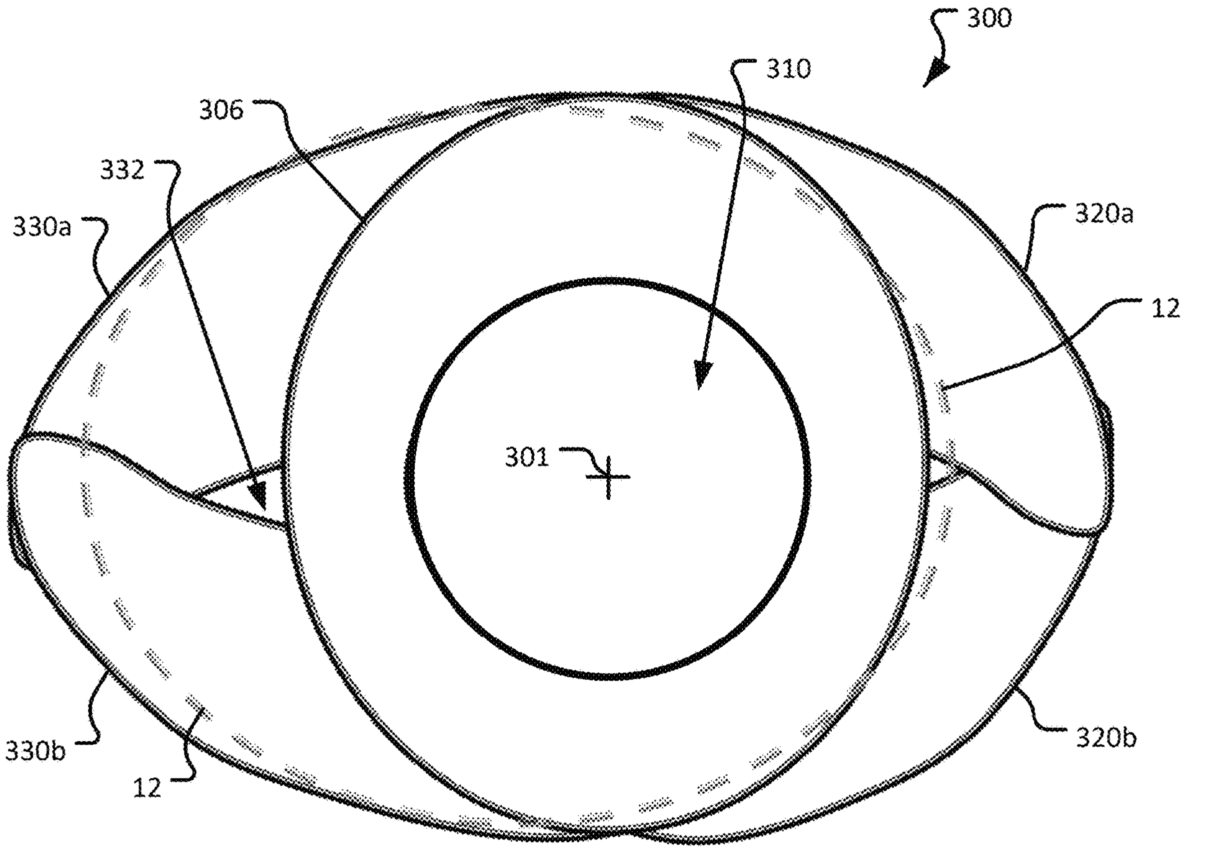
FIG. 31 schematically shows a top view of another example prosthetic heart valve in accordance with some embodiments described herein.

FIG. 31 illustrates another example prosthetic valve 300. The valve 300 defines an open passage 332 between the posterior flaps 330*a* and 330*b* that can be used, for example, for passing a pacemaker lead through the valve 300, without disturbing the functioning of the occluder 310. In some cases, the pacemaker lead is pre-existing and the valve 300 is implanted subsequently (with the open passage 322 being used to receive the pacemaker lead). In other cases, the valve 300 can be pre-existing and the pacemaker lead can be subsequently passed through the open passage 322.

Still referring to FIGS. 6-8, the valve 100 also includes one or more leaflet engagement members 140. In the depicted embodiment, the valve 100 includes two leaflet engagement members: a first leaflet engagement member 140*a* and a second engagement member 140*b*. In the depicted embodiment, the leaflet engagement members 140*a-b* extend from the outflow end portion 102*o* of the main body 106. In some embodiments, the leaflet engagement members 140*a-b* extend from the mid-body portion 102*m* of the main body 106.

The leaflet engagement members 140*a-b* extend from the frame 102 and bend toward the inflow end portion 102*i* of the main body 106. In other words, a portion of each leaflet engagement member 140*a-b* extends toward the inflow end portion 102*i* of the main body 106. A space, groove, or slot is defined between the leaflet engagement members 140*a-b* and the outer surface of the frame 102 (with the covering 104 being present on the frame 102 and leaflet engagement members 140*a-b*). As described further below, the space, groove, or slot receives and mechanically captures/holds a portion of a native leaflet (e.g., the posterior leaflet 11*p* and/or the septal leaflet 11*s*) to provide migration resistance for the valve 100.

In the depicted embodiment, the leaflet engagement members 140*a-b* extend from the frame 102 of the main body 106 in the same direction as the posterior flap 130. The posterior flap 130 extends away from the main body 106 farther than the leaflet engagement members 140*a-b*. Various other arrangements of the leaflet engagement members 140*a-b* and the posterior flap 130 are also envisioned and within the scope of this disclosure.

The leaflet engagement members 140*a-b* may be U-shaped wire loops, as in the depicted embodiment. The wire loops that make up the leaflet engagement members 140*a-b* can be continuous with the wire members of the frame 102.

In the depicted embodiment, the leaflet engagement members 140*a-b* terminate at free ends. Accordingly, the leaflet engagement members 140*a-b* point toward the inflow end portion 102*i* of the main body 106, with the free ends of the leaflet engagement members 140*a-b* being the closest to the inflow end portion 102*i*. This arrangement defines the space, groove, or slot receives and mechanically captures/holds a portion of a native leaflet to provide migration resistance for the valve 100.

The depicted embodiment of the valve 100 includes an optional posterior arm 150. The posterior arm 150 comprises a wire member (e.g., an elongated loop) that extends from the frame 102 and includes a free end 150*e* (which can also be said to be located at a distal end portion of the posterior arm 150). In some embodiments, the posterior arm 150 is a wire member that is constructed unitarily with wire members of the frame 120. Hence, it can be said that the posterior arm 150 is a portion of the frame 120. In the depicted embodiment, the covering 104 is attached to the posterior arm 150, including the free end 150*e*.

In the depicted embodiment, the posterior arm 150 extends from the inflow end portion 102*i* of the frame 102. The posterior arm 150 extends in a direction that is the same as, or that is generally (e.g., +/−20°) parallel to, the direction in which the posterior flap 130 extends. In some embodiments, the posterior arm 150 extends from the mid-body portion 102*m* of the frame 102. The location of the free end 150*e* is within a transverse plane (e.g., taken perpendicular to the axis 101) that intersects the mid-body portion 102*m* of the frame 102 or the inflow end portion 102*i* of the frame 102.

The posterior arm 150 provides additional anchorage and migration resistance for the valve 100. As depicted in FIG. 7, the free end 150*e* of the posterior arm 150 abuts against an anatomical structure when the valve 100 is engaged in a native tricuspid valve 10. In some cases, the free end 150*e* of the posterior arm 150 abuts against an interior wall of an inferior vena cava, or coronary sinus, or the right atrium, or another anatomical structure. Where it abuts can be largely a function of the variable anatomy from patient to patient. The migration resistance provided by the posterior arm 150 can be particularly advantageous during diastole when the occluder 110 is open to allow blood flow from the right atrium to the right ventricle via the occluder 110.

Figure 9:
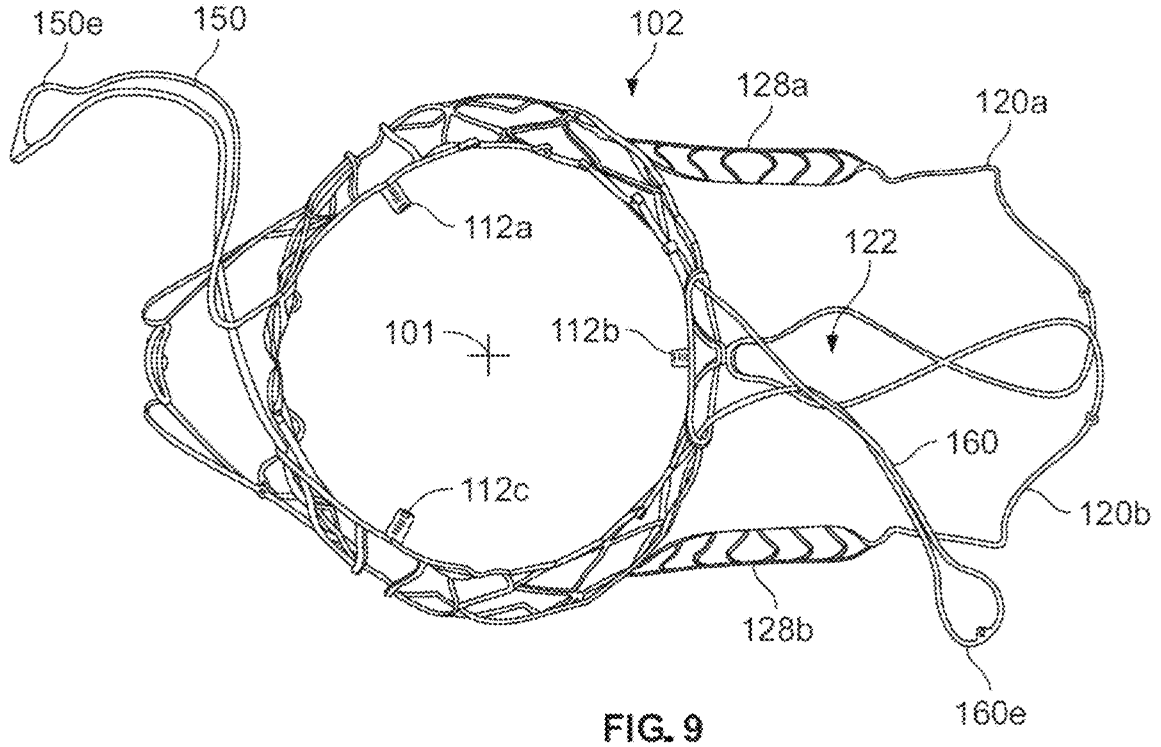
FIG. 9 shows a top view of a frame of another example prosthetic heart valve in accordance with some embodiments described herein.

Referring also to FIG. 9, in some embodiments the frame 102 can include an anterior arm 160. The anterior arm 160 may also be covered similarly to the posterior arm 150. The anterior arm 160 comprises a wire member (e.g., an elongated loop) that extends from the frame 102 and includes a free end 160*e* (which can also be said to be located at a distal end portion of the posterior arm 160). In some embodiments, the anterior arm 160 is a wire member that is constructed unitarily with wire members of the frame 120. Hence, it can be said that the anterior arm 160 is a portion of the frame 120. In the depicted embodiment, the covering 104 is attached to the anterior arm 160, including the free end 160*e*.

In the depicted embodiment, the anterior arm 160 extends from the inflow end portion 102*i* of the frame 102. The anterior arm 160 extends in an anterior direction away from the axis 101 (e.g., a direction that is generally the same as the direction in which the anterior flaps 120*a-b* extend). In some embodiments, the anterior arm 160 extends from the mid-body portion 102*m* of the frame 102.

The location of the free end 160*e* is within a transverse plane (e.g., taken perpendicular to the axis 101) that intersects the mid-body portion 102*m* of the frame 102 or the inflow end portion 102*i* of the frame 102.

The anterior arm 160 provides additional anchorage and migration resistance for the valve 100. The free end 160*e* of the anterior arm 160 abuts against an anatomical structure when the valve 100 is engaged in a native tricuspid valve 10. In some cases, the free end 160*e* of the anterior arm 160 abuts against an interior wall of a right atrial appendage or another anatomical structure. Where the anterior arm 160 lands relative to the anatomy can vary based on patient to patient variability. The migration resistance provided by the anterior arm 160 can be particularly advantageous during diastole when the occluder 110 is open to allow blood flow from the right atrium to the right ventricle via the occluder 110.

Some embodiments of the valve 100 include the posterior arm 150, but not the anterior arm 160. Other embodiments of the valve 100 include the anterior arm 160, but not the posterior arm 150. Still other embodiments of the valve 100 include both the posterior arm 150 and the anterior arm 160.

Figure 10:
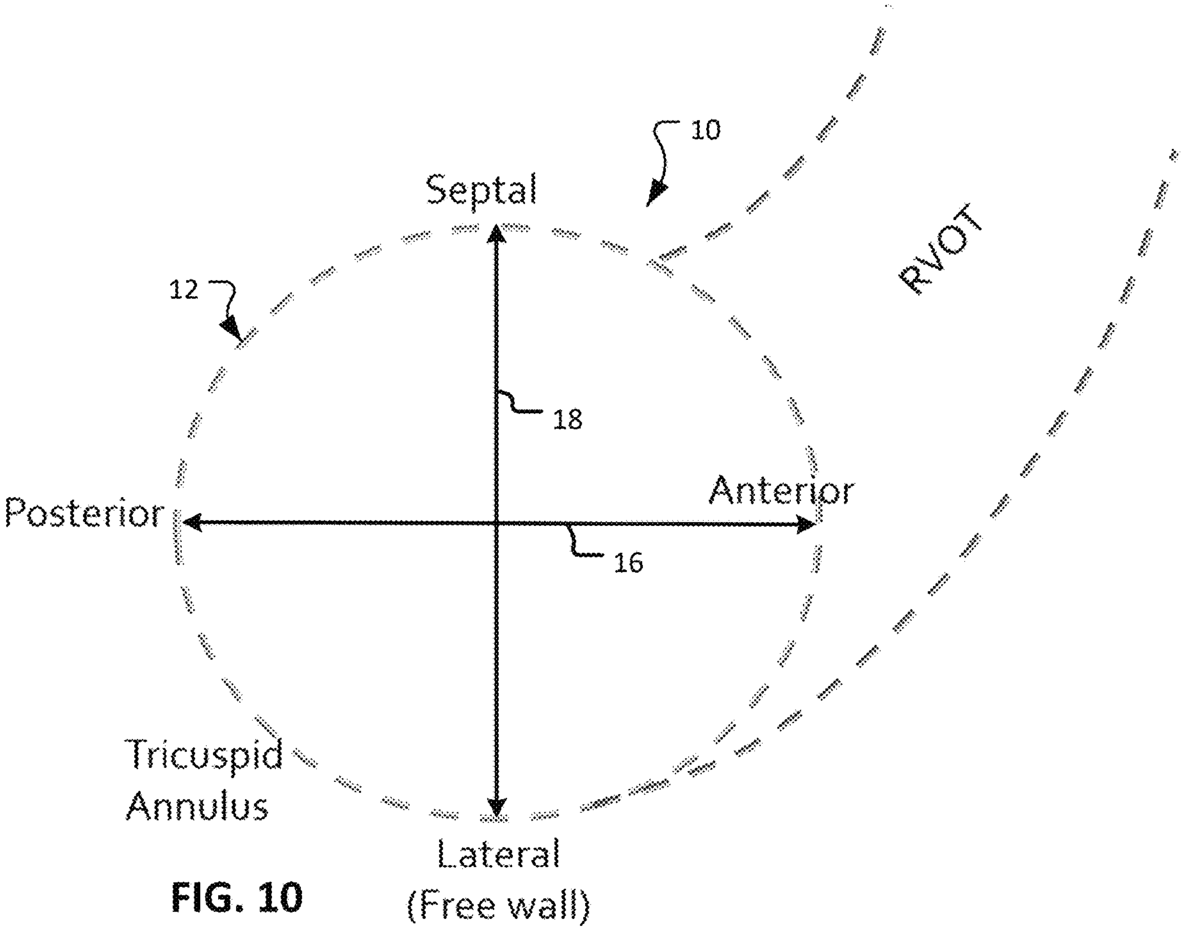
FIG. 10 schematically illustrates a transverse plane view of a native tricuspid valve annulus and RVOT.

FIG. 10 schematically illustrates a transverse plane view of a native tricuspid valve 10. The native tricuspid valve 10 includes the annulus 12. The RVOT extends away from the native tricuspid valve 10 along an arcuate path.

Figure 11:
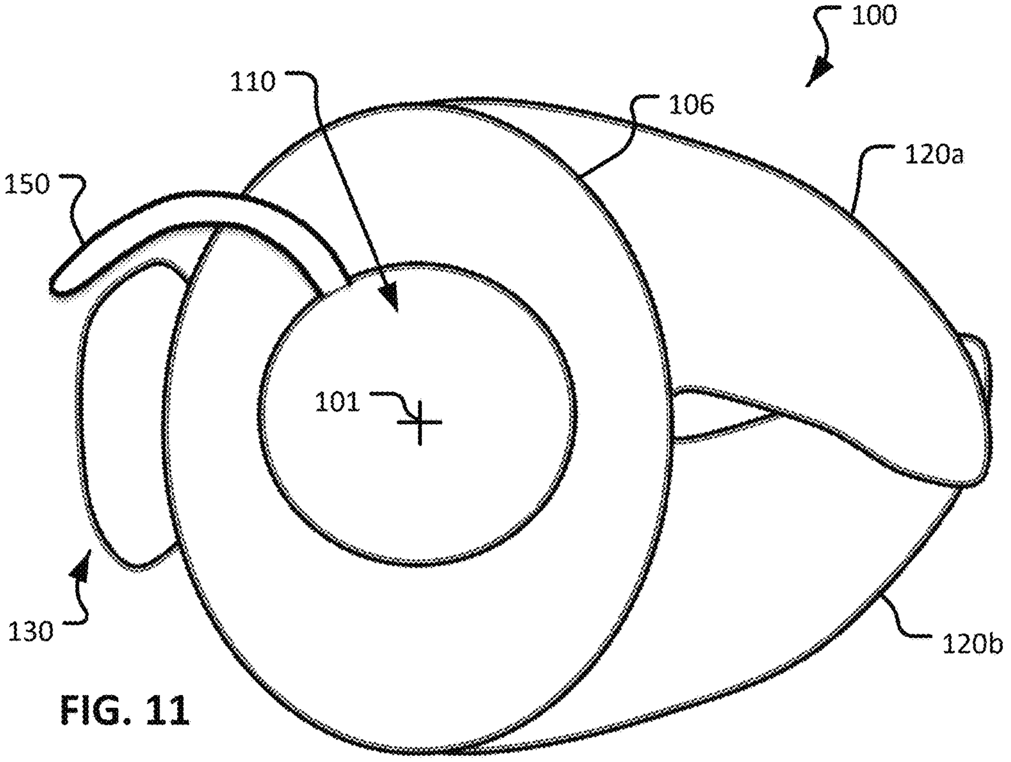
FIG. 11 schematically illustrates a top view of the prosthetic heart valve of FIG. 6.

FIG. 11 schematically illustrates a top view of the valve 100. The valve 100 includes the main body 106, the occluder

110, the septal anterior flap 120*a*, the lateral anterior flap 120*b*, the posterior flap 130, and the posterior arm 150.

FIG. 12 schematically illustrates the valve 100 engaged in the anatomy of the native tricuspid valve 10 (that is also illustrated in FIG. 10). In this illustration, it can be seen how the septal anterior flap 120*a* and the lateral anterior flap 120*b* extend into the RVOT. Moreover, it can be seen that an edge of the lateral anterior flap 120*b* abuts against and extends along a lateral wall 14 of the RVOT.

FIG. 13 schematically illustrates a cross-sectional view of the RVOT and distal end portions of the anterior flaps 120*a-b*. This cross-sectional view is taken along the cutting plane 13-13 shown in FIG. 12. It can be seen that the edge of the lateral anterior flap 120*b* abuts against and engages with the anatomical topography of the lateral wall 14 of the RVOT. The interfacing relationship between the lateral anterior flap 120*b* and the lateral wall 14 of the RVOT provides anchorage and migration resistance of the valve 100 relative to the native tricuspid valve 10. For example, there is a frictional migration resistance aspect provided by the normal forces exerted by the edge of the lateral anterior flap 120*b* against the lateral wall 14 of the RVOT. In addition, in some embodiments there is supplementary migration resistance provided because the edge of the lateral anterior flap 120*b* can seat against certain anatomical topographical features of the lateral wall 14 of the RVOT. In such a case, the lateral wall 14 physically supports the lateral anterior flap 120*b* and resists movement of the valve 10 relative to the anatomy of the native tricuspid valve 10 and RVOT. The interfacing relationship between the lateral anterior flap 120*b* and the lateral wall 14 of the RVOT provides anchorage and migration resistance of the valve 100 relative to the native tricuspid valve 10 that is particularly beneficial during diastole when the occluder 110 is open to allow blood flow from the right atrium to the right ventricle via the occluder 110.

Referring again to FIG. 10, the shape of the annulus 12 of many tricuspid valves is not circular. Often, as depicted here, shape of the annulus 12 is oblong or ovoidal (oval shaped). That is, the distance between the posterior and anterior regions of the annulus 12 is longer than the distance between the septal and lateral regions of the annulus 12. Accordingly, it can be said that the annulus 12 defines a major diameter 16 between the posterior and anterior regions, and a minor diameter 18 between the septal and lateral regions of the annulus 12.

Also referring again to FIG. 12, in this embodiment of the valve 100, the main body 106 has an ovular outer cross-sectional shape. In contrast, the occluder 110 within the main body 106 has a circular cross-sectional shape. The oval shaped main body 106 of the valve 100 has a major diameter 108 and a minor diameter 109. The anterior flaps 120*a-b* and the posterior flap 130 extend from the main body 106 along a direction that is transverse to the major diameter 108 of the oval shaped main body 106. In some embodiments, the anterior flaps 120*a-b* and/or the posterior flap 130 extend from the main body 106 substantially orthogonally or perpendicularly (e.g., 90°+/−5°, 90°+/−10°, 90°+/−15°, or 90°+/−20°,) to the major diameter 108 of the oval shaped main body 106.

In some embodiments, as depicted in FIG. 12, the main body 106 is smaller than the full size/area of the annulus 12. Accordingly, the anterior flaps 120*a-b* can be used to fill up the internal area defined the annulus 12 that is not occupied by the main body 106. The occluder 110 occupies a circular cross-sectional area that is smaller than the cross-sectional area main body 106, which is adequate for the hemodynamics of the blood flow between the atrium and the ventricle. In some embodiments, the percentage of the internal area defined by the annulus 12 that is occupied by the main body 106 is about 50% (with the remaining about 50% of the area of the annulus 12 being covered by the anterior flaps 120*a-b*). In some embodiments, the percentage of the area of the annulus 12 that is occupied by the main body 106 is in a range of about 50% to 60%, or 55% to 65%, or 60%, to 70%, or 65% to 75%, or 70% to 80%, or 75% to 85%, or 60% to 80%, without limitation, with the anterior flaps 120*a-b* covering the remainder of the area of the annulus 12. In some embodiments, the anterior flaps 120*a-b* cover at least 50%, or at least 40%, or at least 30%, or at least 20%, or at least 10%, or at least 5% of the internal area defined by the annulus 12.

The fact that the anterior flaps 120*a-b* cover at least a portion of the area defined within the annulus 12 can be beneficial for additional reasons. For example, if, at some point in the future after the valve 100 has been implanted in the annulus 12, a pacemaker lead needs to be passed through the annulus 12, then a location on the anterior flaps 120*a-b* can be punctured to allow the pacemaker lead to pass through the anterior flaps 120*a-b*. The puncture can be at the open passage 122, or at another location of the anterior flaps 120*a-b*. The ability to pass a pacemaker lead through the anterior flaps 120*a-b* is advantageous because doing so does not affect the functionality of the occluder 110. This is advantage is made possible by the fact that the anterior flaps 120*a-b* cover at least a portion of the area of the annulus 12.

Since, as depicted in the example of FIG. 12, in some cases a portion of the oval shaped annulus 12 is covered by the anterior flaps 120*a-b*, the main body 106 need not be circular, and can be constructed to have various types of cross-sectional shapes. An oval shape (as shown) may be preferable in some cases, as it can be radially compressed well for fitting in a low-profile delivery catheter because it can have a smaller perimeter due to the minor diameter 109 of the main body 106 being shorter than the major diameter 108. If, for example, the main body 106 had a circular cross-sectional shape with a diameter equal to the major diameter 108, the main body 106 could not be radially crushed/compressed to as small of a size as the depicted oval shaped main body 106. Hence, a larger delivery sheath would be required if the main body 106 was circular (as compared to ovular as shown).

Interestingly, in the example depicted in FIG. 12, while both the annulus 12 of the tricuspid valve 10 and the main body 106 of the valve 100 are oblong or oval shaped, the orientations of their major and minor diameters are about 90° (e.g., 90°+/−10°) offset in relation to each other when the valve 100 is implanted in the tricuspid valve 10. That is, the major diameter 108 of the oval shaped main body 106 is substantially parallel (e.g., +/−10°) relative to the minor diameter 18 of the annulus 12. Moreover, the minor diameter 109 of the oval shaped main body 106 is substantially parallel (e.g., +/−10°) relative to the major diameter 16 of the annulus 12. These geometric relationships are beneficial because the annulus 12 is fully occluded by the valve 100 and the diameter of the radially compressed delivery configuration of the valve 100 can be reduced (as compared to having the main body 106 filling a larger area of the annulus 12).

Again, it is evident in FIG. 12 that the opening defined by the native annulus 12 is not completely filled by the main body 106. Instead, the laterally-extending first and second anterior flaps 120*a-b* help to cover and fluidly seal the native tricuspid valve opening which is not circular in this example (e.g., with the native valve opening being oblong, or irregularly shaped). In other words, in combination with the main body 106 of the valve 100, the first and second anterior flaps 120*a-b* (and the laterally-extending posterior anchoring flap 130 in some cases) help to cover and fluidly seal the native tricuspid valve opening which is not circular in some cases. In addition, terminal end portions of the first and second anterior flaps 120*a-b* extend into the RVOT to provide anchoring and migration resistance. Accordingly, the first and second anterior flaps 120*a-b* perform both sealing and anchorage.

In some cases, the shape of a patient's native annulus 12 is generally circular. In such a case, the valve 100 can still provide much of the benefits described above. For example, the main body 106 can still have an oblong or oval-shaped outer cross-sectional shape that occupies less than the full circular area of the native annulus 12 (with the first and second anterior flaps 120*a-b* occupying the remainder). In that case, the valve 100 is implanted in the native annulus 12 such that the central axis 101 of the occluder 110 is laterally offset (e.g., in the posterior direction) from the geometric center of the generally circular native annulus 12. In addition, the major diameter 108 of the main body 106 can be shorter than the diameter of the native annulus 12. For example, in some embodiments the length of the major diameter 108 of the main body 106 is about 60% to 80% of the diameter of the native annulus 12, or about 70% to 90% of the diameter of the native annulus 12, or about 80% to 95% of the diameter of the native annulus 12, without limitation.

Figure 14:
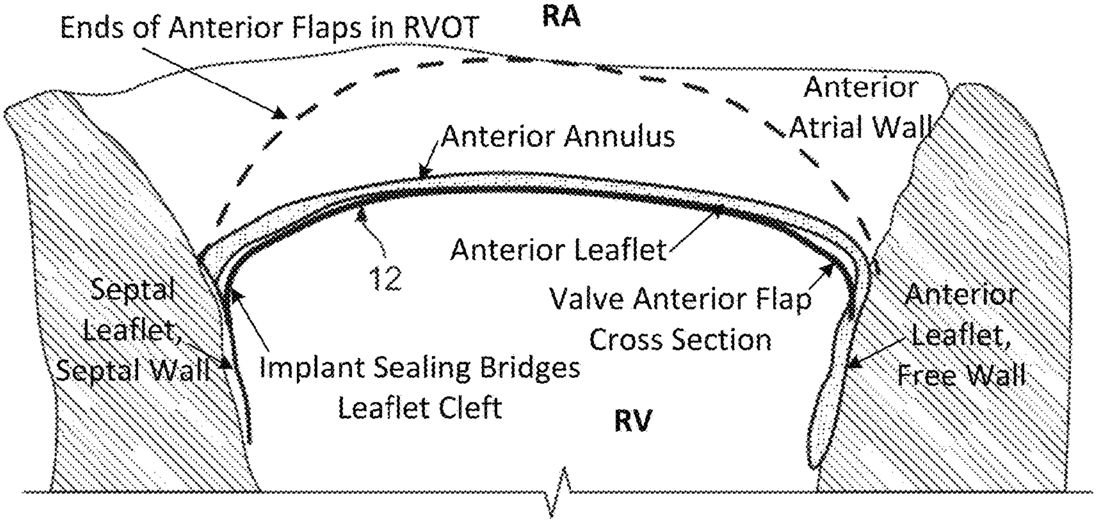
FIG. 14 schematically shows a longitudinal plane cross-section view of an anterior portion of a native tricuspid valve annulus and the anterior flaps of prosthetic heart valves described herein.

FIG. 14 illustrates a longitudinal plane cross-section view (e.g., approximately parallel to the central axis of the annulus 12) near an anterior portion of the native tricuspid valve annulus 12. This view is from the interface between the RVOT and the native tricuspid valve annulus 12, looking toward the right atrium and right ventricle. In this view, it can be seen that the anterior annulus 12 is curved.

Figure 15:
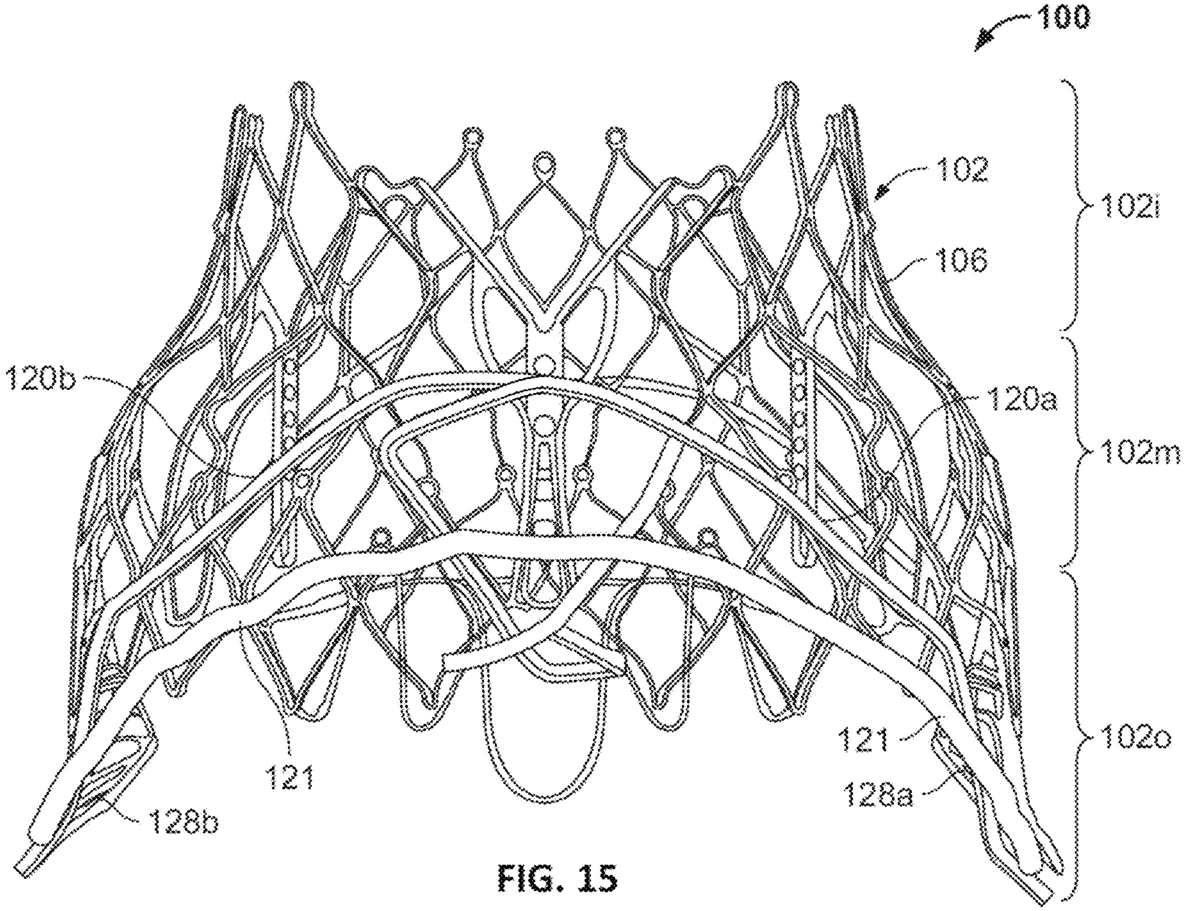
FIG. 15 is an anterior side view of the prosthetic heart valves described herein showing a cross-sectional shape of the anterior flaps.

FIG. 15 shows an anterior end view of the frame 102 of the valve 100 (without the covering 104 in this example). The first and second anterior flaps 120*a-b* are in the foreground in this view, and the main body 106 is in the background.

A heavy line 121 has been superimposed on FIG. 15 to represent the cross-sectional shape of the first and second anterior flaps 120*a-b* (when the covering 104 is attached to the frame 102). It can be seen that the cross-sectional shape of the first and second anterior flaps 120*a-b* (taken perpendicularly to the direction in which the first and second anterior flaps 120*a-b* extend from the main body 106) is curved or arcuate. The arc extends from the outflow end portion 102*o* of the frame 102 toward the inflow end portion 102*i*, with the middle of the arc being the closest point of the arc to the inflow end portion 102*i*.

The curved or arcuate cross-sectional shape of the first and second anterior flaps 120*a-b* is beneficial because, as described in reference to FIG. 14, the anterior portion of the native tricuspid valve annulus 12 with which the first and second anterior flaps 120*a-b* interface is also curved. Accordingly, a good sealing interface between the arced first and second anterior flaps 120*a-b* and the arced anterior portion of the native tricuspid valve annulus 12 is created by these complimentary curved shapes. This sealing arrangement between the arced first and second anterior flaps 120*a-b* and the native tricuspid valve annulus 12 can be beneficial for mitigating paravalvular leaks when the valve 100 is engaged with the native tricuspid valve 10.

As shown in FIG. 15, in the depicted embodiment the arcuate cross-sectional shape of the first and second anterior flaps 120*a-b* is at least partially facilitated by the configuration of frame portions 128*a* and 128*b* (also visible in FIG. 9). The frame portions 128*a* and 128*b* constitute interior parts of the outer edges of the first and second anterior flaps 120*a-b*. The frame portions 128*a* and 128*b* are arranged at a non-zero angle in relation to the central axis 101 so as to help define the arcuate cross-sectional shape of the first and second anterior flaps 120*a-b* that is represented by the heavy line 121. In some embodiments, the angle between the frame portions 128*a* and 128*b* and the central axis 101 is between 20° to 50°, or between 30° to 60°, or between 40° to 70°, without limitation. The frame portions 128*a* and 128*b* near the outer edges of the first and second anterior flaps 120*a-b* perform particularly advantageously to create good seals between the first and second anterior flaps 120*a-b* and the anterior portion of the native tricuspid valve annulus 12, because paravalvular leaks are particularly prone to occur in those edge areas.

Figure 17:
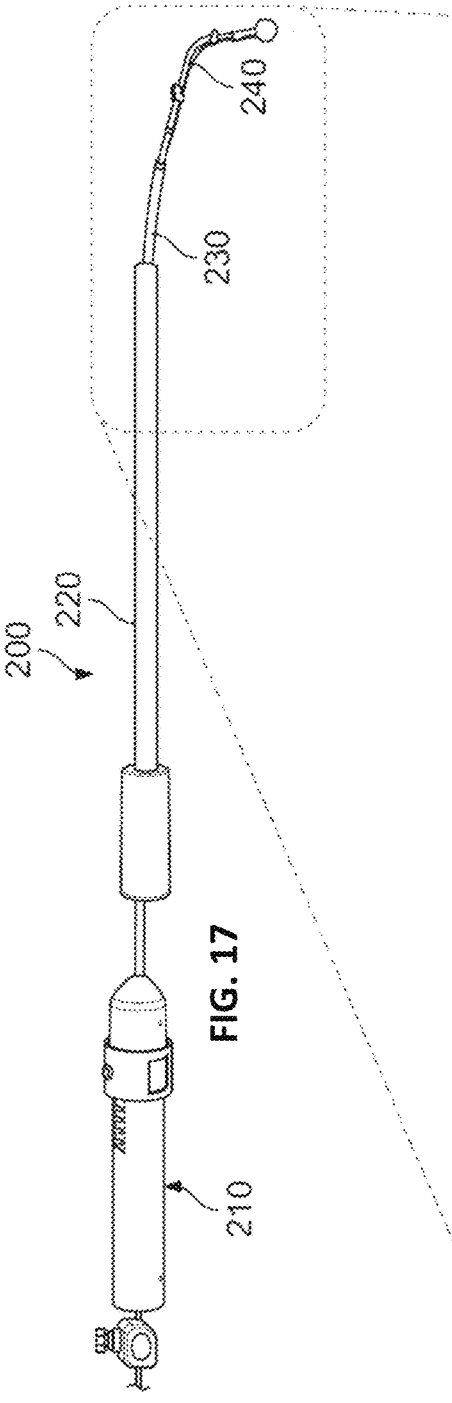
FIG. 17 shows a plan view of an example prosthetic heart valve deployment system in accordance with some embodiments.
Figure 18:
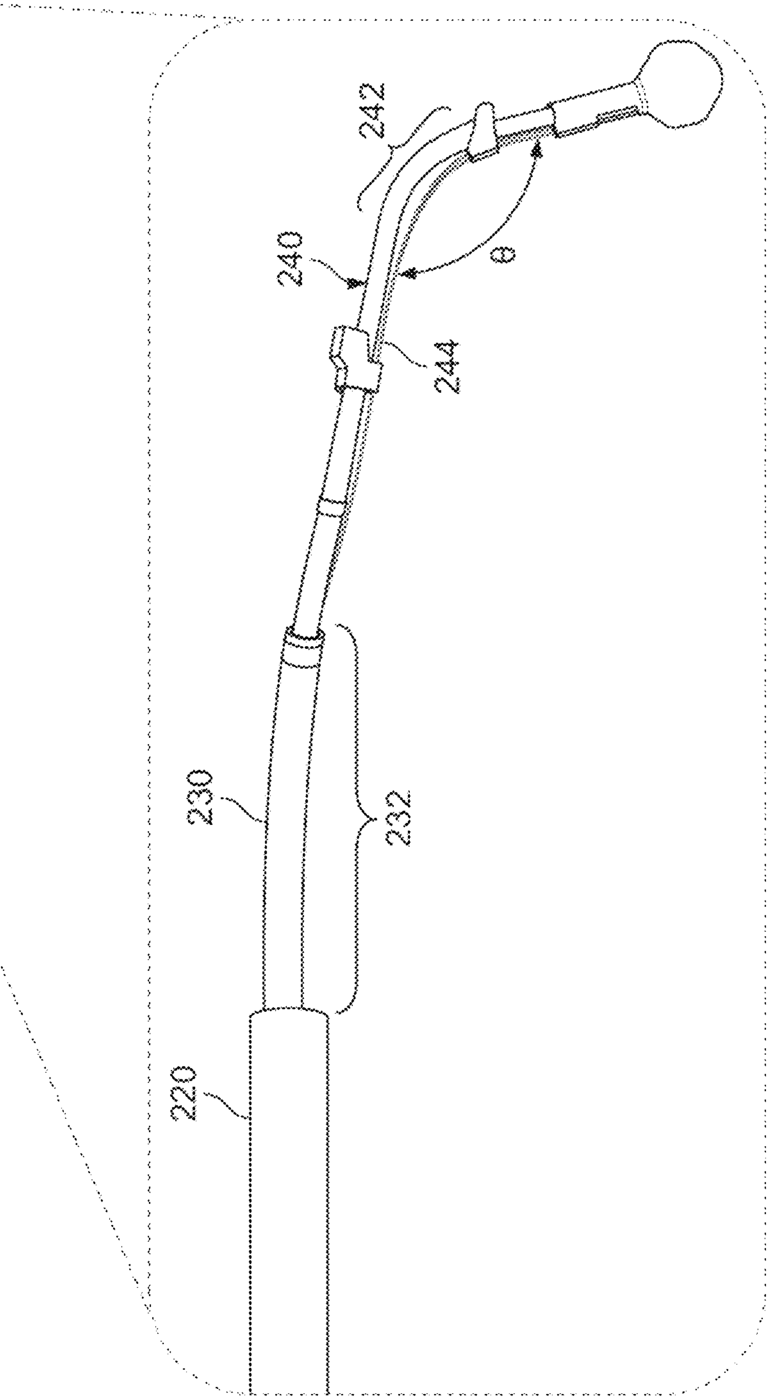
FIG. 18 shows an expanded view of a distal end portion of the prosthetic heart valve deployment system of FIG. 17.

FIGS. 17 and 18 illustrate an example prosthetic heart valve deployment system 200 (or simply "deployment system 200"). The deployment system 200 includes a control handle 210, an outer sheath catheter 220, a middle deflectable catheter 230, and an inner control catheter 240. The outer sheath catheter 220 defines a first lumen. The middle deflectable catheter 230 is slidably disposed in the first lumen and defines a second lumen. The inner control catheter 240 is slidably disposed in the second lumen.

The inner control catheter 240 includes a curved portion 242 (or a linear portion 242 that can be curved by the application of tension from a suture member 255 as described below in reference to FIG. 45). The curved portion 242 is elastically deformable. That is, while the curved portion 242 is located within the confines of the first lumen of the outer sheath catheter 220, the curved portion 242 is essentially linear (or at least more linear than when the curved portion 242 is radially unconstrained). When the curved portion 242 of the inner control catheter 240 is distally expressed out (either by pushing the inner control catheter 240 distally or by pulling the outer sheath catheter 220 proximally) from the confines of the first lumen of the outer sheath catheter 220, the curved portion 242 then naturally elastically reconfigures to exhibit a pronounced curve (e.g., as shown in FIG. 18). Thus, it can be said that the natural shape of the inner control catheter 240 includes the curved portion 242 that defines an interior angle θ. In some embodiments, the interior angle θ can be between 130° and 160°, or between 120° and 150°, or between 110° and 140°, or between 100° and 130°, or between 90° and 120°, or between 80° and 110°, or between 80° and 100°, or between 0° and 10°, or between 0° and 20°, or between 10° and 309, or between 20° and 40, or between 30° and 509, or between 40° and 60°, or between 50° and 70°, without limitation. In some embodiments, the interior angle θ can be less than 160°, or less than 150°, or less than 140°, or less than 135°, or less than 130°, or less than 120°, or less than 110°, or less than 100°, or less than 90°, or less than 80°, or less than 709, or less than 60°, or less than 50°, or less than 40°, or less than 30, or less than 20°, or less than 10°, or less than 5°, or 0° (i.e., linear) without limitation.

The middle deflectable catheter 230 includes a selectively deflectable distal end portion 232 with at least one plane of deflection. In some embodiments, the selectively deflectable distal end portion 232 is deflectable in two planes. In some embodiments, the middle deflectable catheter 230 includes two or more separate selectively deflectable portions that are in same planes or in different planes.

In the depicted embodiment, the selectively deflectable distal end portion 232 is deflectable in a same plane as the plane of the curved portion 242 of the inner control catheter 240. Accordingly, when the selectively deflectable distal end portion 232 of the middle deflectable catheter 230 is deflected, the curvature of the combination of the middle deflectable catheter 230 and the inner control catheter 240 in relation to the axis of the outer sheath catheter 220 is increased beyond that of the interior angle θ alone. In some embodiments, the combined curvature of the middle deflectable catheter 230 and the inner control catheter 240 in relation to the axis of the outer sheath catheter 220 can define an interior angle between 90° and 110°, or between 80° and 100°, or between 70° and 90°, or between 60° and 80°, or between 50° and 70°, or between 30° and 60°, or between 0° and 30°, without limitation. This high degree of curvature can be beneficial during deployment of a prosthetic valve (such as the valve 100) using the deployment system 200, as described further below.

The inner control catheter 240 can also include mechanical features for releasably coupling with a prosthetic valve (such as the valve 100). For example, in the depicted embodiment, the inner control catheter 240 includes one or more control wires and/or release pins 244 that can releasably couple the valve 100 to the inner control catheter 240 in a low profile delivery configuration.

Figure 20:
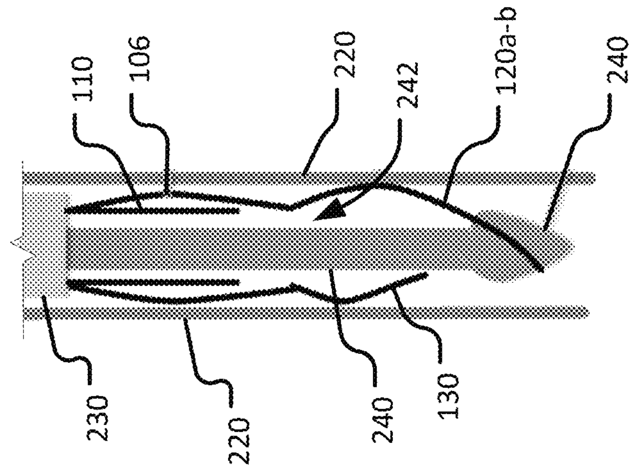
FIG. 20 schematically shows the prosthetic tricuspid valve of FIG. 19 coupled with the prosthetic heart valve deployment system of FIG. 17.
Figure 19:
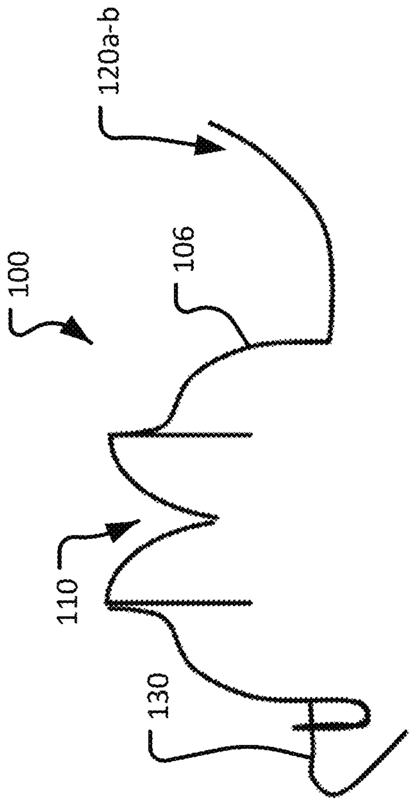
FIG. 19 schematically illustrates a side view of the prosthetic tricuspid valves described herein.

FIG. 19 shows a schematic illustration of the valve 100. FIG. 20 schematically shows the valve 100 coupled to the inner control catheter 240 and located within the first lumen defined by the outer sheath catheter 220. The distal tip of the middle deflectable catheter 230 is also visible. In this arrangement, the valve 100 is radially compressed to a low-profile delivery configuration while within the outer sheath catheter 220. In some embodiments, the valve 100 (or portions thereof are wrapped or folded around the inner control catheter 240. For example, in some embodiments the anterior flaps 120*a-b* are wrapped around the inner control catheter 240. The valve 100 can self-expand as its emergence from the outer sheath catheter 220 takes place (e.g., by the manual retraction of the outer sheath catheter 220 relative to the middle deflectable catheter 230 and the inner control catheter 240).

In some embodiments, when the valve 100 is in its collapsed delivery configuration within the outer sheath catheter 220, the portions of the valve 100 are arranged relative to each other as follows. The first and second anterior flaps 120*a-b* (which can be wrapped on each other) are distal-most. The occluder portion (or valve core) 110 with the flexible leaflets is proximal-most within the outer sheath catheter 220. The posterior anchoring flap 130 is arranged between the distal-most first and second anterior flaps 120*a-b* and the proximal-most occluder portion 110.

The valve 100 can be releasably coupled to the inner control catheter 240 using the one or more control wires and/or release pins 244 (FIG. 18). In some embodiments, a first control wire is releasably coupled to a proximal end portion of the main body 106, a second control wire is releasably coupled to a distal end portion of the main body 106, and a third control wire is releasably coupled to the posterior flaps 120*a-b*. The control wires can be tensioned to draw and maintain the associated portion of the valve 100 radially inward to be snug against the inner control catheter 240. During deployment of the valve 100, the control wires can be individually relaxed to allow the associated portion of the valve 100 to expand elastically toward its natural expanded shape.

Still referring to FIG. 20, in this delivery configuration the curved portion 242 of the inner control catheter 240 is being constrained in an essentially linear configuration by the outer sheath catheter 220. However, when the inner control catheter 240 is expressed from the outer sheath catheter 220 (or as the outer sheath catheter 220 is pulled proximally relative to the inner control catheter 240), the curved portion 242 will become unconstrained and will elastically deflect to its natural curved configuration (e.g., as shown in FIG. 18). The curved configuration of the curved portion 242 is beneficial for the deployment process of the valve 100 into engagement with a native tricuspid valve 10, as described further below.

FIGS. 21-30 illustrate a series of steps for deploying a prosthetic heart valve (such as the heart valve 100 described herein in any of its variations) using the heart valve deployment system 200. These figures illustrate a trans-jugular vein approach to the native tricuspid valve 10 (via the superior vena cava).

Figure 21:
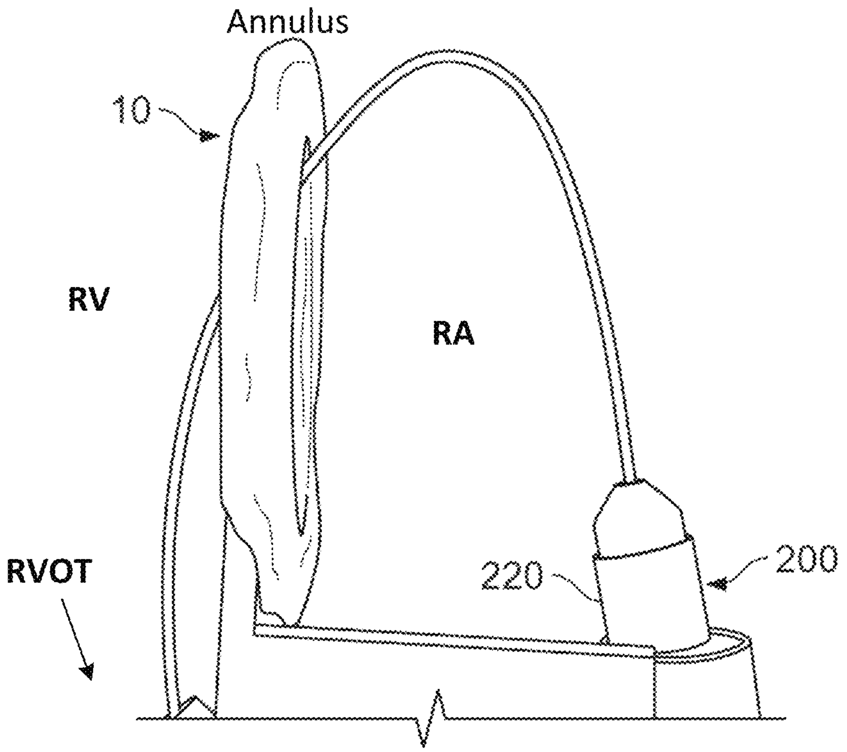
FIGS. 21 through 30 show an example trans-jugular method of deploying the prosthetic tricuspid valves described herein using the prosthetic heart valve deployment system of FIG. 17.

FIG. 21 shows a distal end portion of the deployment system 200 emerging into the right atrium via the superior vena cava. The deployment system 200 is being advanced over a guidewire that was installed previously. The valve 100 (not visible) is within the outer sheath catheter 220.

Figure 22:
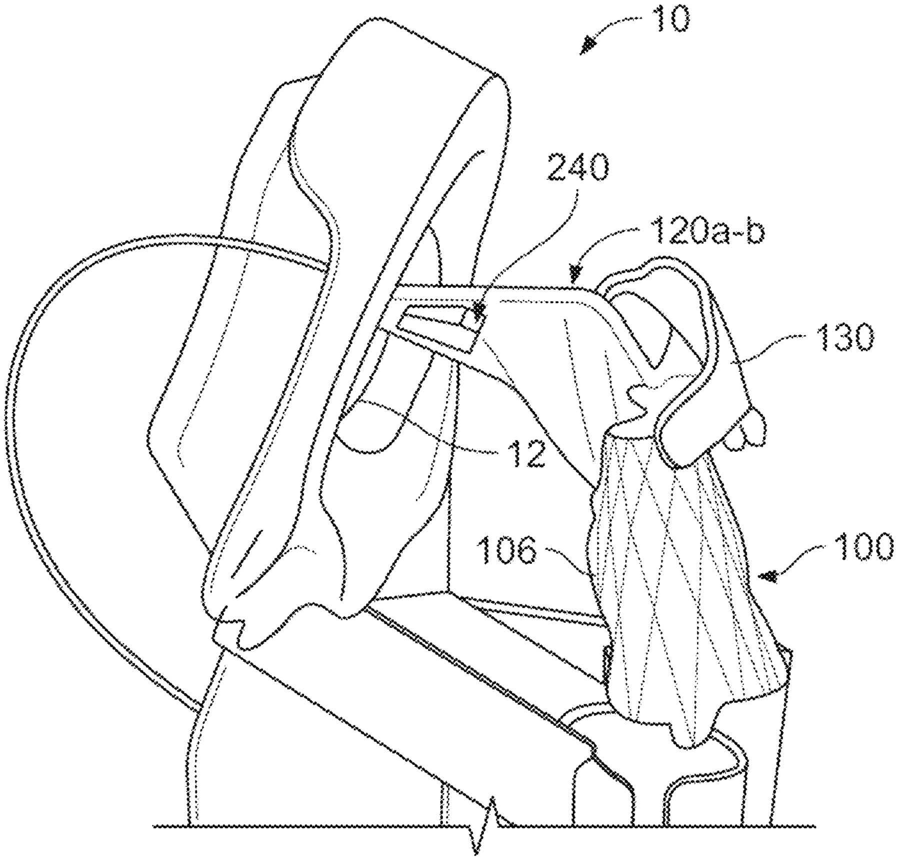

FIG. 22 illustrates the valve 100 (while the valve 100 is releasably coupled to the inner control catheter 240) after the withdrawal of the outer sheath catheter 220 and/or the advancement of the inner control catheter 240 and the middle deflectable catheter 230. At this stage, the curved portion 242 (not visible under the valve 100) has become unconstrained and has elastically deflected to its natural curved configuration. The natural curved configuration of the curved portion 242 facilitates the inner control catheter 240 to make a relatively tight turn within the right atrium to advance from the vena cava and through the annulus 12 of the native tricuspid valve 10 as depicted.

Figure 23:
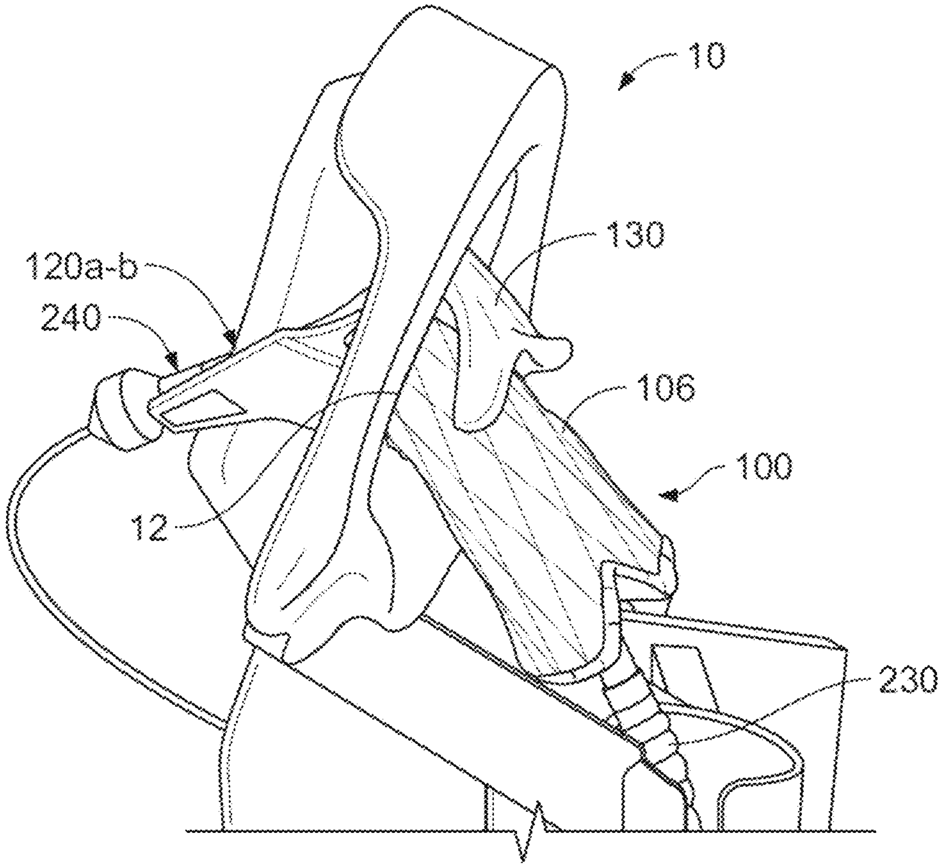
Figure 24:
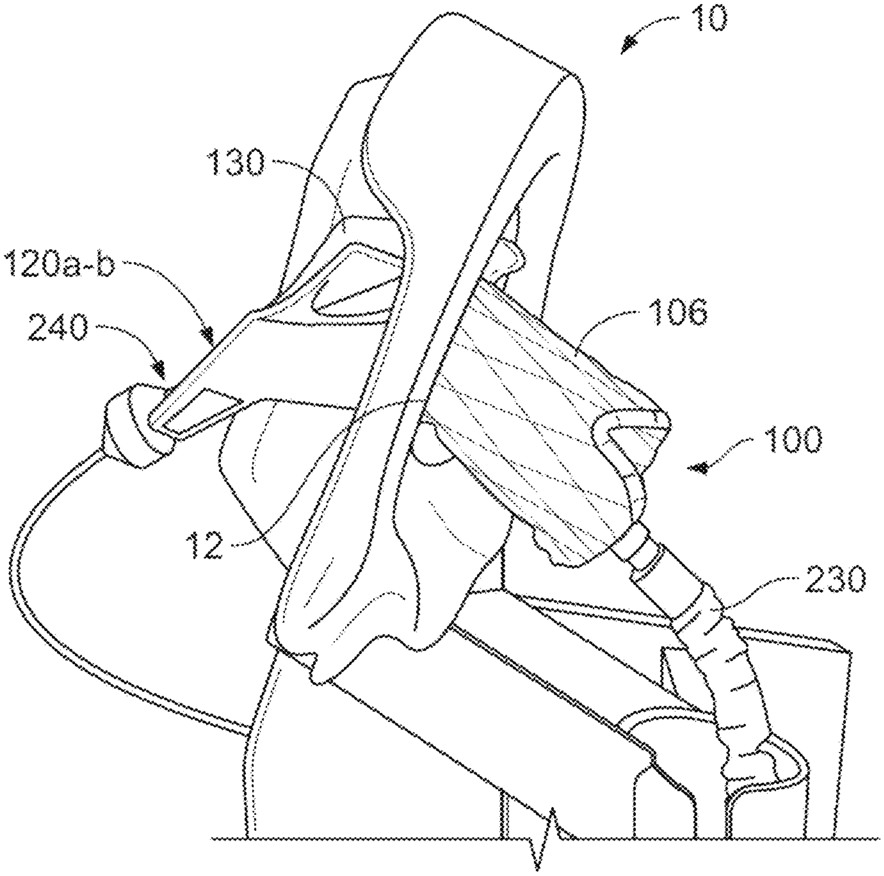

FIGS. 23 and 24 illustrate further advancement of the valve 100 (while the valve 100 is still releasably coupled to the inner control catheter 240). In these images, the middle deflectable catheter 230 is being deflected (by a first amount in FIG. 23 and a greater amount in FIG. 24). The deflection of the middle deflectable catheter 230 adds to the curvature of the inner control catheter 240 to enable the distal end portion of the inner control catheter 240 to become directed toward the RVOT after passing through the annulus 12 (as shown in FIG. 24).

Figure 25:
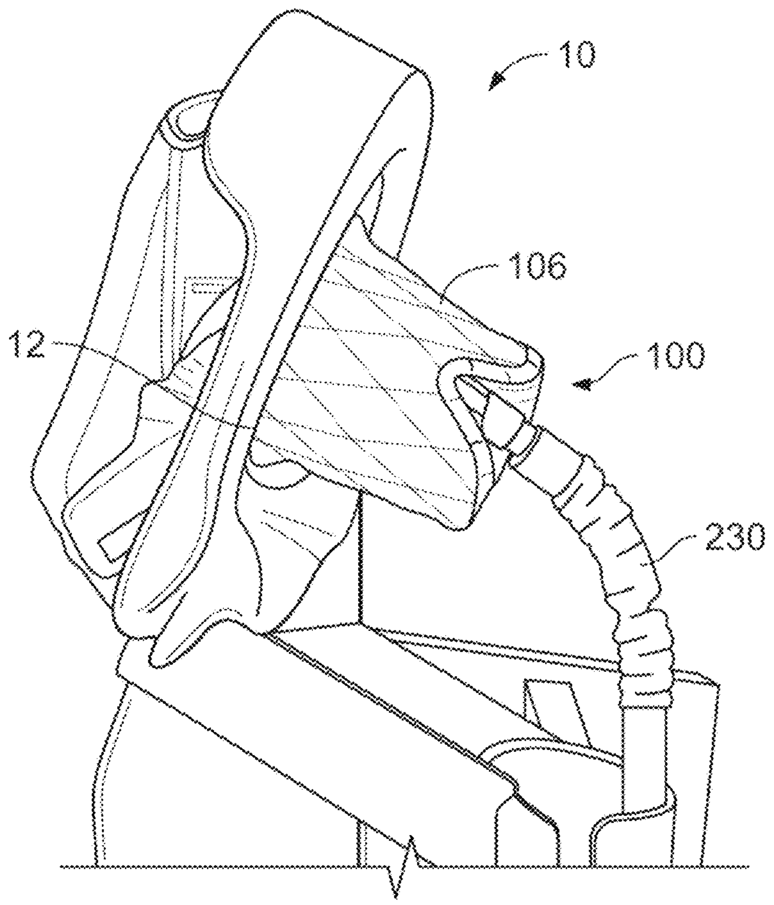
Figure 26:
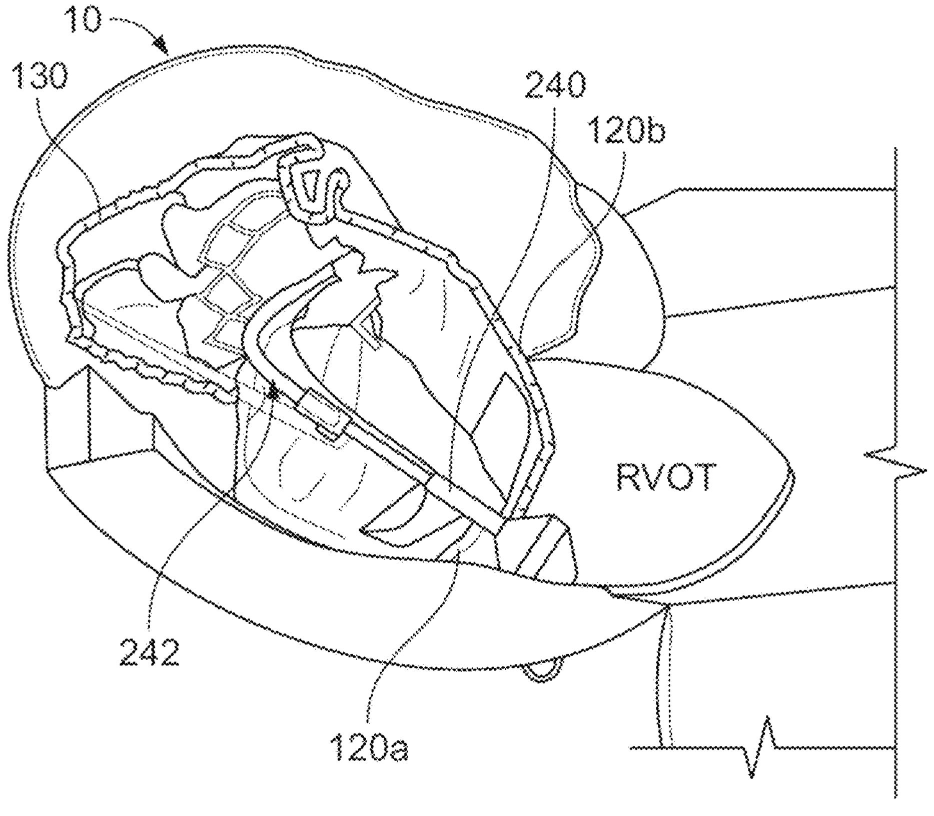
Figure 27:
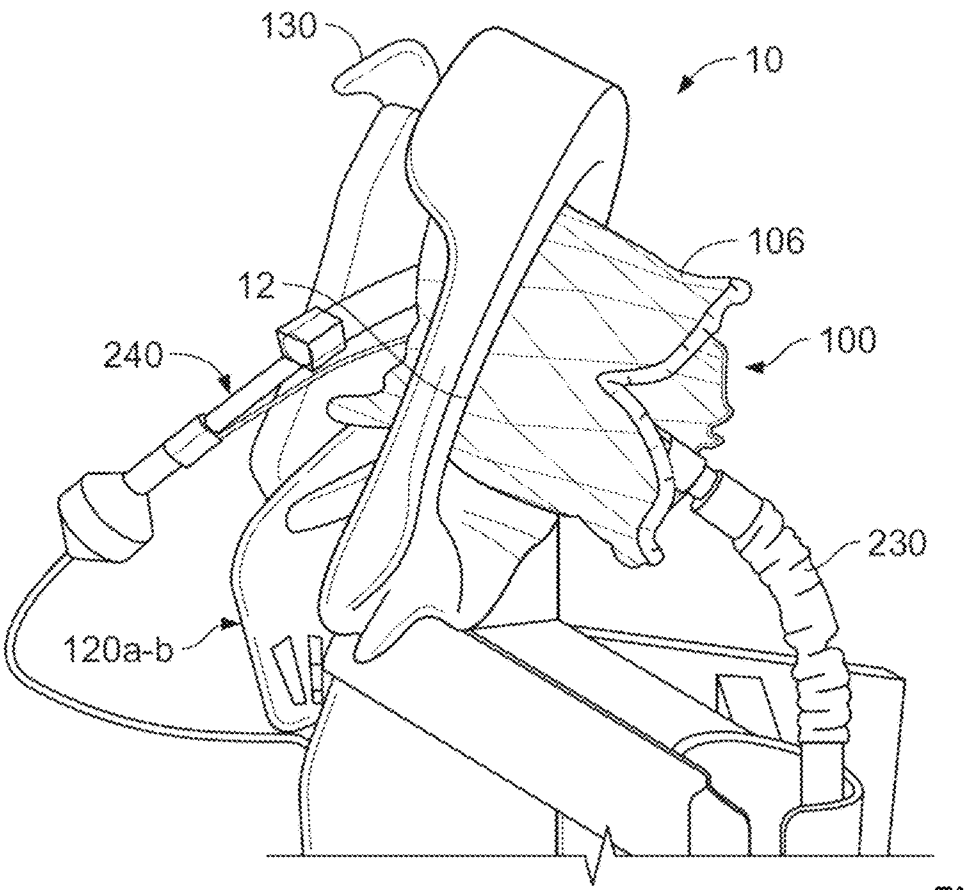

FIGS. 25 through 27 illustrate the release process of the portions of the valve 100 from the inner control catheter 240. As the portions of the valve 100 are released, those portions become engaged in the targeted native anatomical locations. The control wires and/or release pins for the anterior flaps 120*a-b* and the posterior flap 130 are released (as best seen in FIG. 26). In response, the anterior flaps 120*a-b* deploy into the RVOT and the posterior flap 130 deploys to the posterior area of the tricuspid valve 10 just inferior to the annulus 12. In addition, as the posterior flap 130 deploys, the one or more leaflet engagement members 140 engage with and capture/hold a portion of the native leaflet (e.g., the posterior leaflet 11*p* and/or the septal leaflet 11*s*) to provide migration resistance for the valve 100. At this stage, the posterior arm 150 and/or the anterior arm 160 (FIGS. 6-9) can also be deployed if the valve 100 includes a posterior arm 150 and/or an anterior arm 160. FIG. 27 shows the release of control wires that are coupled to the main body

106. In response, the main body 106 radially expands into contact and engagement with the annulus 12.

Figure 28:
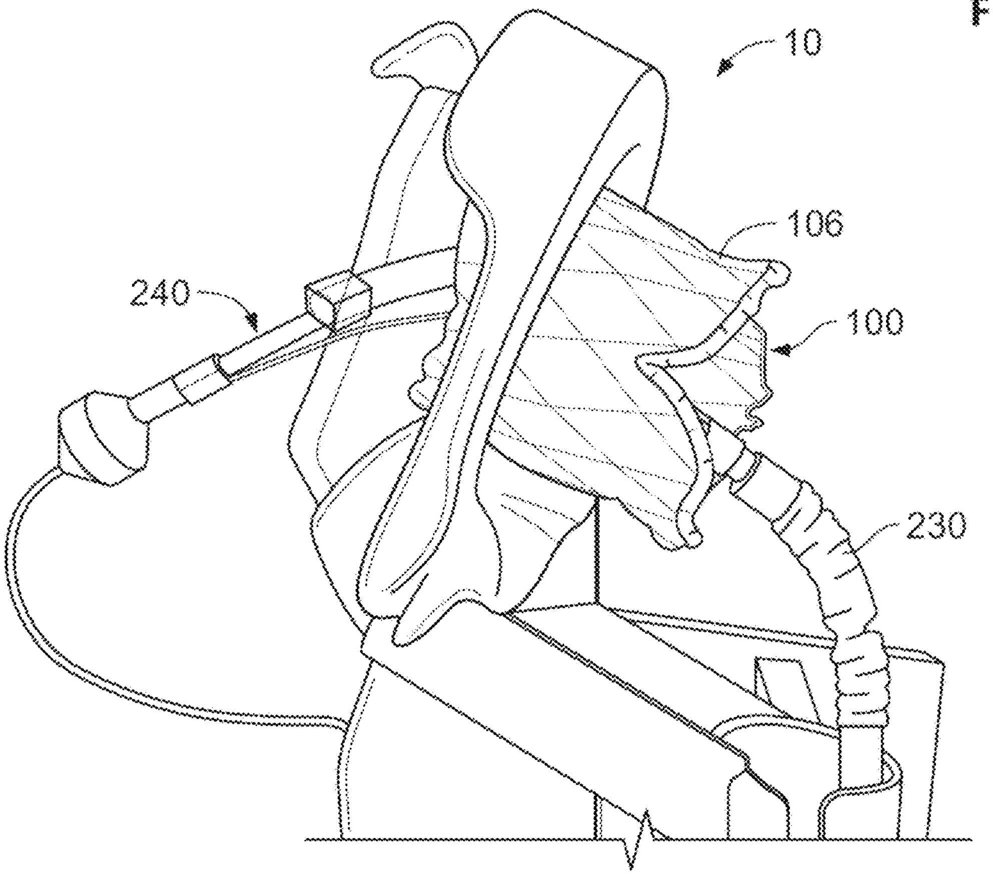
Figure 29:
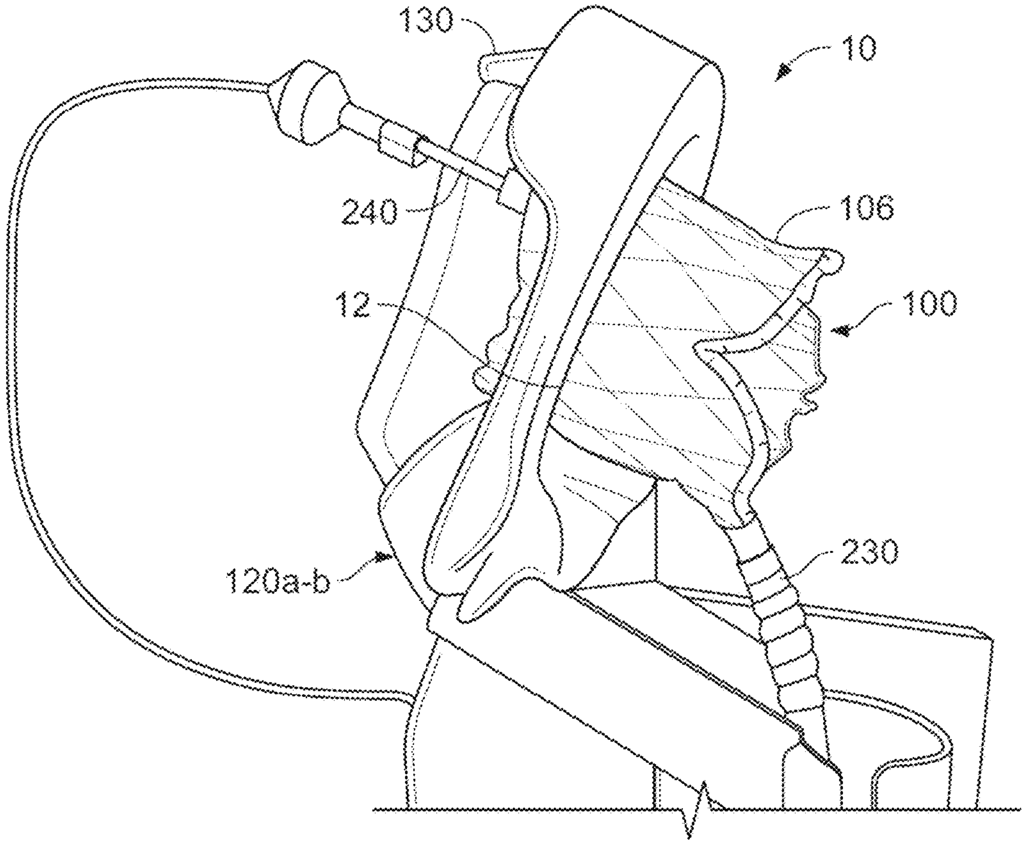
Figure 30:
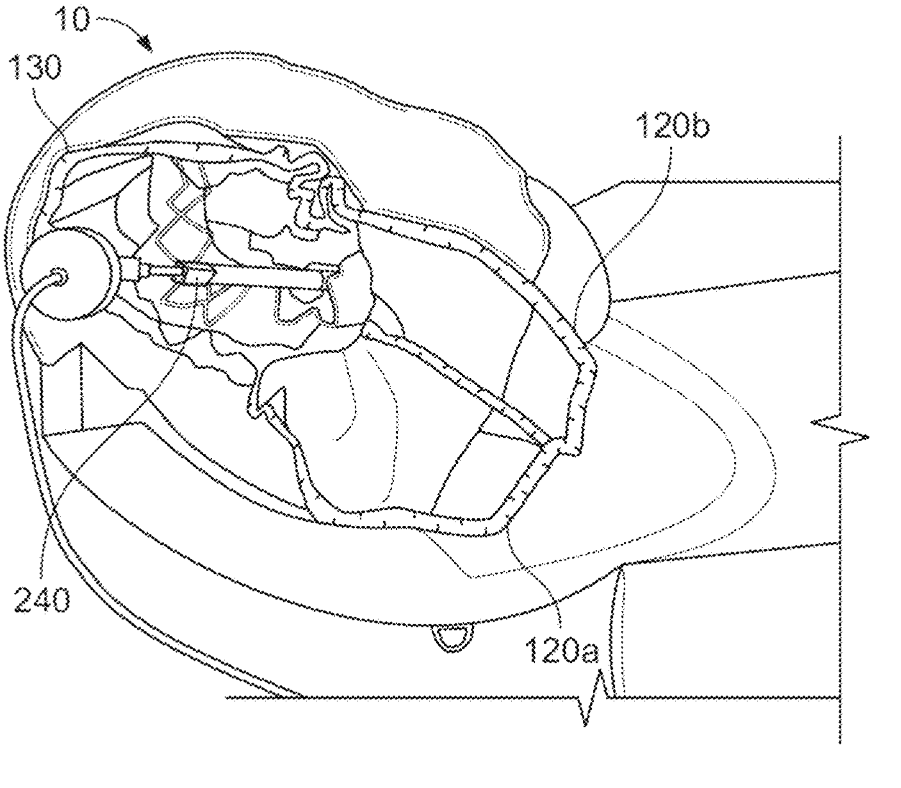

FIGS. 28 through 30 illustrate withdrawal of the deployment system 200. When the control wires are disengaged from the valve 100, the inner control catheter 240 and the middle deflectable catheter 230 can then be withdrawn, leaving the valve 100 engaged with the anatomy in and around the native tricuspid valve 100.

FIG. 31 illustrates another example prosthetic heart valve 300. The valve 300 is similar to the valve 100 described above, but is modified to be better suited for trans-femoral delivery (via the inferior vena cava) to the native tricuspid valve 10. The valve 300 includes an ovular main body 306 that contains a circular occluder 310 that defines a central axis 301. The occluder 310 extends between an inflow end and an outflow end portion of the main body 306, and includes valve leaflets in an arrangement that: (i) allows blood flow through the occluder 310 in a direction from the inflow end portion toward the outflow end portion along a central axis 301 of the occluder 310 and (ii) prevents blood flow through the occluder 310 in a direction from the outflow end portion toward the inflow end portion. The valve 300 also includes a first anterior flap 320*a* extending from the outflow end portion of the main body 306 in a first direction that is transverse to the central axis 301, and a second anterior flap 320*b* also extending from the outflow end portion in the first direction. The valve 300 also includes a first posterior flap 330*a* extending from the outflow end portion of the main body 306 in a second direction that is opposite of the first direction, and a second posterior flap 330*b* also extending from the outflow end portion in the second direction. A passageway 332 (e.g., for a pacemaker lead as described above) is defined between the first and second posterior flaps 330*a-b*. In contrast to the valve 100, the first and second posterior flaps 330*a-b* of the valve 300 extend from the outflow end portion of the main body 306 farther (a greater distance) than the first and second anterior flaps 320*a-b*. This arrangement biases the main body 306 toward the anterior portion of the annulus 12 (refer to FIG. 10), which is different from the valve 100 which is biased toward the posterior portion of the annulus 12 (refer to FIG. 12).

FIGS. 32-37 schematically illustrate a series of steps for deploying the heart valve 300 (as described herein in any of its variations) into the heart 1 using the heart valve deployment system 200 (e.g., refer to FIGS. 17 and 18). These figures illustrate a trans-femoral vein approach to the native tricuspid valve 10 (via the inferior vena cava; "IVC").

Figure 32:
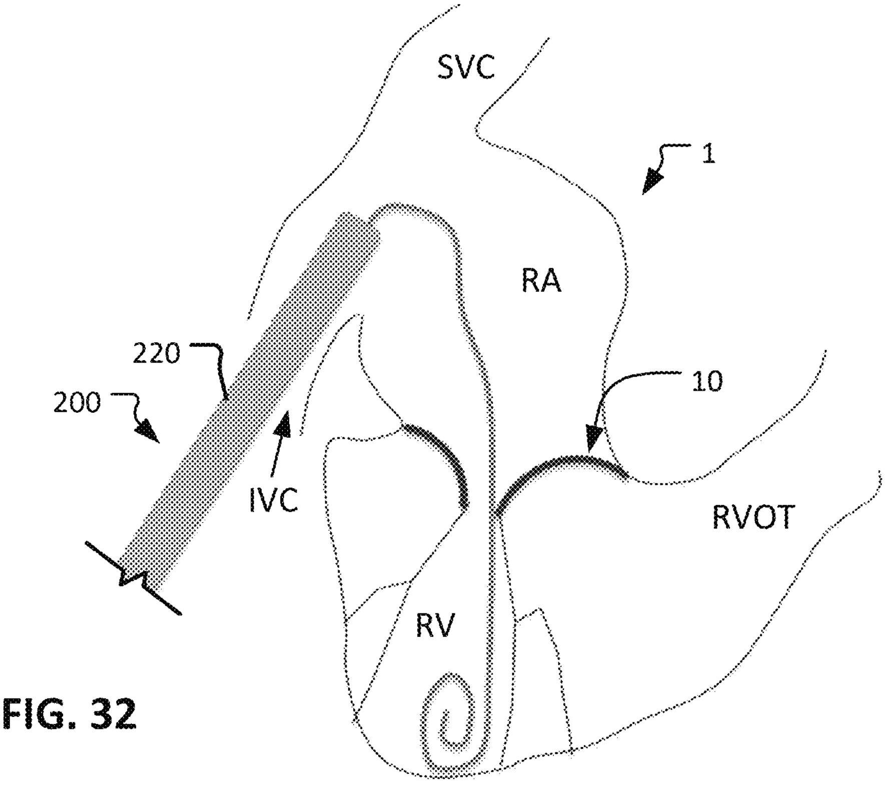
FIGS. 32-37 schematically depict an example trans-femoral method of deploying the prosthetic heart valve of FIG. 31 using the prosthetic heart valve deployment system of FIG. 17.

FIG. 32 illustrates the advancement of the deployment system 200 toward the right atrium ("RA") via the IVC. The outer sheath catheter 220 (containing the heart valve 300 in its low-profile delivery configuration) can be advanced over a previously placed guidewire that extends into the right ventricle ("RV") via the native tricuspid valve 10.

Figure 33:
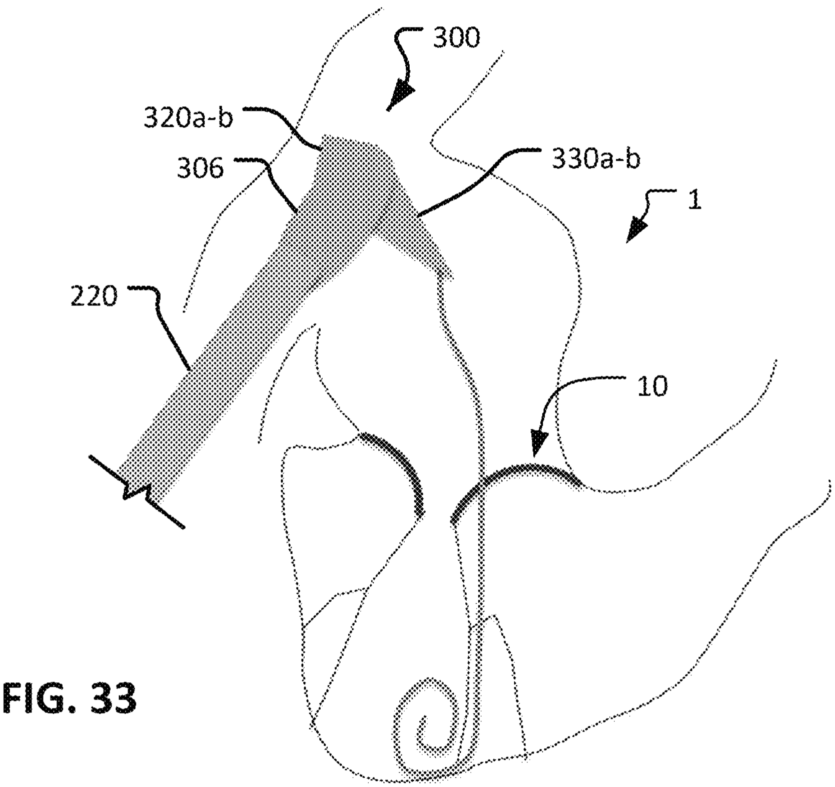

FIG. 33 illustrates the emergence in the RA of the heart valve 300 from the outer sheath catheter 220 (e.g., by pulling the outer sheath catheter 220 proximally and/or by distally advancing the middle deflectable catheter 230 and inner control catheter 240). That is, the emergence in the RA of the heart valve 300 out from the outer sheath catheter 220 can be performed by distally pushing the heart valve 300 out from the outer sheath catheter 220 by advancing the middle deflectable catheter 230 and inner control catheter 240 while maintaining the outer sheath catheter 220 substantially stationary (or while pulling the outer sheath catheter 220 proximally).

Figure 34:
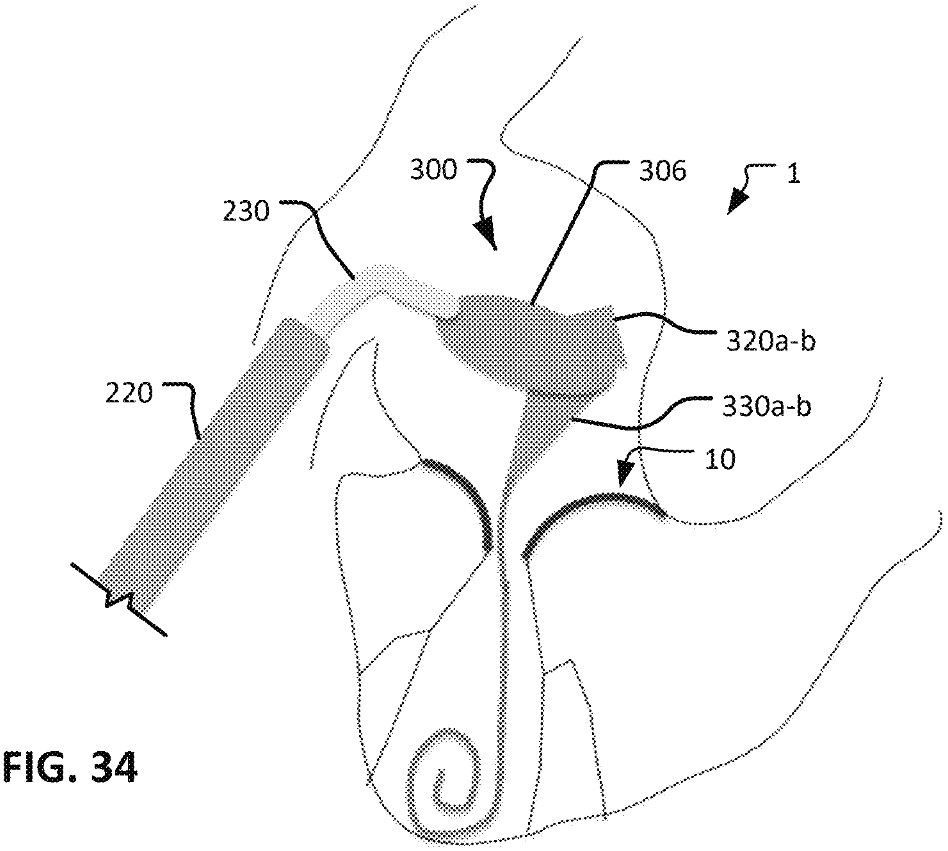
Figure 35:
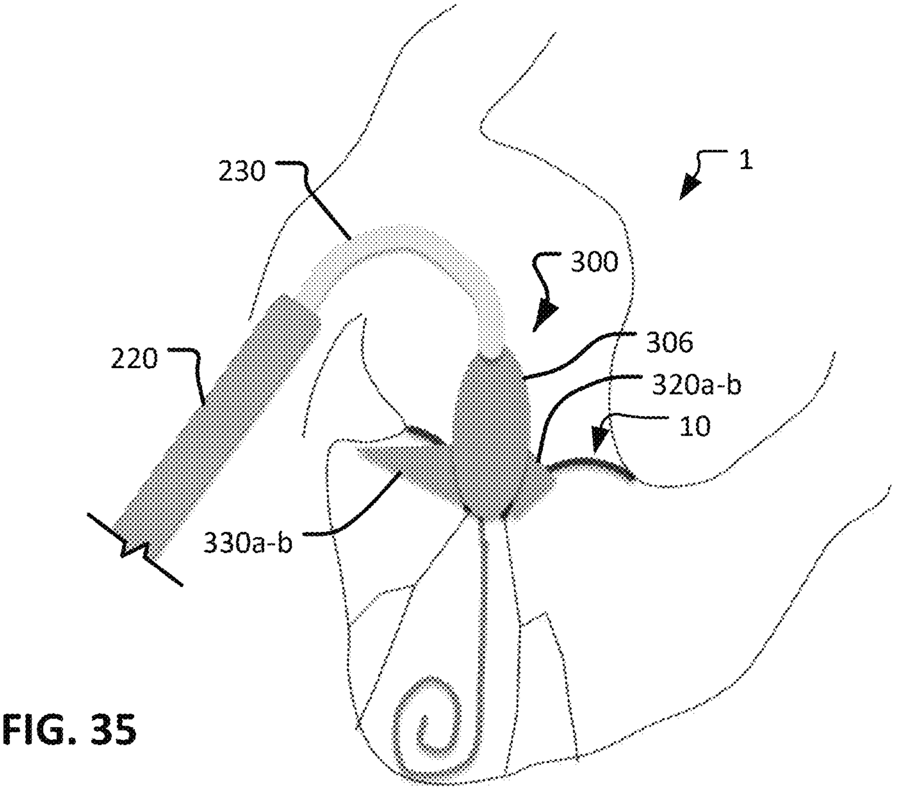

FIGS. 34 and 35 illustrate the advancement of the heart valve 300 into position for engagement with the native tricuspid valve 10. To accomplish this, the middle deflectable catheter 230 and inner control catheter 240 are both curved. That is, the inner control catheter 240 is naturally curved because of its curved portion 242, and the middle deflectable catheter 230 is selectively deflected by a clinician operator who is performing the procedure.

Figure 36:
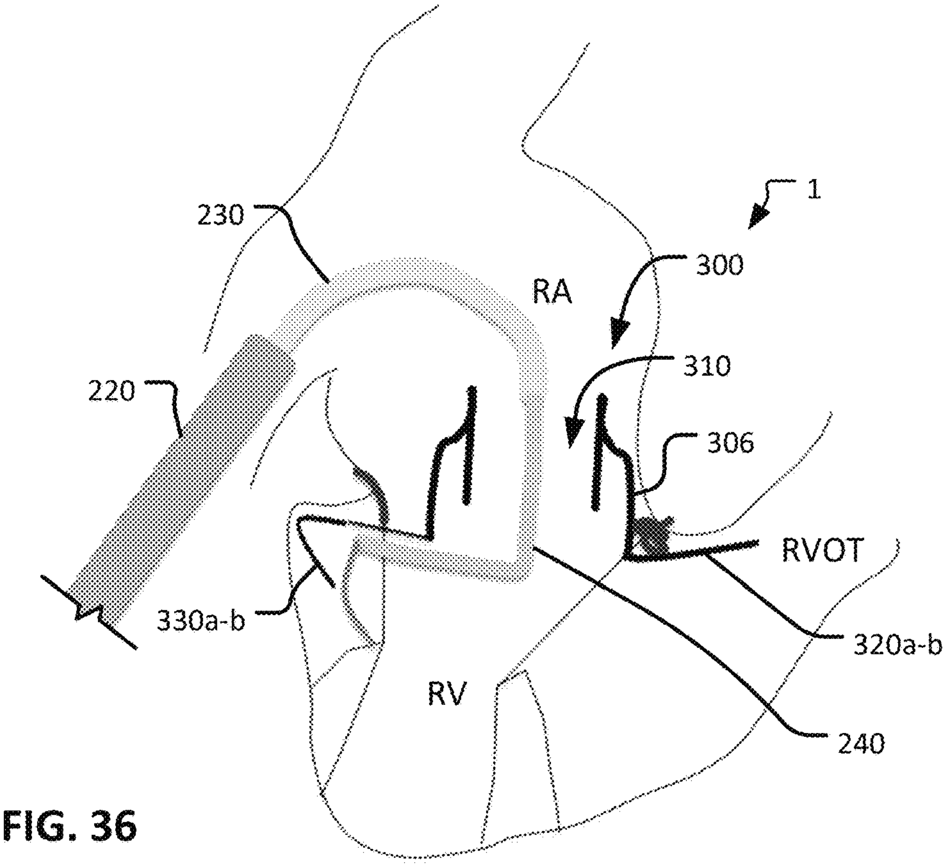

FIG. 36 illustrates the release of the heart valve 300 from the inner control catheter 240, and the resulting expansion/deployment of the heart valve 300 into engagement at the location of the native tricuspid valve 10. The release of the various components/regions of the heart valve 300 can be performed in a controlled manner by manual manipulation of the one or more control wires and/or release pins 244 (FIG. 18) by the clinician operator. The release of the heart valve 300 from the inner control catheter 240 results in the expansion of the main body 306, the anterior flaps 320*a-b*, and the posterior flaps 330*a-b* into engagement with the anatomy of the native tricuspid valve 10, the RV, and the RVOT.

Figure 37:
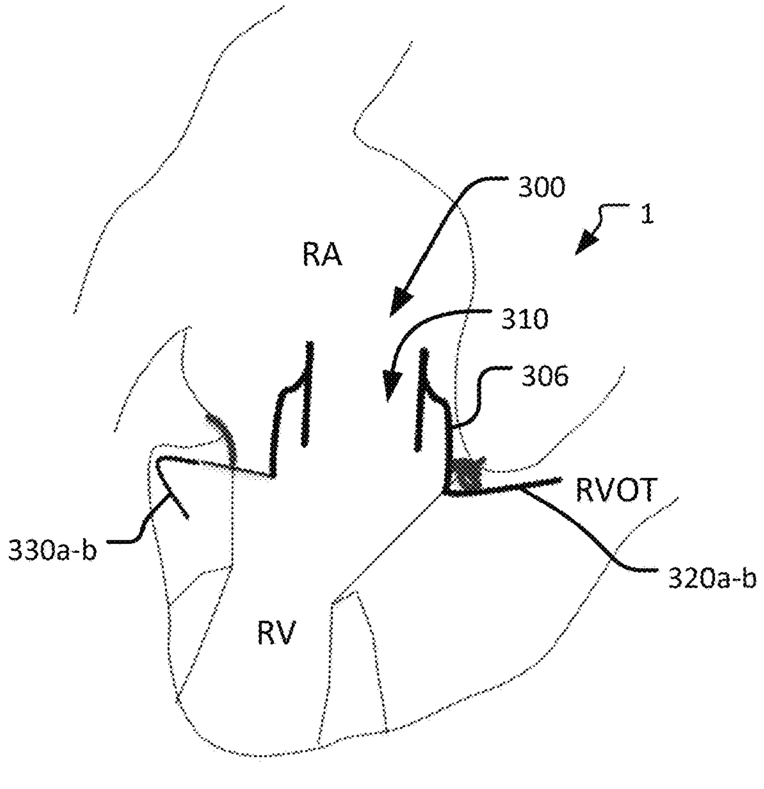

Lastly, FIG. 37 illustrates the implanted heart valve 300 in engagement with the heart 1 and functioning as a prosthetic tricuspid valve between the RA and the RV. The deployment system 200 and guidewire have been withdrawn. It can be seen here (and in the top view of FIG. 31) that the heart valve 300 is positioned such that the main body 306 is positionally biased toward the anterior portion of the annulus 12 (refer to FIG. 10), which is adjacent the RVOT. Accordingly (and as shown in FIG. 31), the laterally-extending first and second posterior flaps 330*a-b* help to cover and fluidly seal the native tricuspid valve opening within the annulus 12, which is not circular in this example (e.g., with the native valve opening being oblong, oval, or irregularly shaped). In other words, in combination with the main body 306 of the valve 300, the first and second posterior flaps 330*a-b* (and, in some cases, the laterally-extending anterior anchoring flaps 320*a-b* to a lesser extent) help to cover/occlude and fluidly seal the native tricuspid valve opening which is not circular in some cases. In addition, the end portions of the first and second posterior flaps 330*a-b* extend into engagement with the posterior shelf 11 (FIG. 4) and/or with the wall of the RV just inferior to the annulus 12 to provide anchoring and migration resistance. Accordingly, the first and second posterior flaps 330*a-b* perform both sealing and anchorage.

Figure 38:
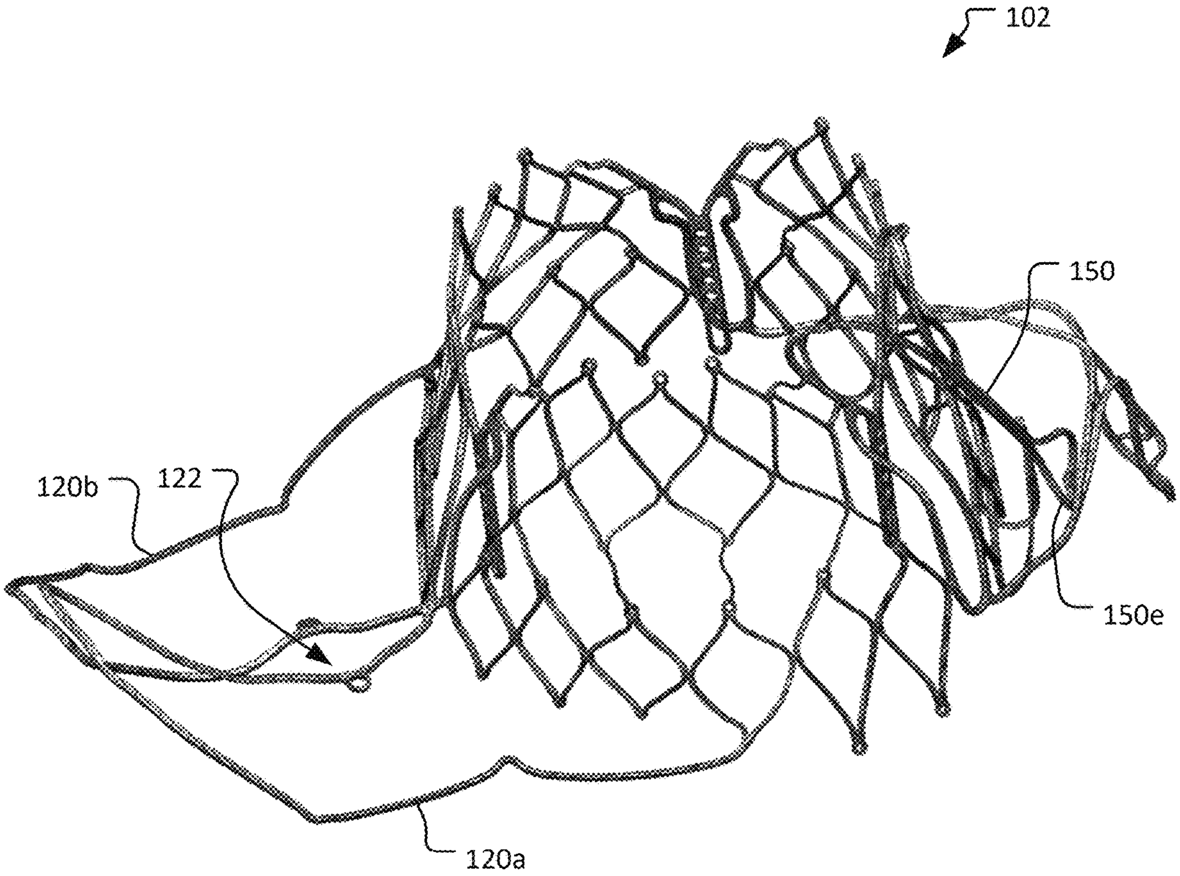
FIG. 38 is a perspective view of an example frame that can be used for the prosthetic heart valves described herein.
Figure 39:
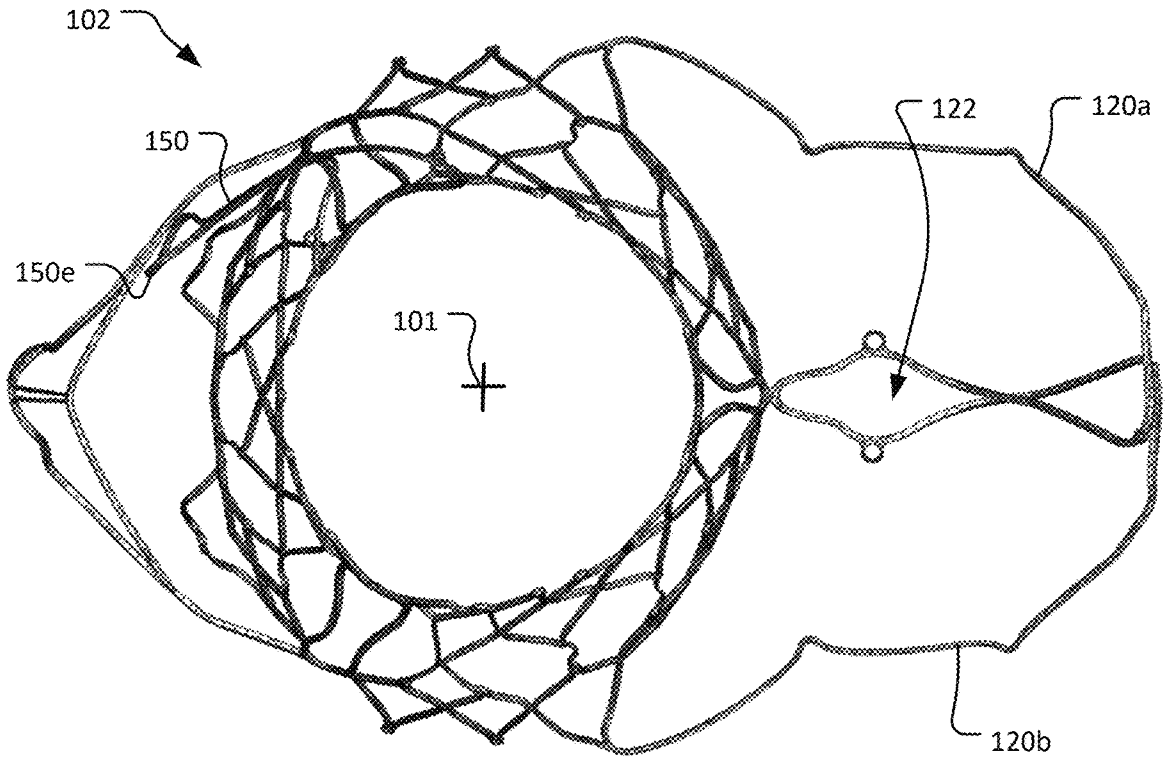
FIG. 39 is a top view of the frame of FIG. 38.
Figure 40:
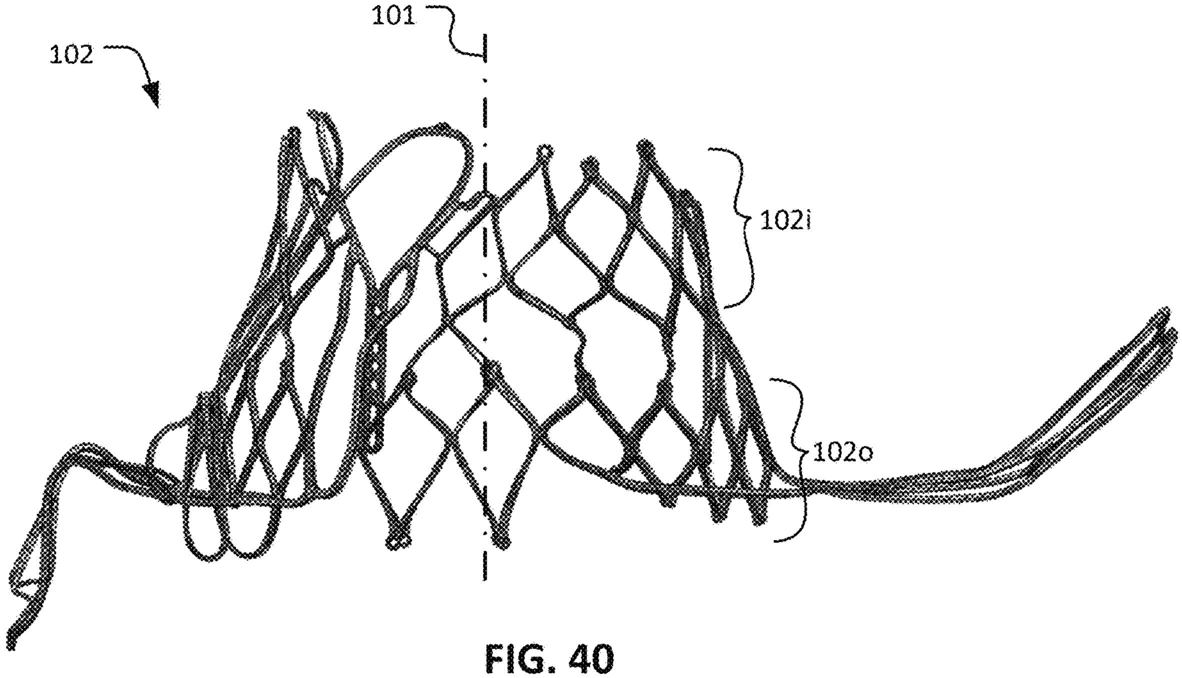
FIG. 40 is a side view of the frame of FIG. 38.

FIGS. 38-40 illustrate the frame 102 that can be used in some embodiments of the prosthetic heart valves described herein. The frame 102 has a cellular construction that provides mechanical support for the shape and structures of the prosthetic heart valves. In some embodiments, the frame 102 is made from nitinol (NiTi), stainless steel, cobalt chromium, MP35N, titanium, polymeric materials, other biocompatible materials, or any combination thereof. Some or all parts of the frame 102 may be covered (e.g., by the covering 104 described above). In some embodiments, the frame 102 can be made of a laser cut, expanded, and shape-set material. The frame 102 is self-expanding in some embodiments. In some embodiments, the precursor material is tubular NiTi, a NiTi sheet, or other suitable types of precursor materials.

In this example, the frame 102 includes the optional posterior arm 150 with the free end 150*e*. The posterior arm 150 can also be referred to as a "diastolic anchoring tab," because the posterior arm 150 helps to prevent migration of the prosthetic heart valve toward the right ventricle during diastole. In this example, the frame 102 does not include the anterior arm 160 (e.g., see FIG. 9). However, in some embodiments the anterior arm 160 is included as part of the frame 102.

In this example, the frame 102 does not include the frame portions 128*a* and 128*b* (e.g., see FIG. 9). However, in some embodiments the frame portions 128*a* and 128*b* are included as part of the frame 102.

As best seen in FIG. 40, the frame 102 includes an inflow end portion 102*i* and an outflow end portion 1020. In the depicted embodiment, the cellular structure of the inflow end portion 102*i* and an outflow end portion 102*o* differ from each other. In particular, the size of the cells that make up the inflow end portion 102*i* are smaller than the size of the cells that make up the outflow end portion 102*o*. For example, the cells of the inflow end portion 102*i* have a shorter longitudinal length (e.g., measured longitudinally parallel to the longitudinal axis 101) than the cells of the outflow end portion 1020. Said another way, the cells of the outflow end portion 102*o* are longer when measured along the longitudinal direction of the frame 102 than the cells of the inflow end portion 102*i*.

The differences in the sizes of the cells of the inflow end portion 102*i* as compared to the cells of the outflow end portion 102*o* causes the frame 102 to advantageously have different structural characteristics along the longitudinal length of the frame 102. For example, the inflow end portion 102*i* of the frame 102 is structurally stiffer than the outflow end portion 102*o*, particularly as related to radially directed forces. Conversely, the outflow end portion 102*o* of the frame 102 is structurally more flexible than the inflow end portion 102*i*. Moreover, the structures of the anterior flaps 120*a-b* are very flexible because of the anterior flaps 120*a-b* are primarily made of large open areas within peripheral frame members (e.g., see FIG. 39).

It can be advantageous for the inflow end portion 102*i* of the frame 102 to be structurally stiff. For example, such stiffness can help to maintain the circular cross-sectional shape of the occluder of the prosthetic valve (e.g., the occluder 110 shown in FIGS. 6-8) while the heart muscle contracts to pump blood. Keeping such a circular cross-sectional shape of the occluder can serve to ensure that the leaflets of the occluder maintain their relative orientations in a predictable way. This can beneficially provide robust coaptation between the leaflets to mitigate the occurrence of regurgitation through the occluder, for example.

It can be advantageous for the outflow end portion 102*o* of the frame 102 and the anterior flaps 120*a-b* to be structurally flexible. For example, such flexibility can beneficially mitigate the amount of force from the frame 102 that is exerted onto the anatomy of the heart. In particular, having a flexible outflow end portion 102*o* and flexible anterior flaps 120*a-b* reduces or eliminates forces from the frame 102 from being applied to certain sensitive anatomical areas such as the AV node, the right coronary artery, and the annulus of the heart valve, to provide a few examples.

Figure 41:
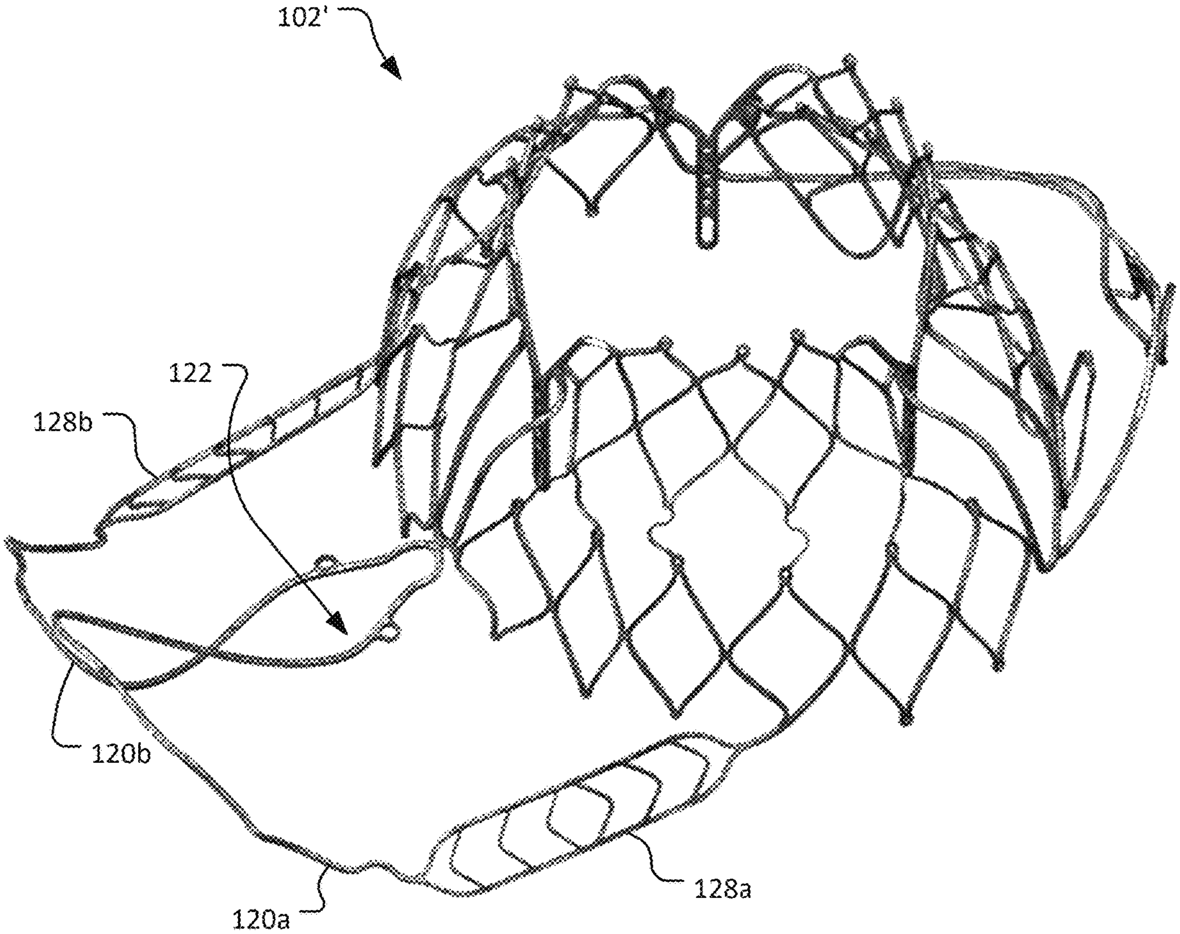
FIG. 41 is a perspective view of another example frame that can be used for the prosthetic heart valves described herein.
Figure 42:
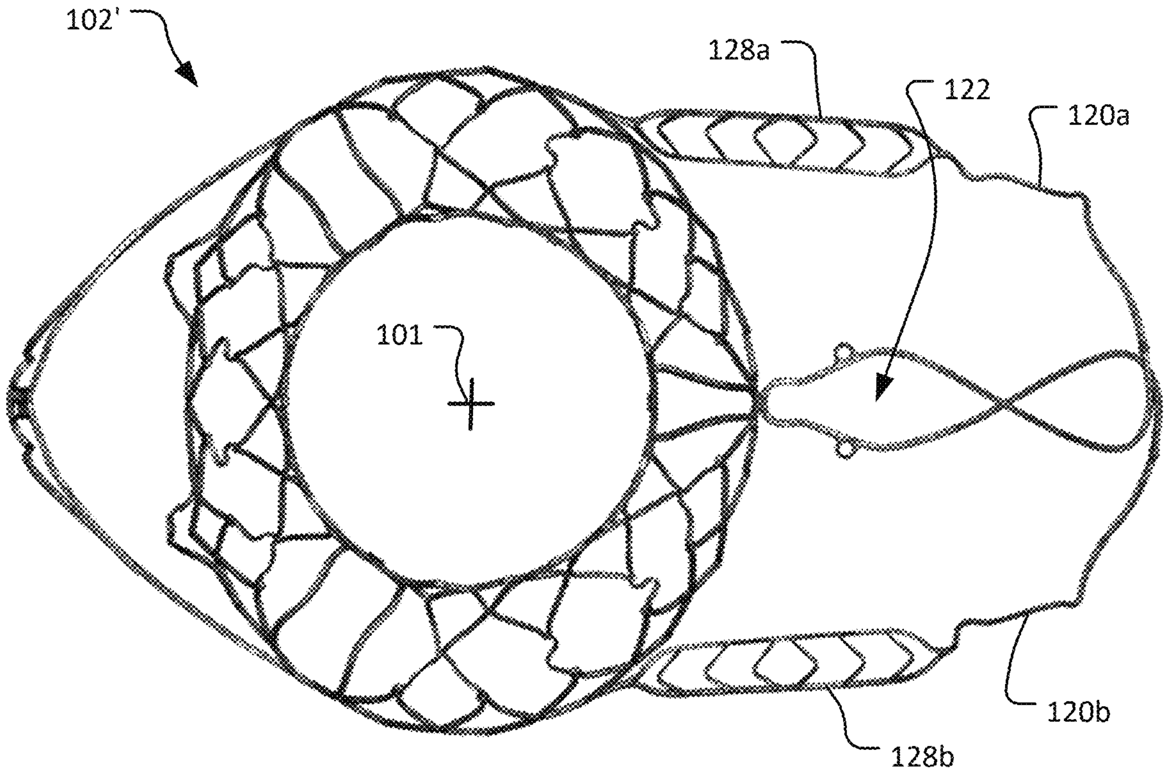
FIG. 42 is a top view of the frame of FIG. 41.
Figure 43:
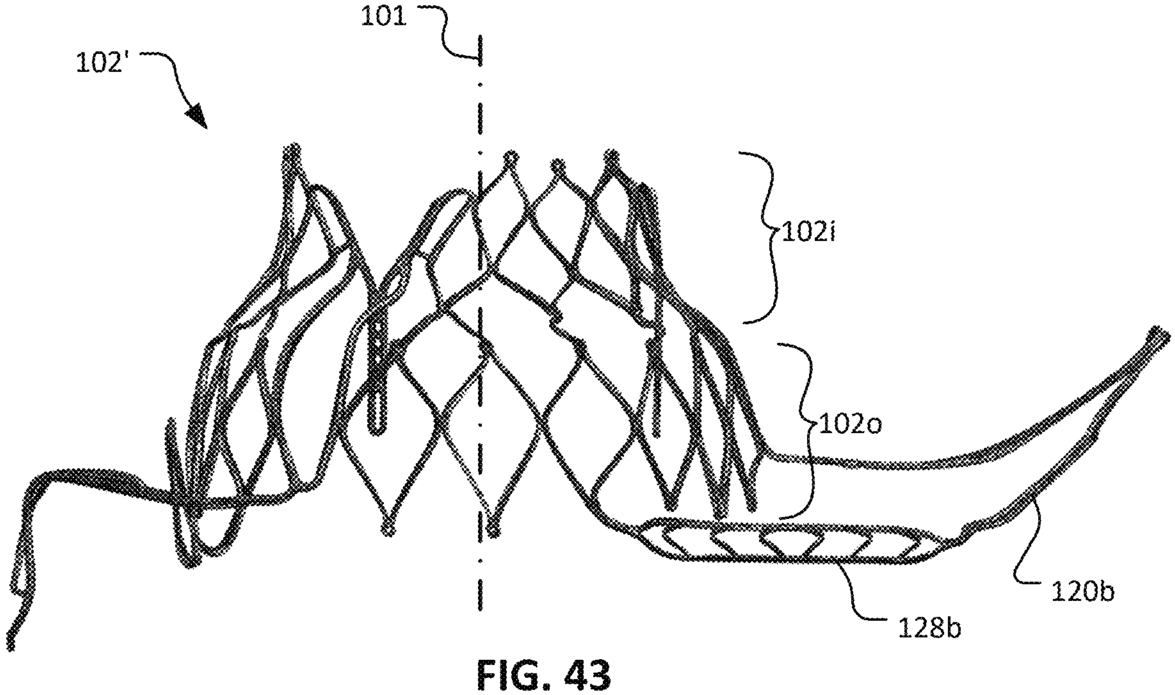
FIG. 43 is a side view of the frame of FIG. 41.

FIGS. 41-43 illustrate another example frame 102' that can be used in some embodiments of the prosthetic heart valves described herein. This embodiment is different from the frame 102 in that the frame 102' includes the frame portions 128*a* and 128*b* and does not include the posterior arm 150 (and also does not include an anterior arm 160). It should be understood that such features can be mixed and matched in any desired combination.

The frame 102' shares the cell-size characteristics of the frame 102 as described above. That is, the cells that make up the inflow end portion 102*i* are smaller and stiffer than the cells that make up the outflow end portion 102*o*. The cells of the anterior flaps 120*a-b* have the largest size (making them the most flexible portion of the frame 102').

Alternative methods of achieving the variable stiffness characteristics described above are also contemplated. For example, the strut widths and/or thicknesses of different portions of the frame 102 could be different.

Figure 44:
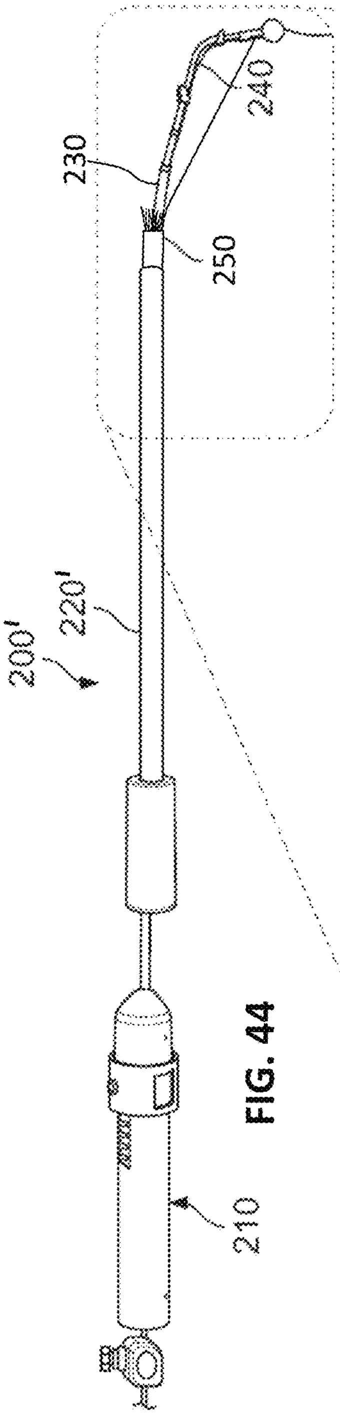
FIG. 44 illustrates another example prosthetic heart valve deployment system.
Figure 45:
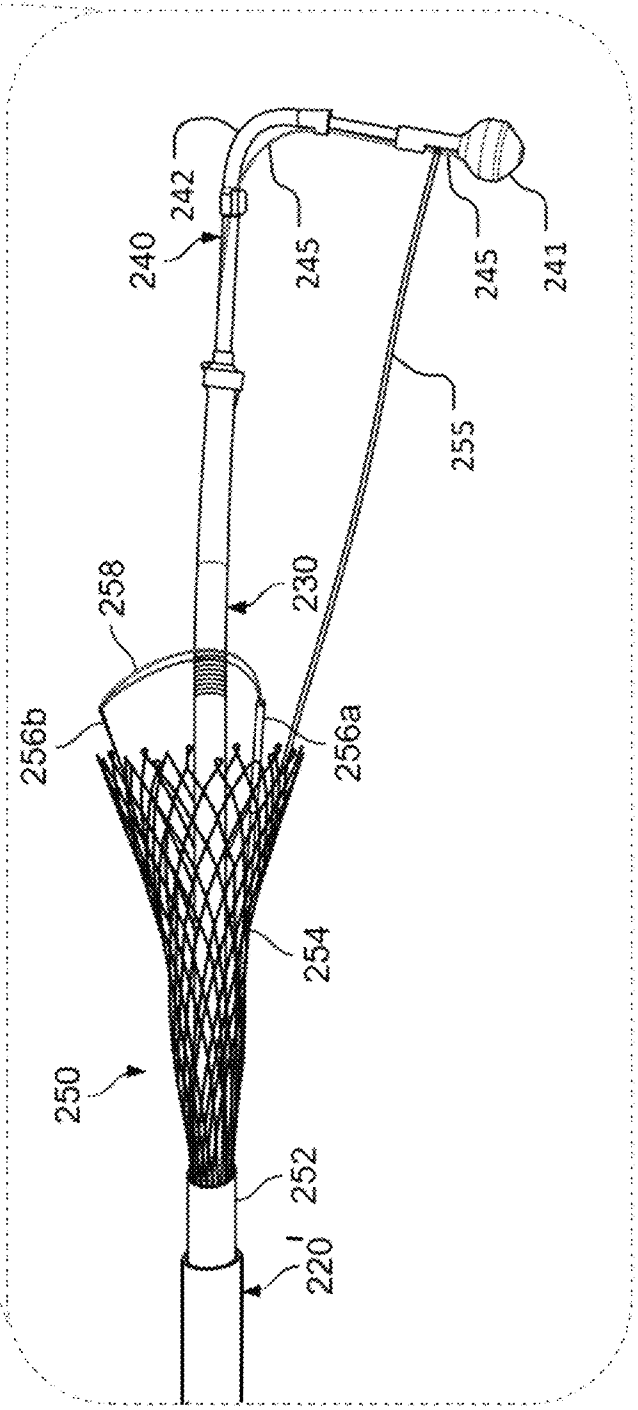
FIG. 45 shows an enlarged view of a distal end portion of the prosthetic heart valve deployment system of FIG. 44.

FIGS. 44 and 45 illustrate another example prosthetic heart valve deployment system 200' (or simply "deployment system 200'"). The deployment system 200' includes a control handle 210, an outer steerable sheath catheter 220', a middle deflectable catheter 230, and an inner control catheter 240. The outer steerable sheath catheter 220' defines a first lumen. The middle deflectable catheter 230 is slidably disposed in the first lumen and defines a second lumen. The inner control catheter 240 is slidably disposed in the second lumen.

As best visible in the expanded view of FIG. 45, in some embodiments the deployment system 200' can also include an optional retrieval catheter 250. That is, in some embodiments the deployment system 200' includes the retrieval catheter 250 in addition to the control handle 210 (not shown), the outer sheath catheter 220', the middle deflectable catheter 230, the inner control catheter 240, and the control wires 243, 244, 245, 246, and 247. In the depicted embodiment, the retrieval catheter 250 includes a catheter shaft 252, a funnel-shaped member 254, two snare arms 256*a-b*, and a snare wire 258. The funnel-shaped member 254 is attached at a distal end portion of the catheter shaft 252. The snare arms 256*a-b* and the snare wire 258 are positioned within, and distally extend from, the funnel-shaped member 254.

The catheter shaft 252 of the retrieval catheter 250 defines a lumen. The middle deflectable catheter 230 extends within the lumen of the catheter shaft 252, and extends within the funnel-shaped member 254. The inner control catheter 240 extends within the lumen of the middle deflectable catheter 230. The retrieval catheter 250 extends within the lumen of the outer sheath catheter 220.

In some embodiments, the retrieval catheter 250 is only expressed from the outer sheath catheter 220 if/when the clinician user desires to initiate the valve retrieval process. Otherwise, the clinician user can keep the outer sheath catheter 220 remaining over the funnel-shaped member 254.

In some embodiments, the funnel-shaped member 254 is self-expandable. That is, when the funnel-shaped member 254 is expressed from the confines of the outer sheath catheter 220, the funnel-shaped member 254 will self-expand from its low-profile delivery configuration to its expanded conical shape as shown. In some embodiments, the funnel-shaped member 254 is constructed of a wire framework. For example, in some embodiments the funnel-shaped member 254 has a stent-like construction. In some such embodiments, the funnel-shaped member 254 can be constructed of a metal tube (e.g., Nitinol, stainless steel, alloy steel, titanium, etc.) that is laser cut and shape set into the conical shape as shown.

In some embodiments, the two snare arms 256*a-b* are arranged on opposite sides of the deflectable catheter 230 (e.g., at approximately 180° opposite of each other). The snare wire 258 extends between the distal ends of the snare arms 256*a-b* to form a loop, and also extends proximally to the control handle 210 (not shown). Accordingly, the clinician user can proximally pull on the snare wire 258 to cinch the looped snare wire 258 between the snare arms 256*a-b* to a smaller diameter.

The outer steerable sheath catheter 220' includes one or more selectively deflectable regions at or near the distal end portion of the outer steerable sheath catheter 220'. In some embodiments, the outer steerable sheath catheter 220' is selectively deflectable within one plane. In some embodiments, the outer steerable sheath catheter 220' is selectively deflectable within two differing planes. Accordingly, a clinician who is using/operating the deployment system 200' can induce and adjust a curvature of the distal end portion of the outer steerable sheath catheter 220'. In that manner, and as described further below, the clinician can selectively control the angle and direction along which the middle deflectable catheter 230, inner control catheter 240, and the prosthetic valve coupled thereto can be expressed from the outer steerable sheath catheter 220' during the deployment of a prosthetic heart valve using the deployment system 200'.

In some embodiments, the outer steerable sheath catheter 220' can be selectively deflected to define an angle between the longitudinal axis of the outer steerable sheath catheter 220' and the distal end portion of the outer steerable sheath catheter 220' that is in a range of between 130° and 160°, or between 120° and 150°, or between 110° and 140°, or between 100° and 130°, or between 90° and 120°, or between 80° and 110°, or between 80° and 100°, without limitation. In some embodiments, the angle can be greater than 160°, or greater than 150°, or greater than 140°, or greater than 135°, or greater than 130°, or greater than 120°, or greater than 110°, or greater than 100°, or greater than 90° without limitation.

The inner control catheter 240 includes a curved portion 242 (or a portion 242 that is selectively deflectable using the suture member 255). The curved portion 242 is elastically deformable. That is, while the curved portion 242 is located within the confines of the first lumen of the outer steerable sheath catheter 220', the curved portion 242 is essentially linear (or at least more linear than when the curved portion 242 is radially unconstrained). When the curved portion 242 of the inner control catheter 240 is distally expressed out (either by pushing the inner control catheter 240 distally or by pulling the outer steerable sheath catheter 220' proximally) from the confines of the first lumen of the outer steerable sheath catheter 220', the curved portion 242 either naturally elastically reconfigures to exhibit a pronounced curve (e.g., as shown in FIG. 45) or is linear and selectively deflectable by the application of lateral force from the suture member 255). Thus, in some embodiments it can be said that the natural shape of the inner control catheter 240 includes the naturally curved portion 242 that defines an interior angle θ. Or, in some embodiments the portion 242 is naturally linear and can be selectively deflected by application of force from the suture member 255). In some embodiments, the interior angle θ can be (either naturally curved or naturally linear and selectively deflectable) between 130° and 160°, or between 120° and 150°, or between 110° and 140°, or between 100° and 130°, or between 90° and 120°, or between 80° and 110°, or between 80° and 100°, or between 0 and 10°, or between 0 and 20°, or between 10° and 30°, or between 20° and 40°, or between 30 and 50, or between 40° and 60°, or between 50° and 70°, without limitation. In some embodiments, the interior angle θ can be less than 160°, or less than 150°, or less than 140°, or less than 135°, or less than 130°, or less than 120°, or less than 110°, or less than 100°, or less than 90°, or less than 80°, or less than 70°, or less than 60°, or less than 50°, or less than 40°, or less than 30°, or less than 20°, or less than 10°, or less than 5°, or 0° (i.e., linear) without limitation.

Still referring to FIGS. 44 and 45, in some cases an additional curve (or a controllably adjustable curve) of the curved portion 242 of the inner control catheter 240 can be needed or desired during the deployment of the valve 100. This can be the case, for example, when using a transfemoral deployment technique. In such a case, some embodiments include a suture (or wire) member 255 that extends from the retrieval catheter 250 to the third control wire 245 that is engaged with the distal tip member 241. In that arrangement, a clinician can manipulate the retrieval catheter 250 (e.g., pull it proximally) to add tension to the suture member 255 to curve or to increase the curvature of the curved portion 242 of the inner control catheter 240. In other words, by manipulating the retrieval catheter 250 to add tension to the suture member 255 a clinician can increase the curvature of the inner control catheter 240 (e.g., to be selectively bent from being naturally linear or bent beyond the natural curvature of the inner control catheter 240). This can be beneficial as the inner control catheter 240 is manipulated to make the tight turn within the right atrium to advance prosthetic heart valve from the inferior vena cava and through the annulus 12 of the native tricuspid valve 10. After that advancement, and at the appropriate time, the third control wire 245 can be pulled to disengage the suture member 255 from the third control wire 245.

The middle deflectable catheter 230 includes a selectively deflectable distal end portion 232 with at least one plane of deflection. In some embodiments, the selectively deflectable distal end portion 232 is deflectable in two planes. In some embodiments, the middle deflectable catheter 230 includes two or more separate selectively deflectable portions that are in same planes or in different planes.

In the depicted embodiment, the selectively deflectable distal end portion 232 is deflectable in a same plane as the plane of the curved portion 242 of the inner control catheter 240. Accordingly, when the selectively deflectable distal end portion 232 of the middle deflectable catheter 230 is deflected, the curvature of the combination of the middle deflectable catheter 230 and the inner control catheter 240 in relation to the longitudinal axis of the outer steerable sheath catheter 220' is increased beyond that of the interior angle θ alone. In some embodiments, the combined curvature of the middle deflectable catheter 230 and the inner control catheter 240 in relation to the axis of the outer steerable sheath catheter 220' can define an interior angle between 90° and 110°, or between 80° and 100°, or between 70° and 90°, or between 60° and 80°, or between 50° and 70°, or between 30° and 60°, or between 0° and 30°, without limitation.

Moreover, as described above, the angle of the distal end portion of the outer steerable sheath catheter 220' can also be selectively deflected to create curvature that is additive to the combined curvature of the middle deflectable catheter 230 and the inner control catheter 240. This high degree of selectively controllable curvature can be beneficial during deployment of a prosthetic valve (such as the valve 100) using the deployment system 200', as described further below.

The inner control catheter 240 can also include mechanical features for releasably coupling with a prosthetic heart valve (such as the valve 100, a valve that includes the frame 102', any other variation of the prosthetic heart valves described herein, and even other implantable medical devices). For example, in the depicted embodiment, the inner control catheter 240 includes one or more control wires and/or release pins 244 that can releasably couple the valve 100 to the inner control catheter 240 in a low-profile delivery configuration.

FIGS. 46 through 56 schematically illustrate a series of steps for another method of deploying an example prosthetic heart valve (the heart valve 100 with the frame 102' is used as an example) using the deployment system 200'. The illustrated deployment method uses a transfemoral approach. That is, the deployment system 200' including the prosthetic heart valve 100 is percutaneously advanced to the heart 1 by insertion into a femoral vein and advancement to the inferior vena cava ("IVC") to reach the native tricuspid valve via the right atrium ("RA").

Figure 46:
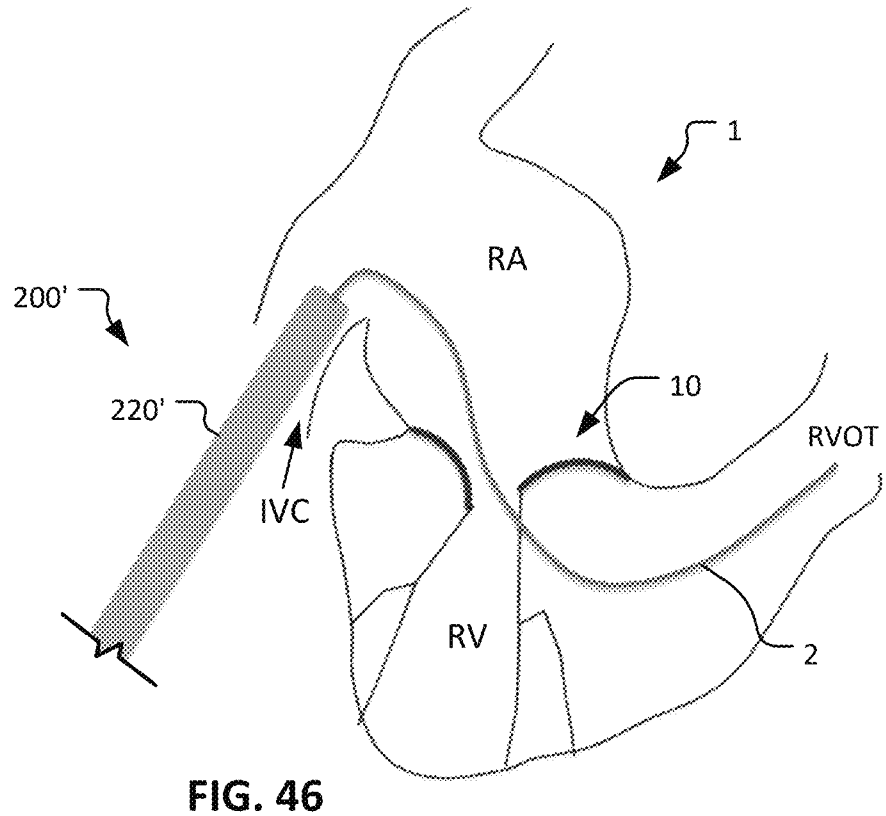
FIGS. 46-55 illustrate consecutive steps of another example transfemoral deployment method by which a prosthetic heart valve can be implanted at a native tricuspid valve location using the prosthetic heart valve deployment system of FIG. 44.

FIG. 46 illustrates the advancement of the deployment system 200' toward the RA via the IVC. That is, the outer steerable sheath catheter 220' (containing the heart valve 100 in its low-profile delivery configuration) can be advanced over a previously placed guidewire 2 that extends into the RA, across the native tricuspid valve 10, and into the right ventricle ("RV") (including into the RVOT in some examples).

Figure 47:
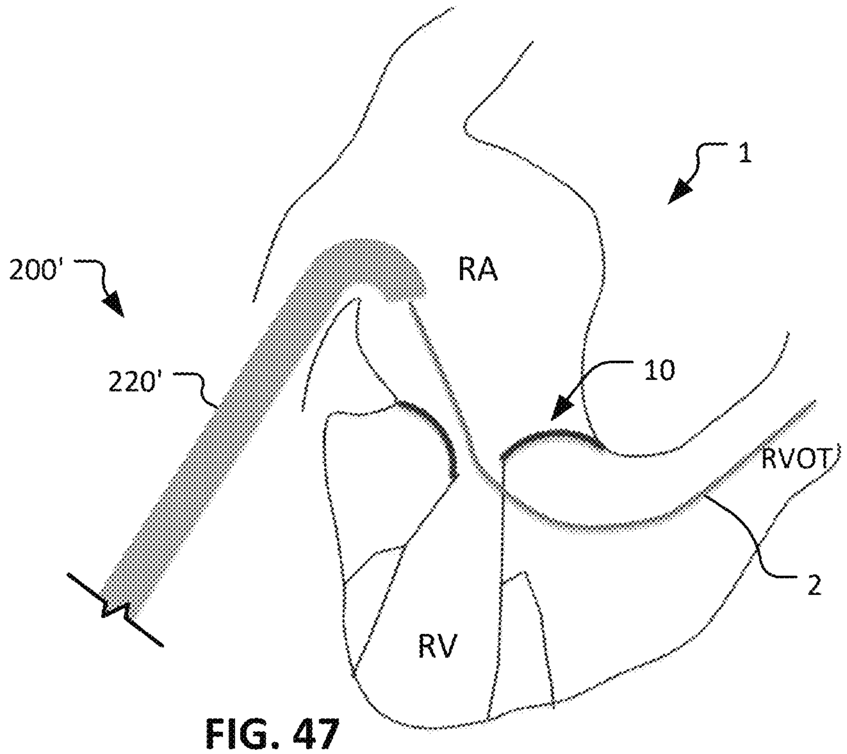

FIG. 47 illustrates farther advancement of the deployment system 200' and the emergence in the RA of a distal end portion of the outer steerable sheath catheter 220'. In addition, this illustrates that the distal end portion of the outer steerable sheath catheter 220' has been selectively deflected by the clinician to aim the distal end portion of the outer steerable sheath catheter 220' toward the native tricuspid valve 10.

Figure 48:
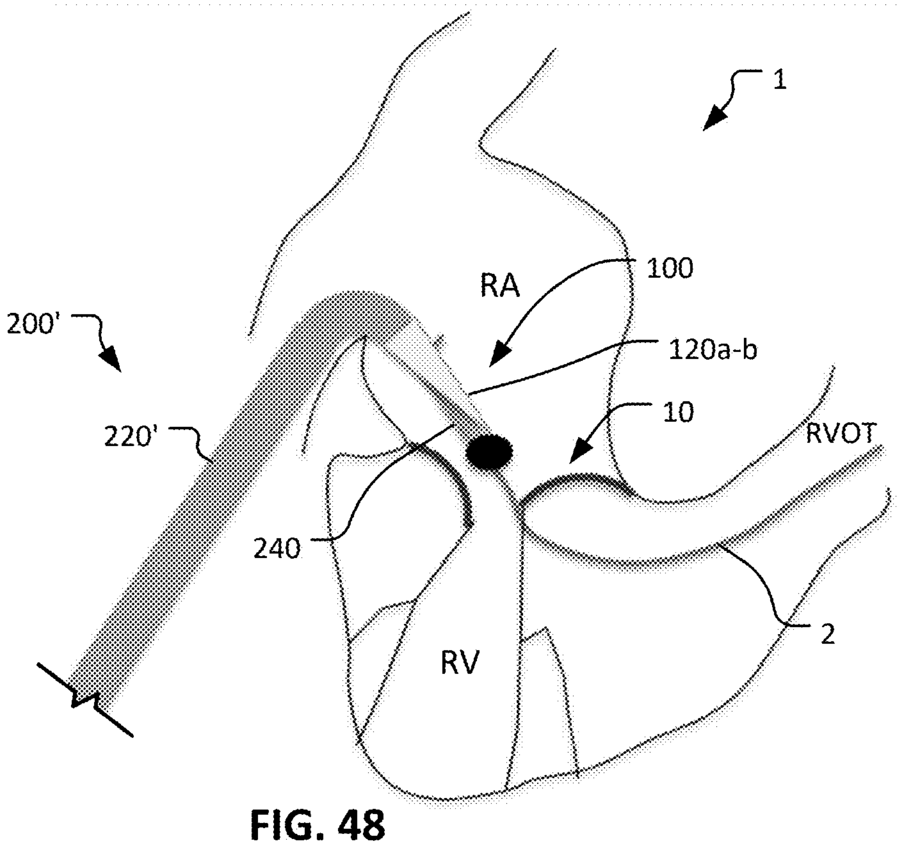

FIG. 48 illustrates the initial expression/emergence of the heart valve 100 out of the steerable sheath catheter 220' along a direction toward the native tricuspid valve 10. The clinician operating the deployment system 200' can cause the expression of the heart valve 100 from the steerable sheath catheter 220' while maintaining and/or adjusting the deflected arrangement/configuration of the distal end portion of the steerable sheath catheter 220'. That is, the emergence in the RA of the heart valve 100 out from the outer sheath catheter 220' can be performed by distally pushing the heart valve 100 out from the outer sheath catheter 220' by advancing the middle deflectable catheter 230 and inner control catheter 240 while maintaining the outer sheath catheter 220' substantially stationary (or while pulling the outer sheath catheter 220' proximally).

In the depicted arrangement, the anterior flaps **120*a*-*b* have emerged from the steerable sheath catheter 220', while the other portions of the heart valve 100 are still located within the steerable sheath catheter 220'. The anterior flaps 120*a*-*b* are coupled to the inner control catheter 240 via an anterior flap control wire 245 (see FIGS. 50-52) that is adjustable and removable by the clinician. As described below, the clinician can relax tension from the anterior flap control wire 245 to control and/or release the anterior flaps 120*a*-*b***.

Figure 49:
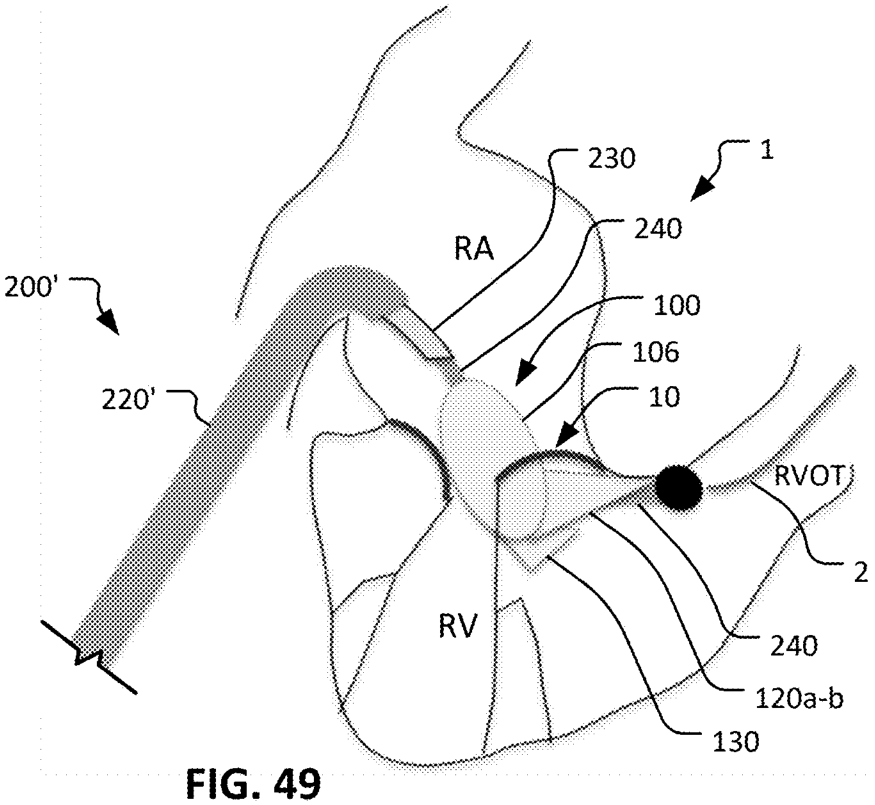

FIG. 49 illustrates the full emergence of the heart valve 100 out of the steerable sheath catheter 220'. To achieve this arrangement, the clinician has slid the inner control catheter 240 and the middle deflectable catheter 230 distally in relation to the steerable sheath catheter 220' (while holding the steerable sheath catheter 220' stationary). Accordingly, distal portions of the inner control catheter 240 and the middle deflectable catheter 230 are extended out from the steerable sheath catheter 220'. In this configuration, the naturally curved portion 242 (FIG. 45) of the inner control catheter 240 is in its curved configuration and is being utilized to position the end portions of the anterior flaps **120*a*-*b*** in the RVOT.

It should be noted that, in FIG. 49, the curved portion 242 of the inner control catheter 240 is arranged to curve in the opposite direction as compared to in FIG. 27 (which illustrates a trans-jugular vein approach to the native tricuspid valve 10 via the superior vena cava) and in FIG. 36 (which is another type of transfemoral delivery). In this configuration, the inner control catheter 240 has an S-shape. In some cases, the curvature of the inner control catheter 240 can be adjusted by the clinician by selectively applying tension to the suture member 255 (via the retrieval catheter 250) to manipulate the curvature of the curved portion 242 of the inner control catheter 240 as desired.

Figure 50:
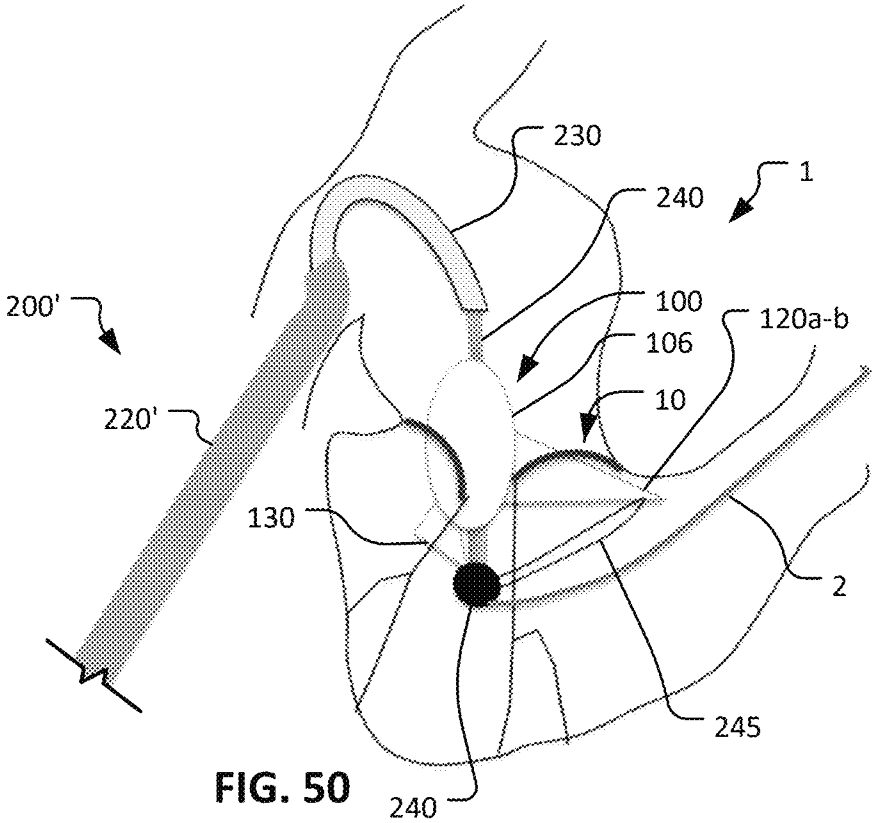

In FIG. 50, the anterior flap control wire 245 has been slackened (relieved of tension) by the clinician. In result, because the distal end portion of the inner control catheter 240 is flexible and releasably coupled to the heart valve 100 (e.g., by a posterior flap release pin/wire 246, an outflow end control wire 248, and an inflow end control wire 248—which are not visible in this view), the inner control catheter 240 deflects in a posterior direction, effectively eliminating the natural curve of the curved portion 242 (at least partially).

In addition, in FIG. 50, the clinician has manipulated the deployment system 200' in one or more other ways to align the heart valve 100 to the native tricuspid valve 1 in preparation for deployment of the heart valve 100. For example, the middle deflectable catheter 230 has been selectively deflected (curved) by the clinician. Further, in some embodiments the deflection of the distal end portion of the steerable sheath catheter 220' is adjusted as compared to the arrangement shown in FIGS. 48 and 49. In such ways, the inner control catheter 240, and the heart valve 100 coupled thereto, is aligned approximately perpendicularly to the plane defined by the annulus of the native tricuspid valve 1.

Figure 51:
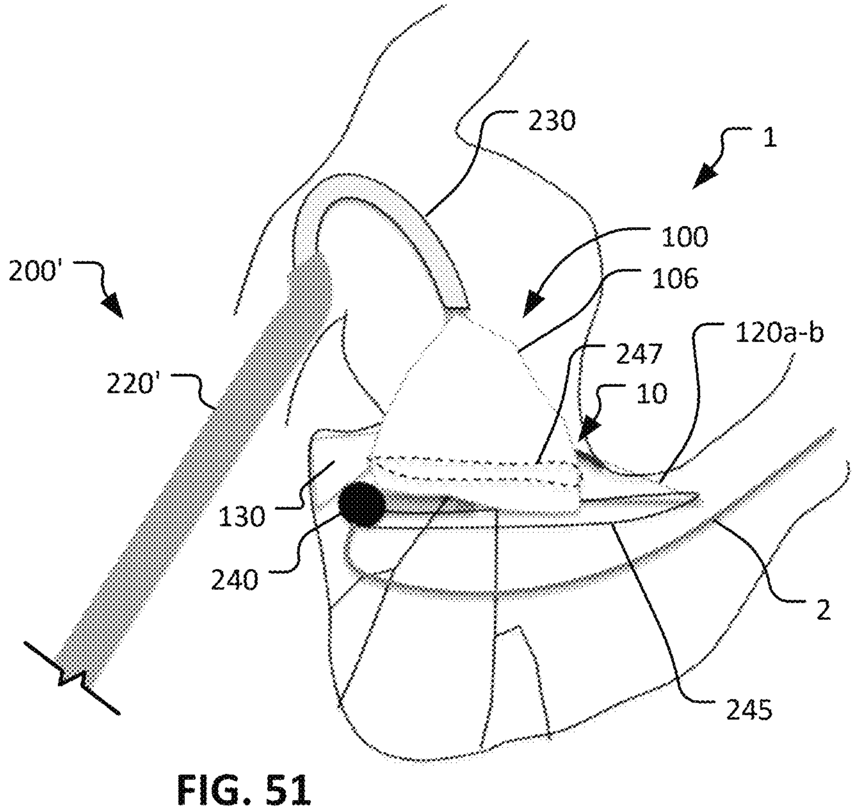

In FIG. 51, the clinician has slackened (relieved tension) the outflow end control wire 247. In result, the outflow end of the main body 106 of the heart valve 100 has radially expanded and the posterior flap 130 (which extends from the outflow end of the main body 106) has become seated against the posterior wall of the LV beneath the annulus of the native tricuspid valve 10. Because the inner control catheter 240 is flexible and still coupled to the posterior flap 130, the distal end of the inner control catheter 240 moves along with the posterior flap 130.

Figure 52:
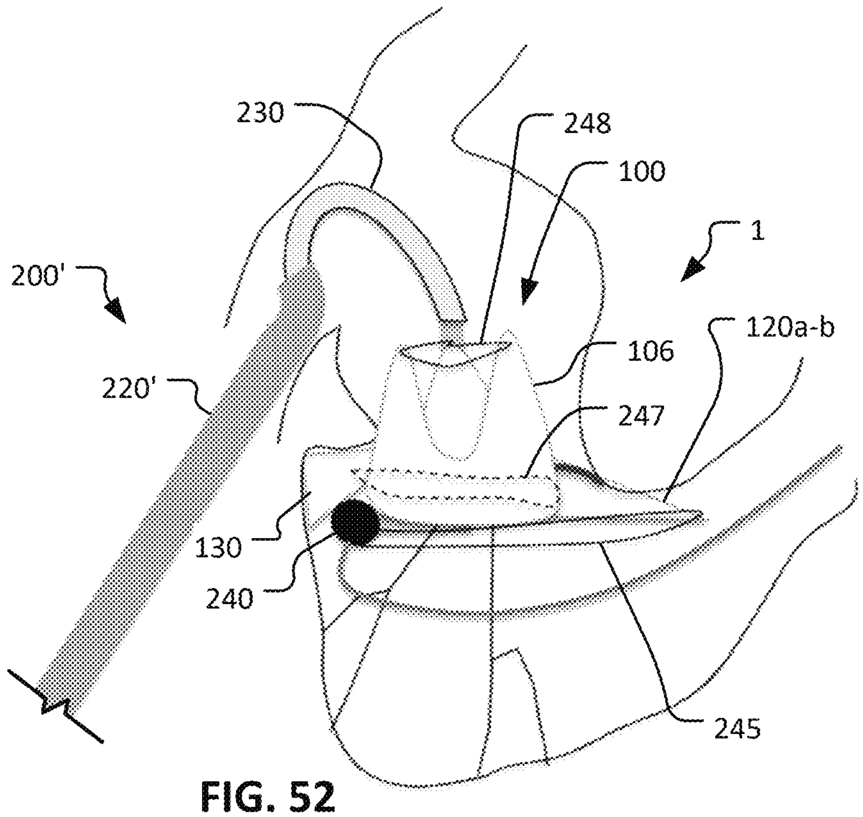

In FIG. 52, the clinician has slackened (relieved tension) the inflow end control wire 248. In result, the inflow end of the main body 106 of the heart valve 100 has radially expanded. In this configuration, the main body 106 of the heart valve 100 is fully expanded. In addition, the anterior flaps **120*a*-*b* and the posterior flap 130** are seated in their desired anatomical positions.

Figure 53:
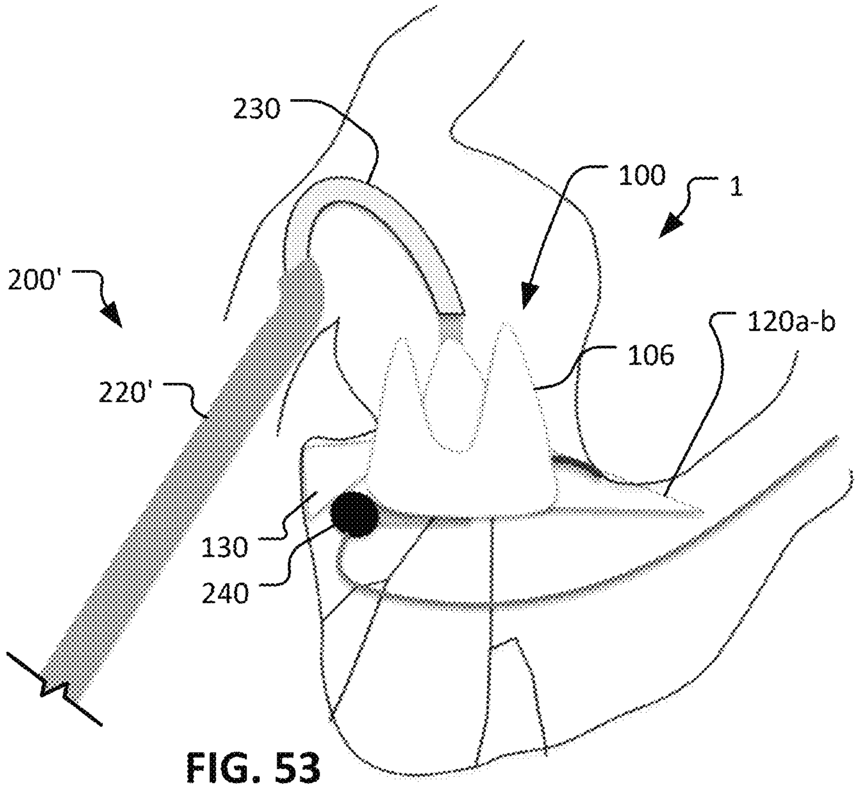

In FIG. 53, the anterior flap control wire 245, the outflow end control wire 247, and the inflow end control wire 248 have been removed by the clinician. However, the posterior flap release pin/wire 246 is still coupled to the posterior flap 130. Accordingly, the distal end portion of the inner control catheter 240 is still deflected posteriorly. In addition, in some embodiments a posterior arm release pin/wire 249 (not visible) of the inner control catheter 240 may be releasably coupled to the posterior arm 150 (see FIG. 39) of the heart valve 100 to control its deployment.

Figure 54:
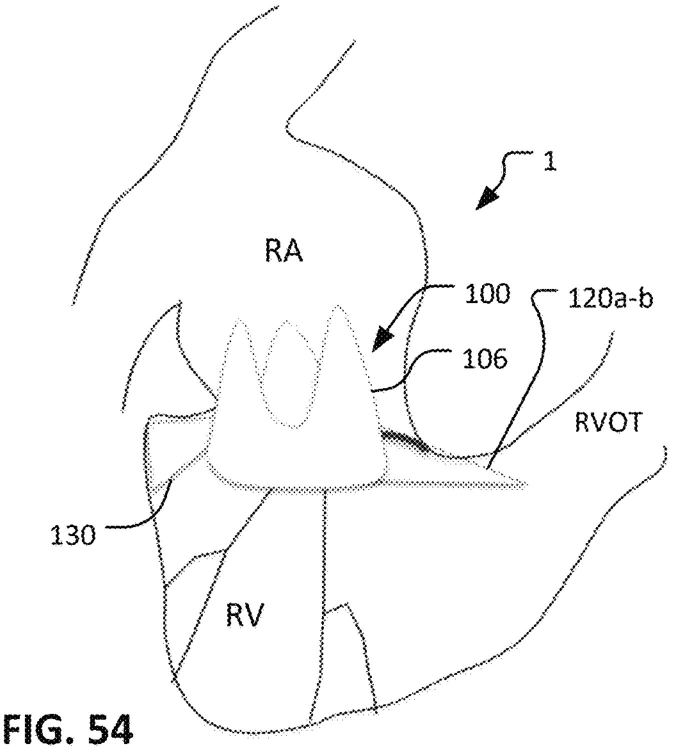
Figure 55:
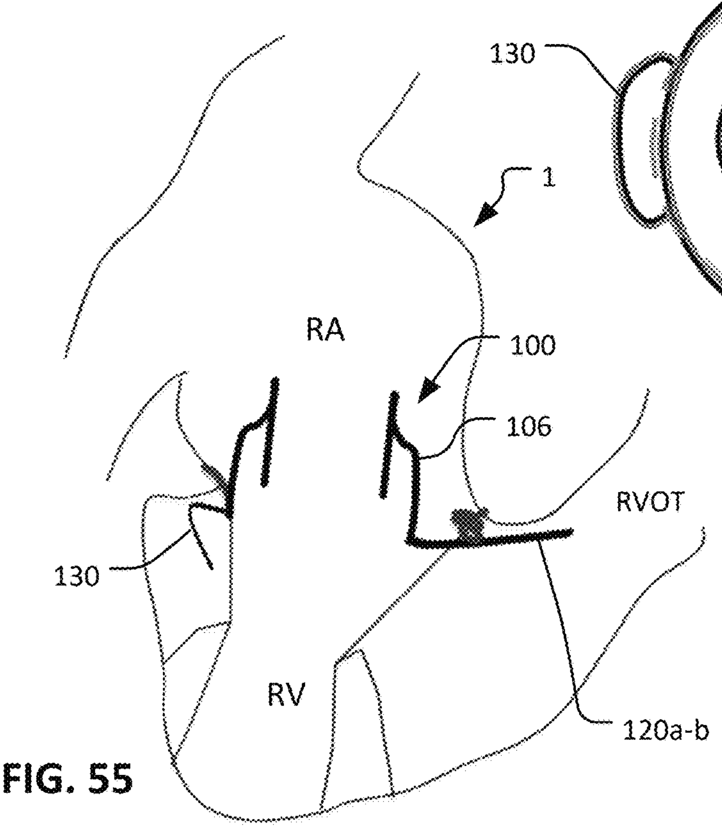

FIGS. 54 and 55 show two different representations of the fully deployed heart valve 100 after removal of the deployment system 200' and the guidewire 2. The heart valve 100 was, in this example, deployed in a transfemoral approach via the IVC. The implanted heart valve 100 is in engagement with the heart 1 and functioning as a prosthetic tricuspid valve between the RA and the RV.

Figure 56:
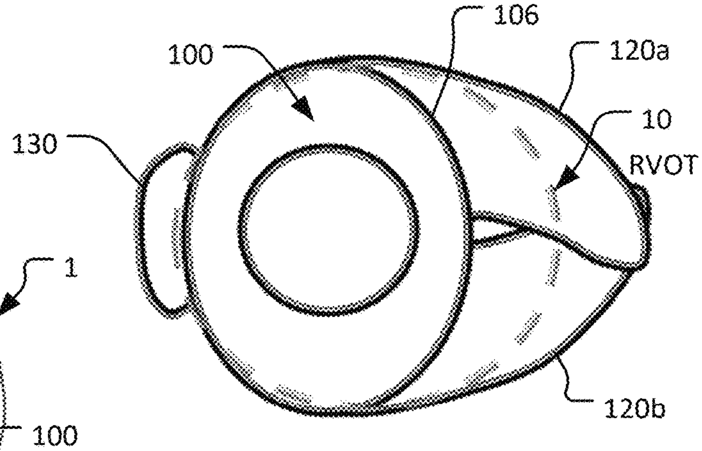
FIG. 56 illustrates a view of the deployed prosthetic heart valve looking from the right atrium towards the right ventricle.

FIG. 56 shows a view of the deployed heart valve 100 looking from the RA towards the RV. The annulus of the native tricuspid valve 10 is shown in dashed lines. This illustration shows that the annular opening of the native tricuspid valve 100 is filled/covered by the main body 106 and portions of the anterior flaps 120*a-b* of the heart valve 100. Terminal end portions of the anterior flaps 120*a-b* extend into the RVOT. The posterior flap 130 is below the annulus of the native tricuspid valve 10.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment in part or in whole. Conversely, various features that are described in the context of a single embodiment can also be implemented in multiple embodiments separately or in any suitable subcombination. Moreover, although features may be described herein as acting in certain combinations and/or initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Although a number of implementations have been described in detail above, other modifications are possible. For example, the steps depicted in the figures do not require the particular order shown, or sequential order, to achieve desirable results. In addition, other steps may be provided, or steps may be eliminated, from the described flows, and other components may be added to, or removed from, the described systems. Accordingly, other implementations are within the scope of the following claims.

What is claimed is:

1. A method of deploying a prosthetic heart valve, the method comprising:

advancing, via a femoral vein and an inferior vena cava, the prosthetic heart valve toward a native tricuspid valve while the prosthetic heart valve is releasably coupled to a prosthetic heart valve deployment system and diametrically constrained in a low-profile delivery configuration within a first lumen of an outer steerable sheath catheter, wherein the prosthetic heart valve comprises:

a main body comprising an inflow end portion and an outflow end portion; and one or more anterior flaps extending from the outflow end portion;

with a distal end portion of the outer steerable sheath catheter in a right atrium, deflecting the distal end portion of the outer steerable sheath catheter toward the native tricuspid valve; and expressing the prosthetic heart valve from the outer steerable sheath catheter while maintaining a position of the outer steerable sheath catheter substantially stationary, wherein the inflow end portion of the prosthetic heart valve is expressed only after an entirety of the outflow end portion has been expressed, and wherein the one or more anterior flaps extend into a right ventricular outflow tract (RVOT) as a result of the expressing of the prosthetic heart valve from the outer sheath, and wherein the prosthetic heart valve deployment system comprises:

a middle deflectable catheter slidably disposed in the first lumen and defining a second lumen, the middle deflectable catheter comprising a selectively deflectable distal end portion; and an inner control catheter slidably disposed in the second lumen and including one or more control wires that are releasably coupled with the prosthetic heart valve.

2. The method of claim 1, wherein the inner control catheter includes a curved distal end portion that is curved by less than 20° when constrained in the first lumen.

3. The method of claim 2, further comprising:

advancing the inner control catheter relative to the outer sheath to allow the curved distal end portion to become unconstrained and to elastically transition to a curved configuration in an anterior direction.

4. The method of claim 1, wherein the one or more anterior flaps engage with a lateral wall of the RVOT to provide anchoring during diastole.

5. The method of claim 1, wherein a portion of an opening defined by the native tricuspid valve is covered and fluidly sealed by the one or more anterior flaps.

6. The method of claim 1, wherein the prosthetic heart valve deployment system and the prosthetic heart valve are advanced over a pre-placed guidewire.

7. The method of claim 1, wherein the outflow end portion of the prosthetic heart valve comprises one or more posterior flaps that engage with a posterior shelf and/or with a wall of the right ventricle just inferior to an annulus of the native tricuspid valve.

* * * * *